United States Patent
Ferrer Montiel et al.

(10) Patent No.: US 9,771,392 B2
(45) Date of Patent: *Sep. 26, 2017

(54) COMPOUNDS WHICH INHIBIT NEURONAL EXOCYTOSIS

(71) Applicant: Lubrizol Advanced Materials, Inc., Cleveland, OH (US)

(72) Inventors: Antonio Vicente Ferrer Montiel, Alicante (ES); Gregorio Fernández Ballester, Murcia (ES); José María García Antón, Barcelona (ES); Cristina Carreño Serraïma, Barcelona (ES); Núria Almiñana Doménech, Barcelona (ES); Raquel Delgado González, Barcelona (ES)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 50 days.

This patent is subject to a terminal disclaimer.

(21) Appl. No.: 14/391,562

(22) PCT Filed: Apr. 12, 2013

(86) PCT No.: PCT/EP2013/057658
§ 371 (c)(1),
(2) Date: Oct. 9, 2014

(87) PCT Pub. No.: WO2013/153192
PCT Pub. Date: Oct. 17, 2013

(65) Prior Publication Data
US 2015/0140046 A1    May 21, 2015

Related U.S. Application Data

(60) Provisional application No. 61/652,655, filed on May 29, 2012.

(30) Foreign Application Priority Data

Apr. 13, 2012 (EP) .................................... 12382146

(51) Int. Cl.
| | | |
|---|---|---|
| C07K 7/06 | (2006.01) |
| A61K 8/64 | (2006.01) |
| A61Q 15/00 | (2006.01) |
| A61Q 19/08 | (2006.01) |
| A61K 38/08 | (2006.01) |
| A61K 45/06 | (2006.01) |
| A61Q 7/00 | (2006.01) |
| A61K 38/00 | (2006.01) |

(52) U.S. Cl.
CPC .................. *C07K 7/06* (2013.01); *A61K 8/64* (2013.01); *A61K 38/08* (2013.01); *A61K 45/06* (2013.01); *A61Q 7/00* (2013.01); *A61Q 15/00* (2013.01); *A61Q 19/08* (2013.01); *A61K 38/00* (2013.01); *A61K 2800/43* (2013.01); *A61K 2800/48* (2013.01); *A61K 2800/51* (2013.01); *A61K 2800/52* (2013.01); *A61K 2800/522* (2013.01); *A61K 2800/524* (2013.01); *A61K 2800/782* (2013.01)

(58) Field of Classification Search
None
See application file for complete search history.

(56) References Cited

U.S. PATENT DOCUMENTS

| | | |
|---|---|---|
| 5,437,291 A | 8/1995 | Pasricha et al. |
| 5,670,484 A | 9/1997 | Binder |
| 5,714,468 A | 2/1998 | Binder |
| 5,766,605 A | 6/1998 | Sanders et al. |
| 6,063,768 A | 5/2000 | First |
| 6,113,915 A | 9/2000 | Aoki et al. |
| 6,139,845 A | 10/2000 | Donovan |
| 6,265,379 B1 | 7/2001 | Donovan |
| 6,299,893 B1 | 10/2001 | Schwartz et al. |
| 6,358,917 B1 | 3/2002 | Carruthers et al. |
| 6,358,926 B2 | 3/2002 | Donovanq |
| 6,423,319 B1 | 7/2002 | Brooks et al. |
| 6,458,365 B1 | 10/2002 | Aoki et al. |

(Continued)

FOREIGN PATENT DOCUMENTS

| | | |
|---|---|---|
| EP | 1 180 524 A1 | 2/2002 |
| EP | 2 123 673 A1 | 11/2009 |

(Continued)

OTHER PUBLICATIONS

Sequence information (retrieved from https://patentscope.wipo.int/search/en/detail.jsf;jsessionid=CF5BC8D9AE23FBA3400F10486C3A1290.wapp2nB?docId=WO2013143026&recNum=1&tab=PCTDocuments&maxRec=&office=&prevFilter=&sortOption=&queryString= on Sep. 24, 2015, 1 page).*

(Continued)

*Primary Examiner* — Karlheinz R Skowronek
*Assistant Examiner* — Ronald Niebauer
(74) *Attorney, Agent, or Firm* — Fay Sharpe LLP

(57) ABSTRACT

Compounds of general formula (I): $R_1\text{-}W_n\text{-}X_m\text{-}AA_1\text{-}AA_2\text{-}AA_3\text{-}AA_4\text{-}AA_5\text{-}AA_6\text{-}AA_7\text{-}AA_8\text{-}AA_9\text{-}Y_p\text{-}Z_q\text{-}R_2$ (I) their stereoisomers, mixtures thereof and/or their cosmetically or pharmaceutically acceptable salts, preparation processes, cosmetic or pharmaceutical compositions which contain them and their use in medicine, particularly in the treatment and/or prevention of pain, inflammation, itching, neurological, compulsive and/or neuropsychiatric diseases and/or disorders and in processes of treatment and/or care of the skin, hair and/or mucous membranes mediated by neuronal exocytosis.

13 Claims, No Drawings

(56) References Cited

U.S. PATENT DOCUMENTS

| | | | |
|---|---|---|---|
| 6,500,436 | B2 | 12/2002 | Donovan |
| 6,565,870 | B1 | 5/2003 | Donovan |
| 6,620,415 | B2 | 9/2003 | Donovan |
| 6,623,742 | B2 | 9/2003 | Voet |
| 6,641,820 | B1 | 11/2003 | Donovan |
| 6,683,049 | B1 | 1/2004 | Aoki et al. |
| 6,740,321 | B1 | 5/2004 | Donovan |
| 6,776,991 | B2 | 8/2004 | Naumann |
| 6,838,434 | B2 | 1/2005 | Voet |
| 6,841,156 | B2 | 1/2005 | Aoki et al. |
| 6,861,058 | B2 | 3/2005 | Aoki et al. |
| 6,869,610 | B2 | 3/2005 | Aoki et al. |
| 6,872,397 | B2 | 3/2005 | Aoki et al. |
| 6,887,476 | B2 | 5/2005 | Aoki et al. |
| 6,939,852 | B2 | 9/2005 | Graham |
| 6,974,578 | B1 | 12/2005 | Aoki et al. |
| 6,974,793 | B2 | 12/2005 | Donovan |
| 7,091,176 | B2 | 8/2006 | Aoki et al. |
| 7,220,422 | B2 | 5/2007 | First |
| 7,238,357 | B2 | 7/2007 | Barron |
| 7,255,865 | B2 | 8/2007 | Walker |
| 7,255,866 | B2 | 8/2007 | Voet |
| 7,270,287 | B2 | 9/2007 | First |
| 7,357,934 | B2 | 4/2008 | Donovan et al. |
| 7,393,537 | B2 | 7/2008 | Ackerman |
| 7,465,458 | B2 | 12/2008 | First |
| 7,468,189 | B2 | 12/2008 | Aoki et al. |
| 7,704,511 | B2 | 4/2010 | Turkel et al. |
| 7,704,524 | B2 | 4/2010 | Donovan |
| 7,709,440 | B2 | 5/2010 | Shaari |
| 7,811,586 | B2 | 10/2010 | Brooks |
| 7,811,587 | B2 | 10/2010 | Donovan |
| 7,838,007 | B2 | 11/2010 | Brin et al. |
| 8,048,423 | B2 | 11/2011 | First |
| 8,946,166 | B2 * | 2/2015 | Garcia Sanz ...... C07K 14/4703 424/401 |
| 2003/0139345 | A1 * | 7/2003 | Netke ............... C12N 9/6491 514/19.4 |
| 2003/0224019 | A1 | 12/2003 | O'Brien |
| 2009/0280140 | A1 * | 11/2009 | Laal .............. C07K 14/36 424/190.1 |
| 2010/0028385 | A1 | 2/2010 | Nassif |
| 2010/0266638 | A1 | 10/2010 | Turkel et al. |
| 2011/0052636 | A1 | 3/2011 | Gaxiola et al. |
| 2011/0206731 | A1 | 8/2011 | First |
| 2011/0280978 | A1 | 11/2011 | Steinsapir |

FOREIGN PATENT DOCUMENTS

| | | |
|---|---|---|
| EP | 1 856 139 B1 | 4/2011 |
| KR | 101 046 426 B1 | 7/2011 |
| WO | WO 97/34620 A1 | 9/1997 |
| WO | WO 02/074327 A2 | 9/2002 |
| WO | WO 03/011333 A1 | 2/2003 |
| WO | WO 2006/050611 A1 | 5/2006 |
| WO | WO 2006/094193 A2 | 9/2006 |
| WO | WO 2009/139984 A2 | 11/2009 |
| WO | WO2010/021822 * | 2/2010 |
| WO | WO 2010/037395 * | 4/2010 |
| WO | WO 2010/114828 A1 | 10/2010 |
| WO | WO 2011/009626 A1 | 1/2011 |
| WO | WO 2011/038015 A1 | 3/2011 |
| WO | WO 2011/048443 A1 | 4/2011 |
| WO | WO2013/143026 * | 10/2013 |

OTHER PUBLICATIONS

Sequence listing (retrieved from sequence listing #38082 retrieved from https://patentscope.wipo.int/search/en/detail.jsf;jsessionid=CF5BC8D9AE23FBA3400F10486C3A1290.wapp2nB?docId=WO2013143026&recNum=1&tab=PCTDocuments&maxRec=&office=&prevFilter=&sortOption=&queryString= on Sep. 24, 2015, 1 page).*

Liniment definition (retrieved from http://www.pharmainfo.net/liniments on Jan. 30, 2017, 2 pages).*
FDA News, "FDA Notifies Public of Adverse Reactions Linked to Botox Use," pp. 1-2 Feb. 8, 2008.
Coté, et al., "Botulinum toxin type A injections: Adverse events reported to the US Food and Drug Administration in therapeutic and cosmetic cases," J. Amer. Acad. Derm. 53(3), pp. 407-415 (2005).
Schaivo, et al., "Bases Moleculares del tétanosy del botulismo," Investigacion y Ciencia 234, pp. 46-55 (1996) (English Abstract only).
Montecucco, et al., "Mechanism of action of tetanus and botulinum neurotoxins," Mol. Microbiol., 13(1), pp. 1-8 (1994).
Schiavo, et al., "Tetanus and botulinum neurotoxins are zinc proteases specific for components of the neuroexocytosis apparatus," Ann. NY Acad. Sci. 710, pp. 65-75 (1994). (Abstract only).
Calakos, et al., "Synaptic vesicle biogenesis, docking and fusion: a molecular description," Physiol. Rev. 76, pp. 1-29 (1996).
Sutton, et al., "Crystal structure of a SNARE complex involved in synaptic exocytosis at 2.4A resolution," Nature, 395, pp. 347-353 (1998).
Apland, et al., "Peptides that mimic the carboxy-terminal domain of SNAP-25 block acetylcholine release at an Aplysia synapse," J. Appl. Toxicol.19, Suppl. 1:S23-S26 (1999).
Mehta, et al., "SNAP-25 and synaptotagmin involvement in the final $Ca^{2+}$-dependent triggering of neurotransmitter exocytosis," Proc. Natl. Acad. Sci. 93, pp. 10471-10476 (1996).
Ferrer-Montiel, et al., "The 26-mer peptide released from SNAP-25 cleavage by botulinum neurotoxin E inhibits vesicle docking," FEBS Lett. 435, pp. 84-88 (1998).
Gutierrez, et al., "A peptide that mimics the carboxy-terminal domain of SNAP-25 blocks $Ca^{2+}$-dependent exocytosis in chromaffin cells," FEBS Lett. 372, pp. 39-43 (1995).
Gutierrez, et al., "A peptide that mimics the C-terminal sequence of SNAP-25 inhibits secretory vesicle docking in chromaffin cells," J. Biol. Chem., 272 pp. 2634-2639 (1997).
Blanes-Mira, et al., "Small peptides patterned after the N-terminus domain of SNAP-25 inhibit SNARE complex assembly and regulated exocytosis," J. Neurochem. 88, pp. 124-135 (2004).
Martin, et al., "Inhibition of insulin release by synthetic peptides show that the H3 region at the C-terminal domain of syntaxin-1 is crucial for $Ca^{2+}$ but not for guanosine 5'-[g-thio]triphosphate-induced secretion," Biochem. J. 320, pp. 201-205 (1996).
Cornille, "Inhibition of neurotransmitter release by synthetic prolinērich peptides shows that the N-terminal domain of vesicle-associated membrane protein/synaptobrevin is critical for neuroexocytosis," J. Biol. Chem., 270, pp. 16826-16830 (1995).
Ilardi, et al., "Snapin: A SNARE associated protein implicated in synaptic transmission," Nat. Neurosci., 2(2), pp. 119-124 (1999).
Blanes-Mira, et al., "Identification of SNARE complex modulators that inhibit exocytosis from an α-helix-constrained combinatorial library," Biochem J., 375, pp. 159-166 (2003).
Blanes-Mira, et al., "A synthetic hexapeptide (Argireline®) with antiwrinkle activity," Int. J. Cosmetic Sci., 24, pp. 303-310 (2002).
IUPAC-IUB Commission of Biochemical Nomenclature specified in Eur. J. Biochem., 138, pp. 9-37 (1984).
Roberts, et al., "Unusual amino acids in peptide synthesis," The Peptides, vol. 5, Chapter VI, Gross and Meienhofer J., Eds., Academic Press, New York, pp. 341-449 (1983).
Stewart, et al., "Solid-phase Peptide Synthesis," $2^{nd}$ Edition, pp. 1-20 (1984).
Bodanzsky, et al., "The practice of Peptide Synthesis," pp. 75-126 (1994).
Llyod-Williams, et al., "Chemical Approaches to the Synthesis of Peptides and Proteins," CRC, Synthesis in solution, Enzymatic synthesis, pp. 19-93 (1997).
Kullman, "Proteases as catalysts for enzymic syntheses of opioid peptides," J. Biol. Chem. 255(17), pp. 8234-8238 (1980).
Llyod-Williams, et al., "Convergent Solid-Phase Peptide Synthesis," Tetrahedron 49(48), pp. 11065-11133 (1993).
Atherton, et al, "Solid Phase Peptide Synthesis: A practical approach," IRL Oxford University Press. pp. 1-61 (1989).

(56) References Cited

OTHER PUBLICATIONS

Matsueda, et al., "A p-methylbenzhydrylamine resin for improved solid phase synthesis of peptide amides," Peptides, 2, pp. 45-50 (1981).

Barlos, et al., "Darstellung geschützter Peptid-Fragmente Unter Einsatz Substituierter Triphenylmethyl-Harze," Tetrahedron Lett. 30, No. 30, pp. 3943-3946 (1989). (English Abstract only).

Barlos, et al., "Veresterung von partiell geschützten Peptid Fragmenten mit Harzen. Einsatz von 2-Chlortritylchlorid zur Synthese von Leu$^{15}$-Gastrin I," Tetrahedron Lett. 30, pp. 3947-3950 (1989). (English Abstract only).

Albericio, et al., "Preparation and application of the 5-(4-(9-fluoroenylmethyloxycarbonyl) aminomethyl-3,5-dimethoxyphenoxy) valeric acid (PAL) handle for the solid phase synthesis of C-terminal peptide amides under mild conditions," J. Org. Chem., 55, pp. 3730-3743 (1990).

Rink, "Solid phase synthesis of protected peptide fragments using a trialkoxy-diphenyl-methylester resin," Tetrahedron Lett., 28, pp. 3787-3790 (1987).

Wang et al., "p-Alkoxybenzyl Alcohol Resin and p-Alkoxybenzyloxycarbonylhydrazide Resin for Solid Phase Synthesis of Protected Peptide Fragments," J. Am. Chem. Soc., 95(4), pp. 1328-1333 (1973).

Wilkinson, et al., "Harry's Cosmeticology," Seventh Edition Longman House, Essex, G.B. pp. 50-73 and 757-799 (1982).

Schaab, et al., "Impregnating Fabrics with Microcapsules," HAPPI pp. 84-86 (May 1986).

Nelson, "Application of microencapsulation in textiles," Int. J. Pharm., 242(1-2), pp. 55-62 (2002).

Elsner, et al., "Antimicrobials and the skin. Physiological and Pathological Flora," in Biofunctional Textiles and the Skin, Curr. Probl. Dermatol. V. 33, pp. 35-41(2006).

Malcolm et al., "Controlled release of a model antibacterial drug from a novel self-lubricating silicone biomaterial," J. Cont. Release, 97(2) pp. 313-320 (2004).

Gottschalck, et al., Eds., "CTFA International Cosmetic Ingredient Dictionary and Handbook," 12$^{th}$ Edition, pp. 3040-3065 (2008).

Kaiser, et al., "Color test for detection of free terminal amino groups in the solid-phase synthesis of peptides," Anal. Biochem., 34(2), pp. 595-598 (1970).

Christensen, "A Qualitative Test for Monitoring Coupling Completeness in Solid Phase Peptide Synthesis Using Chloranil," Acta Chem. Scand., 33B, pp. 763-766 (1979).

Berge, et al., "Pharmaceutical Salts," Journal of Pharmaceutical Sciences, vol. 66(1), pp. 1-20 (1977).

Rossetto, et al., "An Update on the Mechanism of Action of Tetanus and Botulinum Neurotoxins," Acta. Chim. Slov., vol. 58, pp. 702-707 (2011).

\* cited by examiner

SEQUENCE LISTING

```
<160> NUMBER OF SEQ ID NOS: 131

<210> SEQ ID NO 1
<211> LENGTH: 8
<212> TYPE: PRT
<213> ORGANISM: Artificial Sequence
<220> FEATURE:
<223> OTHER INFORMATION: Synthetic peptide

<400> SEQUENCE: 1

Gln Arg Glu His Arg Lys Met Asp
1               5

<210> SEQ ID NO 2
<211> LENGTH: 8
<212> TYPE: PRT
<213> ORGANISM: Artificial Sequence
```

```
<220> FEATURE:
<223> OTHER INFORMATION: Synthetic peptide

<400> SEQUENCE: 2

Lys Gln Glu His His Lys Met Asp
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic peptide

<400> SEQUENCE: 3

Lys Asn Glu His Arg Lys Met Asp
1               5

<210> SEQ ID NO 4
<211> LENGTH: 8
<212> TYPE: PRT
<213> ORGANISM: Artificial Sequence
<220> FEATURE:
<223> OTHER INFORMATION: Synthetic peptide

<400> SEQUENCE: 4

Lys Gln Glu His Arg Lys Met Asp
1               5

<210> SEQ ID NO 5
<211> LENGTH: 8
<212> TYPE: PRT
<213> ORGANISM: Artificial Sequence
<220> FEATURE:
<223> OTHER INFORMATION: Synthetic peptide

<400> SEQUENCE: 5

His Gln Glu His Arg Lys Met Asp
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic peptide

<400> SEQUENCE: 6

Glu Gln Glu His Arg Lys Met Asp
1               5

<210> SEQ ID NO 7
<211> LENGTH: 8
<212> TYPE: PRT
<213> ORGANISM: Artificial Sequence
<220> FEATURE:
<223> OTHER INFORMATION: Synthetic peptide

<400> SEQUENCE: 7

Asp Lys Glu His Arg Lys Met Asp
1               5

<210> SEQ ID NO 8
<211> LENGTH: 8
<212> TYPE: PRT
<213> ORGANISM: Artificial Sequence
<220> FEATURE:
```

<223> OTHER INFORMATION: Synthetic peptide

<400> SEQUENCE: 8

Asn Arg Glu His Arg Lys Met Asp
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic peptide

<400> SEQUENCE: 9

His Glu Glu His Arg Met Met Asp
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic peptide

<400> SEQUENCE: 10

His Gln Tyr Asp Glu Val Met Asp
1               5

<210> SEQ ID NO 11
<211> LENGTH: 8
<212> TYPE: PRT
<213> ORGANISM: Artificial Sequence
<220> FEATURE:
<223> OTHER INFORMATION: Synthetic peptide

<400> SEQUENCE: 11

Asp Gln Glu His Gln Lys Met Asp
1               5

<210> SEQ ID NO 12
<211> LENGTH: 8
<212> TYPE: PRT
<213> ORGANISM: Artificial Sequence
<220> FEATURE:
<223> OTHER INFORMATION: Synthetic peptide

<400> SEQUENCE: 12

Asp Lys Glu His Asn Lys Met Asp
1               5

<210> SEQ ID NO 13
<211> LENGTH: 8
<212> TYPE: PRT
<213> ORGANISM: Artificial Sequence
<220> FEATURE:
<223> OTHER INFORMATION: Synthetic peptide

<400> SEQUENCE: 13

Glu Asn Glu His Asp Lys Met Asp
1               5

<210> SEQ ID NO 14
<211> LENGTH: 8
<212> TYPE: PRT
<213> ORGANISM: Artificial Sequence
<220> FEATURE:
<223> OTHER INFORMATION: Synthetic peptide

<400> SEQUENCE: 14

Asp Gln Glu His Arg Lys Met Asp
1               5

<210> SEQ ID NO 15
<211> LENGTH: 8
<212> TYPE: PRT
<213> ORGANISM: Artificial Sequence
<220> FEATURE:
<223> OTHER INFORMATION: Synthetic peptide

<400> SEQUENCE: 15

Asn Gln Glu His Arg Lys Met Asp
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic peptide

<400> SEQUENCE: 16

Asp Gln Glu Glu Gln Ile Met Asp
1               5

<210> SEQ ID NO 17
<211> LENGTH: 8
<212> TYPE: PRT
<213> ORGANISM: Artificial Sequence
<220> FEATURE:
<223> OTHER INFORMATION: Synthetic peptide

<400> SEQUENCE: 17

Asp Gln Asp Lys Gln His Met Asp
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic peptide

<400> SEQUENCE: 18

Glu Asn Glu His Arg Lys Met Asp
1               5

<210> SEQ ID NO 19
<211> LENGTH: 8
<212> TYPE: PRT
<213> ORGANISM: Artificial Sequence
<220> FEATURE:
<223> OTHER INFORMATION: Synthetic peptide

<400> SEQUENCE: 19

Glu His Glu His Arg Lys Met Asp
1               5

<210> SEQ ID NO 20
<211> LENGTH: 8
<212> TYPE: PRT
<213> ORGANISM: Artificial Sequence
<220> FEATURE:
<223> OTHER INFORMATION: Synthetic peptide

```
<400> SEQUENCE: 20

Gln Asn Glu His His Lys Met Asp
1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic peptide

<400> SEQUENCE: 21

Lys Lys Glu His Gln Lys Met Asp
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic peptide

<400> SEQUENCE: 22

His Arg Glu His Gln Lys Met Asp
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic peptide

<400> SEQUENCE: 23

Asp His Glu His Arg Lys Met Asp
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic peptide

<400> SEQUENCE: 24

Glu Arg Glu His Arg Lys Met Asp
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic peptide

<400> SEQUENCE: 25

His Arg Glu His Lys Lys Met Asp
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic peptide

<400> SEQUENCE: 26
```

```
Arg Asp Phe His Arg Lys Met Asp
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic peptide

<400> SEQUENCE: 27

Gln His Phe His Gln Lys Met Asp
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic peptide

<400> SEQUENCE: 28

Arg Asp Phe His Gln Lys Met Asp
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic peptide

<400> SEQUENCE: 29

Glu Lys Met His Gln Ile Met Gly
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic peptide

<400> SEQUENCE: 30

Asp Gln Met His Asp Ile Met Gly
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic peptide

<400> SEQUENCE: 31

Glu Gln Met His Asn Ile Met Gly
1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic peptide

<400> SEQUENCE: 32
```

His Arg Leu His Asp Arg Met Asp
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic peptide

<400> SEQUENCE: 33

Gln Lys Leu His Arg Arg Met Asp
1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic peptide

<400> SEQUENCE: 34

Gln Asp Phe His Asp Ile Met Ala
1               5

<210> SEQ ID NO 35
<211> LENGTH: 8
<212> TYPE: PRT
<213> ORGANISM: Artificial Sequence
<220> FEATURE:
<223> OTHER INFORMATION: Synthetic peptide

<400> SEQUENCE: 35

His Asp Phe His Asp Ile Met Ala
1               5

<210> SEQ ID NO 36
<211> LENGTH: 8
<212> TYPE: PRT
<213> ORGANISM: Artificial Sequence
<220> FEATURE:
<223> OTHER INFORMATION: Synthetic peptide

<400> SEQUENCE: 36

Glu Gln Leu Glu Lys Arg Met Asp
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic peptide

<400> SEQUENCE: 37

Gln His Val His Glu Lys Met Asp
1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic peptide

<400> SEQUENCE: 38

Gln His Asp His Gln Leu Met Asp

```
<210> SEQ ID NO 39
<211> LENGTH: 8
<212> TYPE: PRT
<213> ORGANISM: Artificial Sequence
<220> FEATURE:
<223> OTHER INFORMATION: Synthetic peptide

<400> SEQUENCE: 39

Arg Glu Trp Asp His Val Met Pro
1               5

<210> SEQ ID NO 40
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (7)..(7)
<223> OTHER INFORMATION: Xaa is MetO

<400> SEQUENCE: 40

His Gln Glu His Arg Lys Xaa Asp
1               5

<210> SEQ ID NO 41
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (7)..(7)
<223> OTHER INFORMATION: Xaa is MetO

<400> SEQUENCE: 41

Asp Gln Glu His Gln Lys Xaa Asp
1               5

<210> SEQ ID NO 42
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (7)..(7)
<223> OTHER INFORMATION: Xaa is MetO

<400> SEQUENCE: 42

Glu Asn Glu His Arg Lys Xaa Asp
1               5

<210> SEQ ID NO 43
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (7)..(7)
<223> OTHER INFORMATION: Xaa is MetO

<400> SEQUENCE: 43
```

```
Gln His Phe His Gln Lys Xaa Asp
1               5

<210> SEQ ID NO 44
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (7)..(7)
<223> OTHER INFORMATION: Xaa is MetO2

<400> SEQUENCE: 44

His Gln Glu His Arg Lys Xaa Asp
1               5

<210> SEQ ID NO 45
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (7)..(7)
<223> OTHER INFORMATION: Xaa is MetO2

<400> SEQUENCE: 45

Asp Gln Glu His Gln Lys Xaa Asp
1               5

<210> SEQ ID NO 46
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (7)..(7)
<223> OTHER INFORMATION: Xaa is MetO2

<400> SEQUENCE: 46

Gln His Phe His Gln Lys Xaa Asp
1               5

<210> SEQ ID NO 47
<211> LENGTH: 9
<212> TYPE: PRT
<213> ORGANISM: Artificial Sequence
<220> FEATURE:
<223> OTHER INFORMATION: Synthetic peptide

<400> SEQUENCE: 47

Asp Asn Leu Glu Lys Ile Met Asp Gln
1               5

<210> SEQ ID NO 48
<211> LENGTH: 9
<212> TYPE: PRT
<213> ORGANISM: Artificial Sequence
<220> FEATURE:
<223> OTHER INFORMATION: Synthetic peptide

<400> SEQUENCE: 48

Asn Asn Leu Glu Asn Ile Met Asp Asn
```

<210> SEQ ID NO 49
<211> LENGTH: 9
<212> TYPE: PRT
<213> ORGANISM: Artificial Sequence
<220> FEATURE:
<223> OTHER INFORMATION: Synthetic peptide

<400> SEQUENCE: 49

Asn Asn Ile Glu Asn Ile Met Pro Asn
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic peptide

<400> SEQUENCE: 50

Glu Asn Leu Glu Lys Ile Met Asp Gln
1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic peptide

<400> SEQUENCE: 51

Gln Gln Leu Glu Asn Ile Met Asp Asn
1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic peptide

<400> SEQUENCE: 52

Gln Asn Leu Glu Arg Ile Met Asp Gln
1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic peptide

<400> SEQUENCE: 53

Gln Asn Leu Glu Lys Ile Met Asp Gln
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic peptide

<400> SEQUENCE: 54

Gln Gln Leu Glu Asn Lys Met Glu Asn
1               5

```
<210> SEQ ID NO 55
<211> LENGTH: 9
<212> TYPE: PRT
<213> ORGANISM: Artificial Sequence
<220> FEATURE:
<223> OTHER INFORMATION: Synthetic peptide

<400> SEQUENCE: 55

Gln Glu Leu Glu Asn Ile Met Asp Asn
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic peptide

<400> SEQUENCE: 56

Gln Gln Leu Glu Lys Ile Met Asp Gln
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic peptide

<400> SEQUENCE: 57

Gln Gln Leu Glu His Ile Met Asp Gln
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic peptide

<400> SEQUENCE: 58

Glu Gln Leu Glu Lys Ile Met Asp Gln
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic peptide

<400> SEQUENCE: 59

Asn Asn Leu Glu Asn Ile Met Asp Gln
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic peptide

<400> SEQUENCE: 60

Asn Glu Leu Glu Asn His Met Asp Gln
1               5
```

<210> SEQ ID NO 61
<211> LENGTH: 9
<212> TYPE: PRT
<213> ORGANISM: Artificial Sequence
<220> FEATURE:
<223> OTHER INFORMATION: Synthetic peptide

<400> SEQUENCE: 61

Asn Asn Tyr Glu Asn Ile Met Asp Asn
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic peptide

<400> SEQUENCE: 62

Gln Asn Leu Glu His Ile Met Asp Gln
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic peptide

<400> SEQUENCE: 63

Gln Asn Trp Glu His Leu Met Asp Gln
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic peptide

<400> SEQUENCE: 64

Asn Asp Ile Lys His Met Met Glu Gln
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic peptide

<400> SEQUENCE: 65

Glu His Gln Glu His Arg Lys Met Asp
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic peptide

<400> SEQUENCE: 66

His Gln Glu His Arg Lys Met Asp Asn
1               5

```
<210> SEQ ID NO 67
<211> LENGTH: 9
<212> TYPE: PRT
<213> ORGANISM: Artificial Sequence
<220> FEATURE:
<223> OTHER INFORMATION: Synthetic peptide

<400> SEQUENCE: 67

Glu Asp Gln Glu His Gln Lys Met Asp
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic peptide

<400> SEQUENCE: 68

Asp Gln Glu His Gln Lys Met Asp Asn
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic peptide

<400> SEQUENCE: 69

Glu Gln His Phe His Gln Lys Met Asp
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic peptide

<400> SEQUENCE: 70

Gln His Phe His Gln Lys Met Asp Asn
1               5

<210> SEQ ID NO 71
<211> LENGTH: 9
<212> TYPE: PRT
<213> ORGANISM: Artificial Sequence
<220> FEATURE:
<223> OTHER INFORMATION: Synthetic peptide

<400> SEQUENCE: 71

Asp Glu Asn Glu His Arg Lys Met Asp
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic peptide

<400> SEQUENCE: 72

Glu Asn Glu His Arg Lys Met Asp Gln
1               5

<210> SEQ ID NO 73
```

```
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa is MetO

<400> SEQUENCE: 73

Asn Asn Leu Glu Asn Ile Xaa Asp Asn
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa is MetO

<400> SEQUENCE: 74

Gln Gln Leu Glu Asn Ile Xaa Asp Asn
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa is MetO

<400> SEQUENCE: 75

Gln Gln Leu Glu Lys Ile Xaa Asp Gln
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa is MetO

<400> SEQUENCE: 76

Asn Asn Leu Glu Asn Ile Xaa Asp Gln
1               5

<210> SEQ ID NO 77
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa is MetO

<400> SEQUENCE: 77
```

```
Gln Asn Leu Glu His Ile Xaa Asp Gln
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Xaa is MetO

<400> SEQUENCE: 78

Glu His Gln Glu His Arg Lys Xaa Asp
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa is MetO

<400> SEQUENCE: 79

Asp Gln Glu His Gln Lys Xaa Asp Asn
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa is MetO

<400> SEQUENCE: 80

Gln His Phe His Gln Lys Xaa Asp Asn
1               5

<210> SEQ ID NO 81
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa is MetO2

<400> SEQUENCE: 81

Asn Asn Leu Glu Asn Ile Xaa Asp Asn
1               5

<210> SEQ ID NO 82
<211> LENGTH: 9
<212> TYPE: PRT
<213> ORGANISM: Artificial Sequence
<220> FEATURE:
<223> OTHER INFORMATION: Synthetic peptide
```

```
<220> FEATURE:
<221> NAME/KEY: MISC_FEATURE
<222> LOCATION: (7)..(7)
<223> OTHER INFORMATION: Xaa is MetO2

<400> SEQUENCE: 82

Gln Gln Leu Glu Asn Ile Xaa Asp Asn
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa is MetO2

<400> SEQUENCE: 83

Asn Asn Leu Glu Asn Ile Xaa Asp Glu
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa is MetO2

<400> SEQUENCE: 84

Gln Asn Leu Glu His Ile Xaa Asp Gln
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Xaa is MetO2

<400> SEQUENCE: 85

Glu His Gln Glu His Arg Lys Xaa Asp
1               5

<210> SEQ ID NO 86
<211> LENGTH: 10
<212> TYPE: PRT
<213> ORGANISM: Artificial Sequence
<220> FEATURE:
<223> OTHER INFORMATION: Synthetic peptide

<400> SEQUENCE: 86

Asp Glu His Gln Glu His Arg Lys Met Asp
1               5                   10

<210> SEQ ID NO 87
<211> LENGTH: 10
<212> TYPE: PRT
<213> ORGANISM: Artificial Sequence
```

```
<220> FEATURE:
<223> OTHER INFORMATION: Synthetic peptide

<400> SEQUENCE: 87

His Gln Glu His Arg Lys Met Asp Asn Arg
1               5                   10

<210> SEQ ID NO 88
<211> LENGTH: 10
<212> TYPE: PRT
<213> ORGANISM: Artificial Sequence
<220> FEATURE:
<223> OTHER INFORMATION: Synthetic peptide

<400> SEQUENCE: 88

His Glu Asp Gln Glu His Gln Lys Met Asp
1               5                   10

<210> SEQ ID NO 89
<211> LENGTH: 10
<212> TYPE: PRT
<213> ORGANISM: Artificial Sequence
<220> FEATURE:
<223> OTHER INFORMATION: Synthetic peptide

<400> SEQUENCE: 89

Asp Gln Glu His Gln Lys Met Asp Asn Lys
1               5                   10

<210> SEQ ID NO 90
<211> LENGTH: 10
<212> TYPE: PRT
<213> ORGANISM: Artificial Sequence
<220> FEATURE:
<223> OTHER INFORMATION: Synthetic peptide

<400> SEQUENCE: 90

Asn Glu Gln His Phe His Gln Lys Met Asp
1               5                   10

<210> SEQ ID NO 91
<211> LENGTH: 10
<212> TYPE: PRT
<213> ORGANISM: Artificial Sequence
<220> FEATURE:
<223> OTHER INFORMATION: Synthetic peptide

<400> SEQUENCE: 91

Gln His Phe His Gln Lys Met Asp Asn Lys
1               5                   10

<210> SEQ ID NO 92
<211> LENGTH: 10
<212> TYPE: PRT
<213> ORGANISM: Artificial Sequence
<220> FEATURE:
<223> OTHER INFORMATION: Synthetic peptide

<400> SEQUENCE: 92

His Asn Asn Leu Glu Asn Ile Met Asp Asn
1               5                   10

<210> SEQ ID NO 93
<211> LENGTH: 10
<212> TYPE: PRT
<213> ORGANISM: Artificial Sequence
<220> FEATURE:
```

```
<223> OTHER INFORMATION: Synthetic peptide

<400> SEQUENCE: 93

Asn Asn Leu Glu Asn Ile Met Asp Asn Gln
1               5                   10

<210> SEQ ID NO 94
<211> LENGTH: 10
<212> TYPE: PRT
<213> ORGANISM: Artificial Sequence
<220> FEATURE:
<223> OTHER INFORMATION: Synthetic peptide

<400> SEQUENCE: 94

Asp Gln Gln Leu Glu Asn Ile Met Asp Asn
1               5                   10

<210> SEQ ID NO 95
<211> LENGTH: 10
<212> TYPE: PRT
<213> ORGANISM: Artificial Sequence
<220> FEATURE:
<223> OTHER INFORMATION: Synthetic peptide

<400> SEQUENCE: 95

Gln Gln Leu Glu Asn Ile Met Asp Asn Lys
1               5                   10

<210> SEQ ID NO 96
<211> LENGTH: 10
<212> TYPE: PRT
<213> ORGANISM: Artificial Sequence
<220> FEATURE:
<223> OTHER INFORMATION: Synthetic peptide

<400> SEQUENCE: 96

His Asn Asn Leu Glu Asn Ile Met Asp Gln
1               5                   10

<210> SEQ ID NO 97
<211> LENGTH: 10
<212> TYPE: PRT
<213> ORGANISM: Artificial Sequence
<220> FEATURE:
<223> OTHER INFORMATION: Synthetic peptide

<400> SEQUENCE: 97

Asn Asn Leu Glu Asn Ile Met Asp Gln Gln
1               5                   10

<210> SEQ ID NO 98
<211> LENGTH: 10
<212> TYPE: PRT
<213> ORGANISM: Artificial Sequence
<220> FEATURE:
<223> OTHER INFORMATION: Synthetic peptide

<400> SEQUENCE: 98

Lys Gln Asn Leu Glu His Ile Met Asp Gln
1               5                   10

<210> SEQ ID NO 99
<211> LENGTH: 10
<212> TYPE: PRT
<213> ORGANISM: Artificial Sequence
<220> FEATURE:
<223> OTHER INFORMATION: Synthetic peptide
```

<400> SEQUENCE: 99

Gln Asn Leu Glu His Ile Met Asp Gln Arg
1               5                   10

<210> SEQ ID NO 100
<211> LENGTH: 10
<212> TYPE: PRT
<213> ORGANISM: Artificial Sequence
<220> FEATURE:
<223> OTHER INFORMATION: Synthetic peptide

<400> SEQUENCE: 100

Glu Gln Gln Leu Glu His Ile Met Asp Gln
1               5                   10

<210> SEQ ID NO 101
<211> LENGTH: 10
<212> TYPE: PRT
<213> ORGANISM: Artificial Sequence
<220> FEATURE:
<223> OTHER INFORMATION: Synthetic peptide

<400> SEQUENCE: 101

Gln Gln Leu Glu His Ile Met Asp Gln Arg
1               5                   10

<210> SEQ ID NO 102
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: Xaa is MetO

<400> SEQUENCE: 102

Asp Glu His Gln Glu His Arg Lys Xaa Asp
1               5                   10

<210> SEQ ID NO 103
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa is MetO

<400> SEQUENCE: 103

Asp Gln Glu His Gln Lys Xaa Asp Asn Lys
1               5                   10

<210> SEQ ID NO 104
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: Xaa is MetO

<400> SEQUENCE: 104

Asn Glu Gln His Phe His Gln Lys Xaa Asp
1               5                   10

<210> SEQ ID NO 105
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Xaa is MetO

<400> SEQUENCE: 105

His Asn Asn Leu Glu Asn Ile Xaa Asp Asn
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa is MetO

<400> SEQUENCE: 106

Gln Gln Leu Glu Asn Ile Xaa Asp Asn Lys
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa is MetO

<400> SEQUENCE: 107

Asn Asn Leu Glu Asn Ile Xaa Asp Gln Gln
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Xaa is MetO

<400> SEQUENCE: 108

Lys Gln Asn Leu Glu His Ile Xaa Asp Gln
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Synthetic peptide

```
<220> FEATURE:
<221> NAME/KEY: MISC_FEATURE
<222> LOCATION: (8)..(8)
<223> OTHER INFORMATION: Xaa is MetO

<400> SEQUENCE: 109

Glu Gln Gln Leu Glu His Ile Xaa Asp Gln
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: Xaa is MetO2

<400> SEQUENCE: 110

Asp Glu His Gln Glu His Arg Lys Xaa Asp
1               5                   10

<210> SEQ ID NO 111
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Xaa is MetO2

<400> SEQUENCE: 111

His Asn Asn Leu Glu Asn Ile Xaa Asp Asn
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa is MetO2

<400> SEQUENCE: 112

Gln Gln Leu Glu Asn Ile Xaa Asp Asn Lys
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Xaa is MetO2

<400> SEQUENCE: 113

Lys Gln Asn Leu Glu His Ile Xaa Asp Gln
1               5                   10
```

<210> SEQ ID NO 114
<211> LENGTH: 11
<212> TYPE: PRT
<213> ORGANISM: Artificial Sequence
<220> FEATURE:
<223> OTHER INFORMATION: Synthetic peptide

<400> SEQUENCE: 114

His Asn Asn Leu Glu Asn Ile Met Asp Asn Arg
1               5                   10

<210> SEQ ID NO 115
<211> LENGTH: 11
<212> TYPE: PRT
<213> ORGANISM: Artificial Sequence
<220> FEATURE:
<223> OTHER INFORMATION: Synthetic peptide

<400> SEQUENCE: 115

Asn Asn Leu Glu Asn Ile Met Asp Asn Gln Gln
1               5                   10

<210> SEQ ID NO 116
<211> LENGTH: 11
<212> TYPE: PRT
<213> ORGANISM: Artificial Sequence
<220> FEATURE:
<223> OTHER INFORMATION: Synthetic peptide

<400> SEQUENCE: 116

Asp Gln Gln Leu Glu Asn Ile Met Asp Asn Arg
1               5                   10

<210> SEQ ID NO 117
<211> LENGTH: 11
<212> TYPE: PRT
<213> ORGANISM: Artificial Sequence
<220> FEATURE:
<223> OTHER INFORMATION: Synthetic peptide

<400> SEQUENCE: 117

Gln Gln Leu Glu Asn Ile Met Asp Asn Lys His
1               5                   10

<210> SEQ ID NO 118
<211> LENGTH: 11
<212> TYPE: PRT
<213> ORGANISM: Artificial Sequence
<220> FEATURE:
<223> OTHER INFORMATION: Synthetic peptide

<400> SEQUENCE: 118

His Asn Asn Leu Glu Asn Ile Met Asp Gln Arg
1               5                   10

<210> SEQ ID NO 119
<211> LENGTH: 11
<212> TYPE: PRT
<213> ORGANISM: Artificial Sequence
<220> FEATURE:
<223> OTHER INFORMATION: Synthetic peptide

<400> SEQUENCE: 119

Asn Asn Leu Glu Asn Ile Met Asp Gln Gln Arg
1               5                   10

<210> SEQ ID NO 120

<211> LENGTH: 11
<212> TYPE: PRT
<213> ORGANISM: Artificial Sequence
<220> FEATURE:
<223> OTHER INFORMATION: Synthetic peptide

<400> SEQUENCE: 120

Ala Lys Gln Asn Leu Glu His Ile Met Asp Gln
1               5                   10

<210> SEQ ID NO 121
<211> LENGTH: 11
<212> TYPE: PRT
<213> ORGANISM: Artificial Sequence
<220> FEATURE:
<223> OTHER INFORMATION: Synthetic peptide

<400> SEQUENCE: 121

Gln Asn Leu Glu His Ile Met Asp Gln Arg Lys
1               5                   10

<210> SEQ ID NO 122
<211> LENGTH: 11
<212> TYPE: PRT
<213> ORGANISM: Artificial Sequence
<220> FEATURE:
<223> OTHER INFORMATION: Synthetic peptide

<400> SEQUENCE: 122

Glu Gln Gln Leu Glu His Ile Met Asp Gln Arg
1               5                   10

<210> SEQ ID NO 123
<211> LENGTH: 11
<212> TYPE: PRT
<213> ORGANISM: Artificial Sequence
<220> FEATURE:
<223> OTHER INFORMATION: Synthetic peptide

<400> SEQUENCE: 123

Gln Gln Leu Glu His Ile Met Asp Gln Arg Lys
1               5                   10

<210> SEQ ID NO 124
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Xaa is MetO

<400> SEQUENCE: 124

His Asn Asn Leu Glu Asn Ile Xaa Asp Asn Arg
1               5                   10

<210> SEQ ID NO 125
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa is MetO

<400> SEQUENCE: 125

Gln Gln Leu Glu Asn Ile Xaa Asp Asn Lys His
1               5                   10

<210> SEQ ID NO 126
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa is MetO

<400> SEQUENCE: 126

Asn Asn Leu Glu Asn Ile Xaa Asp Gln Gln Arg
1               5                   10

<210> SEQ ID NO 127
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: Xaa is MetO

<400> SEQUENCE: 127

Ala Lys Gln Asn Leu Glu His Ile Xaa Asp Gln
1               5                   10

<210> SEQ ID NO 128
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Xaa is MetO

<400> SEQUENCE: 128

Glu Gln Gln Leu Glu His Ile Xaa Asp Gln Arg
1               5                   10

<210> SEQ ID NO 129
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (8)..(8)
<223> OTHER INFORMATION: Xaa is MetO2

<400> SEQUENCE: 129

His Asn Asn Leu Glu Asn Ile Xaa Asp Asn Arg
1               5                   10

<210> SEQ ID NO 130
<211> LENGTH: 11
<212> TYPE: PRT
<213> ORGANISM: Artificial Sequence
<220> FEATURE:

```
<223> OTHER INFORMATION: Synthetic peptide
<220> FEATURE:
<221> NAME/KEY: MISC_FEATURE
<222> LOCATION: (7)..(7)
<223> OTHER INFORMATION: Xaa is MetO2

<400> SEQUENCE: 130

Gln Gln Leu Glu Asn Ile Xaa Asp Asn Lys His
1               5                   10

<210> SEQ ID NO 131
<211> LENGTH: 11
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(9)
<223> OTHER INFORMATION: Xaa is MetO2

<400> SEQUENCE: 131

Ala Lys Gln Asn Leu Glu His Ile Xaa Asp Gln
1               5                   10
```

COMPOUNDS WHICH INHIBIT NEURONAL EXOCYTOSIS

This application claims the benefit of PCT/EP2013/057658, filed Apr. 12, 2013, and EP 12382146 4, filed Apr. 13, 2012, and U.S. Provisional Application Ser. No. 61/652,655, filed May 29, 2012, from which the PCT application claims priority, the disclosures of all of which are incorporated herein by reference in their entireties.

FIELD OF THE INVENTION

This invention refers to compounds capable of inhibiting neuronal exocytosis and cosmetic or pharmaceutical compositions which contain these compounds useful in the treatment of those conditions, disorders and/or diseases which require the inhibition of neuronal exocytosis, such as muscle spasticity, pain, inflammation, perspiration, facial asymmetry and/or facial wrinkles, preferably expression wrinkles.

BACKGROUND OF THE INVENTION

*Botulinum* toxins (also known as *botulinum* neurotoxins) are neurotoxins produced by the gram-positive bacteria *Clostridium botulinum*. They act by causing the paralysis of the muscles through the inhibition of the release of acetylcholine in the presynaptic axon terminal of the neuromuscular junction (synaptic transmission), thus preventing nerve transmission and muscle contraction. The paralyzing effects of the muscles of the botulinum toxin have been used both for therapeutic purposes as well as for cosmetic effects. The controlled administration of the botulinum toxin has been used for the treatment of a wide range of conditions, disorders and diseases, such as disorders and diseases of the urinary bladder (EP 2273976 A2), premature ejaculation (US 2011/052636 A1), priapism (U.S. Pat. No. 6,776,991 B2), ulcers and gastroesophageal reflux (U.S. Pat. No. 7,238,357 B2), disorders and diseases associated with hyper- and hypothyroidism (U.S. Pat. No. 6,740,321 B2), primary hyperparathyroid disorders and diseases (U.S. Pat. No. 6,974,793 B2), perspiration and hyperhidrosis (U.S. Pat. No. 6,974,578 B2 and U.S. Pat. No. 6,683,049 B2), inflammatory eye disorders and diseases (U.S. Pat. No. 7,465,457 B2 and U.S. Pat. No. 7,220,422 B2), strabismus (U.S. Pat. No. 6,841,156), otic disorders and diseases (U.S. Pat. No. 6,265,379 B2 and U.S. Pat. No. 6,358,926 B2), excess cerumen secretion (US 2010/028385), neuropsychiatric disorders and diseases such as Alzheimer's, anxiety, schizophrenia, mania, depression (U.S. Pat. No. 7,911,587 B2), different compulsive disorders and diseases such as obsessions, compulsive skin picking, Tourette's syndrome, trichotillomania (U.S. Pat. No. 7,393,537 B2), cerebral paralysis (U.S. Pat. No. 6,939,852 B2), gonadotropin-related disorders and diseases (WO 02/074327), different cancers (U.S. Pat. No. 6,139,845 B2, U.S. Pat. No. 7,838,007 B2), neoplasms (U.S. Pat. No. 7,709,440 B2), different types of pain including headaches, migraines, fibromyalgia, arthritis or neuropathic pain among others (US 2010/266638, U.S. Pat. No. 7,811,586 B2, U.S. Pat. No. 7,704,524 B2, U.S. Pat. No. 7,704,511 B2, U.S. Pat. No. 7,468,189 B2, U.S. Pat. No. 7,255,866 B2, U.S. Pat. No. 7,091,176 B2, U.S. Pat. No. 6,997,476 B2, U.S. Pat. No. 6,869,610 B2, U.S. Pat. No. 6,838,434 B2, U.S. Pat. No. 6,641,820 B2, U.S. Pat. No. 6,623,742 B2, U.S. Pat. No. 6,565,870 B1, U.S. Pat. No. 6,500,436 B1, U.S. Pat. No. 6,458,365 B1, U.S. Pat. No. 6,423,319 B1, U.S. Pat. No. 6,113,915 A and U.S. Pat. No. 5,714,468 A), neurogenic inflammation (U.S. Pat. No. 6,063,768 B2), different disorders and diseases of the autonomic nervous system such as otitis and sinusoidal disorders (U.S. Pat. No. 5,766,605 A), disorders and diseases of the smooth muscle (U.S. Pat. No. 5,437,291 A), nerve impingements (US 2003/0224019), epilepsy (U.S. Pat. No. 7,357,934 B2), dystonia U.S. Pat. No. 6,872,397 B2), trembling (U.S. Pat. No. 6,861,058 B2), Parkinson's disease (U.S. Pat. No. 6,620,415 B2), dizziness (U.S. Pat. No. 7,270,287 B2), osteoporosis (WO 2011/038015), different disorders and diseases of the skin such as calluses, warts, ulcers and lesions on the skin (U.S. Pat. No. 8,048,423 B2, US 2011/206731), psoriasis and dermatitis (U.S. Pat. No. 5,670,484 A), vascular hyperreactivity and rosacea (WO 2010/114828), acne (WO 03/011333), hair growth and maintenance (U.S. Pat. No. 6,299,893 B1), facial wrinkles (U.S. Pat. No. 7,255,865 B2), ptosis of the eyebrows and forehead (US 2011/280978) or drooping mouth corners (U.S. Pat. No. 6,358,917 B1) among others.

However, the toxicity inherent in botulinum toxin causes its administration, in a wide range of doses, to result in undesired secondary effects, such as immunogenic responses, cephalalgias, nausea, paralysis or muscle weakness, respiratory failure, and in more extreme cases even the death of the subject treated [*FDA News*, Feb. 8, 2008, "*FDA Notifies Public of Adverse Reactions Linked to Botox Use*": Coté, T. R. et al. "*Botulinum toxin type A injections: Adverse events reported to the US Food and Drug Administration in therapeutic and cosmetic cases*" *J. Amer. Acad. Derm.* 2005, 53(3), 407-415]. These severe secondary effects, together with the high cost of the treatment, seriously limits the application of botulinum toxin with therapeutic or cosmetic purposes, being relegated to chronic applications and/or diseases for which there is no suitable treatment. There is, therefore, a pressing need to develop molecules which imitate the paralyzing effects of *botulinum* toxins but which are equipped with much simpler and more stable molecular structures that do not induce immune reactions, and whose cost of production is affordable. Molecules of a peptide nature comply with these properties.

At a molecular level, *botulinum* toxins are proteases which degrade neuronal proteins that are involved in the exocytosis mechanism activated by the calcium ion [Schiavo G. et al. "*Bases Moleculares del tétanos y del botulismo*" *Investigación y Ciencia* 1996, 234, 46-55; Montecucco B. and Schiavo G. "*Mechanism of action of tetanus and botulinum neurotoxins*" *Mol. Microbiol.* 1994, 13, 1-8; Schiavo g. et al. "*Tetanus and botulinum neurotoxins are zinc proteases specific for components of the neuroexocytosis apparatus*" *Ann. NY Acad. Sci.* 1994, 710, 65-75]. For example, botulinum toxin A, the most commonly used in clinics to treat the symptomatology of spasmodic diseases and in cosmetics due to its applications in the elimination of facial wrinkles and facial asymmetry, breaks down the neuronal protein SNAP-25. This protein SNAP-25 plays a key role in neurosecretion since it is involved in the formation of a protein complex (known by the name of SNARE or fusion complex) which manages and controls the release of acetylcholine accumulated in vesicles. The nucleus of this fusion complex is comprised of the proteins SNAP-25 and syntaxin, located in the presynaptic plasma membrane, and the synaptobrevin protein of the VAMP family of proteins, located in the vesicular plasma membrane [Calakos N. and Scheller R. H. "*Synaptic vesicle biogenesis, docking and fusion: a molecular description*" *Physiol. Rev.* 1996, 76, 1-29; Sutton R. B. et al. "*Crystal structure of a SNARE complex involved in a synaptic exocytosis at* 2.4 Å *resolu-* tion" *Nature* 1998, 395, 347-353]. The principal function of the fusion complex is to bring the neurotransmitter (acetychloine) loaded vesicle closer to and place it in contact with the presynaptic plasma membrane [Calakos N. and Scheller R. H. "*Synaptic vesicle biogeneis, docking and fusion: a molecular description*" *Physiol. Rev.* 1996, 76, 1-29; Sutton R. B. et al. "*Crystal structure of a SNARE complex involved in synaptic exocytosis at 2.4 Å resolution*" *Nature* 1998, 395, 347-353]. In this way, in response to an increase in the concentration of calcium, the fusion of both plasma membranes will be favored, thus producing the release of the neurotransmitter. Therefore, this vesicle docking and fusion protein SNARE complex constitutes a key target for controlling neurosecretion. The truncation of any of the proteins which form the fusion complex prevents their assembling and, therefore, inhibits vesicle release and inhibits neuronal exocytosis.

It is known in the prior art that certain peptides derived from the protein sequences which form the SNARE complex are capable of inhibiting neuronal exocytosis, such as peptides derived from the amino and carboxy-terminal domains of the protein SNAP-25 [Apland J. P. et al, "*Peptides that mimic the carboxy-terminal domain of SNAP-25 block acetylcholine release at an aplysia synapse*" *J. Appl. Toxicol.* 1999, 19, Suppl, 1: S23-S26; Mehta P. P. et al. "*SNAP-25 and synaptotagmin involvement in the final $Ca^{2+}$-dependent triggering of neurotransmitter exocytosis*" *Proc. Natl. Acad. Sci. USA* 1996, 93, 10471-10476; Ferrer-Montiel A. V. et al. "*The 26-mer peptide released from cleavage by botulinum neurotoxin E inhibits vesicle docking*" *FEBS Lett.* 1998, 435, 84-88; Guiterrez L. M. et al. "*A peptide that mimics the carboxy-terminal domain of SNAP-25 blocks $C^{2+}$-dependent exocytosis in chromattin cells*" *FEBS Lett.* 1995, 372, 39-43; Gutierrez L. M. et al. "*A peptide that mimics the C-terminal sequence of SNAP-25 inhibits secretory vesicle docking in chromattin cells*" *J. Biol. Chem.* 1997, 272, 2634-2639; Blanes-Mira C et al. "*Small peptides patterned after the N-terminus domain of SNAP-25 inhibit SNARE complex assembly and regulated exocytosis*" *J. Neurochem,* 2004, 88, 124-135], the peptides derived from the sequence of syntaxin amino acids [Martin F. et al. "*Inhibition of insulin release by synthetic peptides show that the H3 region at the C-terminal domain of syntaxin-1 is crucial for $Ca^{2+}$-but not for guanosine 5'-[gammathio]thriphosphate-induced secretion*" *Biochem. J.* 1996, 320, 201-205], of the synaptobrevin [Cornille F. "*Inhibition of neurotransmitter release by synthetic prolinerich peptides shows that the N-terminal domain of vesicle-associated membrane protein/synaptobrevin is critical for neuro-exocytosis*" *J. Biol. Chem.* 1995, 270, 16826-16830], of the synaptotagmin [Mehta P. P. et al. "*SNAP-25 and synaptotagmin involvement in the final $Ca^{2+}$-dependent triggering of neurotransmitter exocytosis*" *Proc. Natl. Acad. Sci. USA* 1996, 93, 10471-10476] and of the protein snapin [Ilardi J. M. et al. "*Snapin: A SNARE associated protein implicated in synaptic transmission*" *Nat. Neurosci.* 1999, 2, 119-124]. Similarly, synthetic peptides obtained by rational design or by searching synthetic libraries which are capable of inhibiting neuronal exocytosis by interfering in the formation of the SNARE complex have also been described [Blanes-Mira C. et al. "*Identification of SNARE complex modulators that inhibit exocytosis form an α-helixconstrained combinatorial library*" *Biochem J.* 2003, 375, 159-166].

The industrial application of this type of compounds has been limited. The document EP 2318033 A2 describes the use of peptides derived from SNAP-25 for the treatment of pain and inflammation, and the document EP 1856139 A2 describes the use of peptides derived from SNAP-25 chemically modified to increase their bioavailability for the treatment of different diseases for which the treatment with botulinum toxin has shown effectiveness, among them the treatment of hyperhidrosis. Similarly, the cosmetic industry has made significant efforts to develop compounds which imitate the action of *botulinum* toxins with use in the treatment and prevention of the formation of expression wrinkles [Blanes-Mira C. et al. "*A synthetic hexapeptide (Argireline®) with anti-wrinkle activity*" *Int. J. Cosmetic Sci.* 2002, 24, 303-310]. In particular, peptides derived from the amino terminal fragment of the protein SNAP-25 which have anti-wrinkle effects are described in the documents EP 1180524 A1 and EP 2123673 A1, international application WO 97/34620 also describes peptides derived from the sequence of amino acids of the protein SNAP-25, in particular from its carboxy-terminal region, or from the synaptobrevin or the syntaxin capable of inhibiting neuronal exocytosis, and international application WO 2011/048443 describes peptides derived from the subunit c of the membrane component of V-ATPase capable of inhibiting neuronal exocytosis through its bonding to synaptobrevin and its potential application as anti-wrinkle treatment.

Thus, this invention provides an alternative to the existing needs and comprises the discovery of peptide sequences not derived from the protein SNAP-25 which are capable of inhibiting neuronal exocytosis.

DESCRIPTION OF THE INVENTION

This invention provides an alternative to the abovementioned problem. Surprisingly, the authors of this invention have found that neuronal exocytosis can be inhibited by certain compounds not derived from the protein SNAP-25 and which are an alternative to the existing compounds in the prior art. These compounds are useful for the treatment and/or care of conditions, disorders and/or diseases which improve or are prevented by the inhibition of neuronal exocytosis.

Definitions

In order to facilitate the comprehension of this invention, the meanings of some terms and expressions as they are used in the context of the invention are included.

In the context of this invention "skin" is understood as the layers which comprise it, from the uppermost layer or stratum corneum to the lowermost layer or hypodermis, both inclusive. These layers are composed of different types of cells such as keratinocytes, fibroblasts, melanocytes, mastocytes, neurones and/or adipocytes, among others. The term "skin" also comprises the scalp.

The term "treatment", as used in the context of this specification when it is not accompanied by the qualifications "cosmetic, non-therapeutic", means the administration of a compound according to the invention to alleviate or eliminate a disease or disorder or reduce or eliminate one or more symptoms associated with is disease or disorder. The term "treatment" also covers the ability to alleviate or eliminate the physiological consequences of the disease or disorder.

When the term "treatment" is accompanied by the qualifications "cosmetic, non-therapeutic" they refer to the application of the compound to the skin, hair and/or mucous membranes in particular with the aim of improving the cosmetic qualities of the skin, hair and/or mucous membranes such as and not restricted to, their level of hydration, elasticity, firmness, shine, tone or texture, among others. The term "care" in this invention refers to the maintenance of the qualities of the skin, hair and/or mucous membranes. These qualities are subject to improvement and maintained through a cosmetic treatment and/or care of the skin, hair and/or mucous membranes both in healthy subjects as well as those which present diseases and/or disorders of the skin and/or mucous membranes, such as and not restricted to, ulcers and lesions on the skin, psoriasis, dermatitis, acne or rosacea, among others.

The term "prevention", as used in this invention, refers to the ability of a compound of the invention to prevent the appearance or development of a disease or disorder before its appearance.

In the context of this invention, the term "aging" refers to the changes experience by the skin with age (chronoaging) or through exposure to the sun (photoaging) or to extreme environmental climatic conditions of cold or wind, chemical contaminants or pollutants, and includes all the external visible and/or perceptible changes through touch, such as and not restricted to, the development of discontinuities on the skin such as wrinkles, fine lines, expression lines, stretch marks, furrows, irregularities or roughness, increase in the size of pores, loss of hydration, loss of elasticity, loss of firmness, loss of smoothness, loss of the capacity to recover from deformation, loss of resilience, sagging of the skin such as sagging cheeks, the appearance of bags under the eyes or the appearance of a double chin, among others, changes to the color of the skin such as marks, reddening, bags or the appearance of hyperpigmented areas such as age spots or freckles among others, anomalous differentiation, hyperkeratinization, elastosis, keratosis, hair loss, orange peel skin, loss of collagen structure and other histological changes of the stratum corneum, of the dermis, epidermis, vascular system (for example the appearance of spider veins or telangiectasias) or of those tissues close to the skin, among others. The term "photoaging" groups together the set of processes due to the prolonged exposure of the skin to ultraviolet radiation which result in the premature aging of the skin, and it presents the same physical characteristics as aging, such as and not restricted to, flaccidity, sagging, changes to the color or irregularities in the pigmentation, abnormal and/or excessive keratinization. The sum of several environmental factors such as exposure to tobacco smoke, exposure to pollution, and climatic conditions such as cold and/or wind also contributes to the aging of the skin.

In this description the abbreviations used for amino acids follow the recommendations of the 1983 IUPAC-IUB Commission of Biochemical Nomenclature specified in *Eur. J. Biochem.* (1984), 138, 937.

Thus, for example, Phe represents $NH_2$—$CH(CH_2$—$C_5H_6)$—COOH, Phe- represents $NH_2$—$CH(CH_2$—$C_5H_6)$—CO—, -Phe represents —NH—$CH(CH_2$—$C_6H_8)$—CO—. Therefore, the hyphen, which represents the peptide bond, eliminates the OH in the 1-carboxyl group of the amino acid (represented here in the conventional non-ionized form) when situated to the right of the symbol, and eliminates the H of the 2-amino group of the amino acid when situated to the left of the symbol; both modifications can be applied to the same symbol (see Table 1).

TABLE 1

Structures of the amino acid residues and their nomenclature in one and three-letter code

| Name | Residue | Symbol | Residue |
|---|---|---|---|
| Asparaginyl -Asn- N | [structure] | Glutaminyl -Gln- Q | [structure] |
| Histidyl -His- H | [structure] | Arginyl -Arg- R | [structure] |

TABLE 1-continued

Structures of the amino acid residues and their nomenclature in one and three-letter code

| Name | Residue | Symbol | Residue |
|---|---|---|---|
| Lysyl -Lys- K | | Tryptophyl -Trp- W | |
| Tyrosyl -Tyr- Y | | Phenylalanyl -Phe- F | |
| Leucyl -Leu- L | | Methionyl -Met- M | |
| Valyl -Val- V | | Isoleucyl -Ile- I | |
| Glutamyl -Glu- E | | Aspartyl -Asp- D | |
| Prolyl -Pro- P | | Glycyl -Gly- G | |
| Alanyl -Ala- A | | Methionyl (sulfoxide) -MetO— | |

TABLE 1-continued

Structures of the amino acid residues and their nomenclature in one and three-letter code

| Name | Residue | Symbol | Residue |
|---|---|---|---|
| Methionyl (sulfone) -MetO$_2$- | | | |

The abbreviation "-MetO-" is used in this invention to designate the amino acid residue methionyl(sulfoxide). The amino acid residue methionyl(sulfoxide) can be incorporated into the compounds of the invention using the commercial amino acid methionine(sulfoxide) or can be obtained in situ in the compounds of the invention by oxidation of the methionyl residue.

The abbreviation "-MetO$_2$-" is used in this invention to designate the amino acid residue methionyl(sulfone). The amino acid residue methionyl(sulfone) can be incorporated into the compounds of the invention using the commercial amino acid methionine(sulfone) or can be obtained in situ in the compounds of the invention by oxidation of the methionyl residue or the methionyl(sulfoxide) residue.

The abbreviation "Ac-" is used in this description to designate the acetyl group (CH$_3$—CO—), the abbreviation "Palm-" is used to designate the palmitoyl group (CH$_3$—(CH$_2$)$_{14}$—CO—) and the abbreviation "Myr-" is used to designate the myristoyl group (CH$_3$—(CH$_2$)$_{12}$—CO—).

The term "non-cyclic aliphatic group" is used in this invention to cover alkyl, alkenyl and alkynyl groups, linear or branched.

The term "alkyl group" refers to a linear or branched saturated group which has between 1 and 24, preferably between 1 and 16, more preferably between 1 and 14, even more preferably between 1 and 12, yet more preferably 1, 2, 3, 4, 5 or 6 carbon atoms and is bound to the rest of the molecule by a simple bond, including, for example and not restricted to, methyl, ethyl, isopropyl, isobutyl, tert-butyl, heptyl, octyl, decyl, dodecyl, lauryl, hexadecyl, octadecyl, amyl, 2-ethylhexyl, 2-methylbutyl, 5-methylhexyl and similar.

The term "alkenyl group" refers to a group, linear or branched, which has between 2 and 24, preferably between 2 and 16, more preferably between 2 and 14, even more preferably between 2 and 12, yet more preferably 2, 3, 4, 5 or 6 carbon atoms, with one or more double carbon-carbon bonds, preferably with 1, 2 or 3 double carbon-carbon bonds, conjugated or unconjugated, which is bound to the rest of the molecule by a simple bond, including, for example and not restricted to, the vinyl group (—CH$_2$=CH$_2$), allyl(—CH$_2$—CH=CH$_2$), oleyl, linoleyl and similar.

The term "alkynyl group" refers to a group, linear or branched, which has between 2 and 24, preferably between 2 and 16, more preferably between 2 and 14, even more preferably between 2 and 12, yet more preferably 2, 3, 4, 5 or 6 carbon atoms, with one or more triple carbon-carbon bonds, preferably 1, 2 or 3 triple carbon-carbon bonds, conjugated or unconjugated, which is bound to the rest of the molecule by a simple bond, including, for example and not restricted to, the ethynyl group, 1-propynyl, 2-propynyl, 1-butynyl, 2-butynyl, 3-butynyl, pentynyl, such as 1-pentynyl, and similar. The alkynyl groups can also contain one or more double carbon-carbon bonds, including for example and not restricted to, the group but-1-en-3-ynyl, pent-4-en-1-ynyl and similar.

The term "alycyclic group" is sued in this invention to cover, for example and not restricted to, cycloalkyl or cycloalkenyl or cycloalkynyl groups.

The term "cycloalkyl" refers to a saturated mono- or polycyclic aliphatic group which has between 3 and 24, preferably between 3 and 16, more preferably between 3 and 14, even more preferably between 3 and 12, yet more preferably 3, 4, 5 or 6 carbon atoms and is bound to the rest of the molecule by a simple bond, including, for example and not restricted to, cyclopropyl, cyclobutyl, cyclopentyl, cyclohexyl, cycloheptyl, methyl cyclohexyl, dimethyl cyclohexyl, octahydroindene, decahydronaphthalene, dodecahydrophenalene and similar.

The term "cycloalkenyl" refers to a non-aromatic mono- or polycyclic aliphatic group which has between 5 and 24, preferably between 5 and 16, more preferably between 5 and 14, even more preferably between 5 and 12, yet more preferably 5 or 6 carbon atoms, with one or more double carbon-carbon bonds, preferably 1, 2 or 3 double carbon-carbon bonds, conjugated or unconjugated, bound to the rest of the molecule by a simple bond, including, for example and not restricted to, the cyclopent-1-en-1-yl group and similar.

The term "cycloalkynyl" refers to a non-aromatic mono- or polycyclic aliphatic group which has between 8 and 24, preferably between 8 and 16, more preferably between 8 and 14, even more preferably between 8 and 12, yet more preferably 8 or 9 carbon atoms, with one or more triple carbon-carbon bonds, preferably 1, 2 or 3 triple carbon-carbon bonds, conjugated or unconjugated, bound to the rest of the molecule by a simple bond, including, for example and not restricted to, the cyclooct-2-in-1-yl group and similar. The cycloalkynyl groups can also contain one or more double carbon-carbon bonds, including for example and not restricted to, the cyclooct-4-en-2-ynyl group and similar.

The term "aryl group" refers to an aromatic group which has between 6 and 30, preferably between 6 and 18, more preferably between 6 and 10, even more preferably between 6 or 10 carbon atoms, which comprises 1, 2, 3 or 4 aromatic rings, bound by a carbon-carbon bond or condensed, including, for example and not restricted to, phenyl, naphthyl, diphenyl, indenyl, phenanthryl or anthranyl, among others; or an aralkyl group.

The term "aralkyl group" refers to an alkyl group substituted by an aromatic group, with between 7 and 24 carbon atoms and including, for example and not restricted to, —$(CH_2)_{1-6}$-phenyl, —$(CH_2)_{1-6}$-(1-naphthyl), —$(CH_2)_{1-6}$-(2-naphthyl), —$(CH_2)_{1-6}$—$CH(phenyl)_2$ and similar.

The term "heterocyclyl group" refers to a hydrocarbonated ring of 3-10 members, in which one or more of the atoms in the ring, preferably 1, 2 or 3 of the atoms in the ring, is a different element to carbon, such as nitrogen, oxygen or sulfur and can be saturated or unsaturated. For the purposes of this invention, the heterocycle can be a monocyclic, bicyclic or tricyclic system, which can include systems of condensed rings; and the nitrogen, carbon or sulfur atoms can optionally be oxidized in the radical heterocycle; the nitrogen atom can optionally be quaternized; and the radical heterocyclyl can be partially or completely saturated or aromatic. The greatest preference is for the term heterocyclyl to refer to a ring of 5 or 6 members. Examples of saturated heterocyclic groups are dioxane, piperidine, piperazine, pyrrolidine, morpholine and thiomorpholine. Examples of aromatic heterocyclic groups, also known as heteroaromatic groups are pyridine, pyrrol, furan, thiophene, benzofuran, imidazoline, quinolein, quinoline, pyridazine and naphthyridine.

The term "heteroarylalkyl group" refers to an alkyl group substituted by a substituted or unsubstituted aromatic heterocyclyl group, the alkyl group having from 1 to 6 carbon atoms and the aromatic heterocyclyl group between 2 and 24 carbon atoms and from 1 to 3 atoms other than carbon and including, for example and not restricted to, —$(CH_2)_{1-6}$-imidazolyl, —$(CH_2)_{1-6}$-triazolyl, —$(CH_2)_{1-6}$-thienyl, —$(CH_2)_{1-6}$-furyl, —$(CH_2)_{1-6}$-pyrrolidinyl and similar.

As is understood in this technical field, there can be a certain level of substitution of the aforementioned groups. Therefore, there can be substitution in any of the groups of this invention where specifically stated. The references in this document to substituted groups in the groups of this invention indicate that the specified radical can be substituted in one or more positions available by one or more substituents, preferably in 1, 2 or 3 positions, more preferably in 1 or 2 positions, yet more preferably in 1 position. These substituents include, alkyl $C_1$-$C_4$; hydroxyl; alcoxyl $C_1$-$C_4$; amino; aminoalkyl $C_1$-$C_4$; carbonyloxyl $C_1$-$C_4$; oxycarbonyl $C_1$-$C_4$; halogen such as fluoride, chlorine, bromine and iodine; cyano; nitro; azide; alkylsulfonyl $C_1$-$C_4$; thiol; alkylthio $C_1$-$C_4$; aryloxyl such as phenoxyl; —$NR_b$($C$=$NR_c$)$NR_bR_c$; wherein $R_b$ and $R_c$ are independently selected from the group formed by H, alkyl $C_1$-$C_4$, alkenyl $C_2$-$C_4$, alkynyl $C_2$-$C_4$, cycloalkyl $C_3$-$C_{10}$, aryl $C_6$-$C_{18}$, aralkyl $C_7$-$C_{17}$, heterocyclyl or 3-10 members or protective group of the amino group.

Compounds in the Invention

A first aspect of the invention refers to a compound of general formula (I):

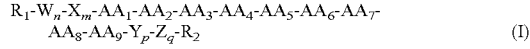

$R_1$-$W_n$-$X_m$-$AA_1$-$AA_2$-$AA_3$-$AA_4$-$AA_5$-$AA_6$-$AA_7$-$AA_8$-$AA_9$-$Y_p$-$Z_q$-$R_2$     (I)

its stereoisomers, mixtures thereof and/or its cosmetically or pharmaceutically acceptable salts, characterized in that:

$AA_1$ is selected from the group formed by -Arg-, -His-, -Lys-, -Gln-, -Asn-, -Glu- and -Asp-;
$AA_2$ is selected from the group formed by -Arg-, -His-, -Lys-, -Gln-, -Asn-, -Glu- and -Asp-;
$AA_3$ is selected from the group formed by -Leu-, -Ile-, -Val-, -Met-, -MetO-, -MetO$_2$-, -Glu-, -Asp-, -Phe-, -Trp- and -Tyr-;
$AA_4$ is selected from the group formed by -Lys-, -His-, -Glu-, and -Asp-;
$AA_5$ is selected from the group formed by -Arg-, -His-, -Lys-, -Gln-, -Asn-, -Glu- and -Asp-;
$AA_6$ is selected from the group formed by -Met-, -MetO-, -MetO$_2$-, -Ile-, -Leu-, -Val-, -His-, -Lys- and -Arg-;
$AA_7$ is selected from the group formed by -Met-, -MetO-, and -MetO$_2$-;
$AA_8$ is selected from the group formed by -Glu-, -Asp-, -Gly-, -Ala-, and -Pro-;
$AA_9$ is selected from the group formed by -Gln-, -Asn- or a bond;
W, X, Y, Z are amino acids and are independently selected from amongst themselves;
n, m, p and q are independently selected from amongst themselves and have a value of 0 or 1;
n+m+p+q is smaller or equal to 2;
with the condition that if $AA_1$ is -Arg-, $AA_2$ is -Gln-, $AA_3$ is -Leu-, $AA_4$ is -Glu-, $AA_5$ is -His-, $AA_6$ is -Val- and $AA_9$ is a bond, then $AA_8$ is selected from the group formed by -Glu-, -Gly-, -Ala- and -Pro-;
and with the condition that if X is -Asn-, $AA_1$ is -Lys-, $AA_2$ is -Arg-, $AA_3$ is -Phe-, $AA_4$ is -His-, $AA_5$ is -Asn-, $AA_6$ is -Ile-, $AA_8$ is -Gly- and $AA_9$ is a bond, n is 0, then Y or Z are not -Arg-;
$R_1$ is selected from the group formed by H, a polymer derived from polyethylene glycol, a non-cyclic substituted or unsubstituted aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group formed by H, a non-cyclic substituted or unsubstituted aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;
$R_2$ is selected from the group formed by —$NR_3R_4$, —$OR_3$ and —$SR_3$ wherein $R_3$ and $R_4$ are independently selected from the group formed by H, a polymer derived from polyethylene glycol, a non-cyclic substituted or unsubstituted aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and
$R_1$ and $R_2$ are not α-amino acids.

Groups $R_1$ and $R_2$ are bound to the amino-terminal (N-terminal) and carboxy-terminal (C-terminal) ends of the peptide sequences respectively.

In accordance with a preferred embodiment of this invention $R_1$ is selected from the group formed by H, a polymer derived from polyethylene glycol and $R_5$—CO—, wherein $R_5$ is selected from the group formed by substituted or unsubstituted alkyl radical $C_1$-$C_{24}$, substituted or unsubstituted alkenyl $C_2$-$C_{24}$, substituted or unsubstituted alkynyl $C_2$-$C_{24}$, substituted or unsubstituted cycloalkyl $C_3$-$C_{24}$, substituted or unsubstituted cycloalkenyl $C_5$-$C_{24}$, substituted or unsubstituted cycloalkynyl $C_8$-$C_{24}$, substituted or unsubstituted aryl $C_6$-$C_{30}$, substituted or unsubstituted aralkyl $C_7$-$C_{24}$, substituted or unsubstituted heterocyclyl ring of 3-10 members, and substituted or unsubstituted heteroarylalkyl of 2 to 24 carbon atoms and 1 to 3 atoms other than carbon and an alkyl chain of 1 to 6 carbon atoms and $R_5$—CO— is not an α-amino acid. More preferably, $R_1$ is selected from the group formed by H, a polymer derived from polyethylene glycol with a molecular weight comprised between 200 and 35000 Daltons, acetyl, tert-butanoyl, prenyl, hexanoyl, 2-methylhexanoyl, cyclohexanecarboxyl, octanoyl, decanoyl, lauroyl, myristoyl, palmitoyl, stearoyl, oleoyl and linoleoyl. Even more preferably, $R_1$ is H, acetyl, lauroyl, myristoyl or palmitoyl. In an even more preferred embodiment, $R_1$ is acetyl or palmitoyl.

In accordance with another preferred embodiment, $R_2$ is selected from the group formed by —$R_3R_4$, —$OR_3$, —$SR_3$, wherein $R_3$ and $R_4$ are independently selected from the group formed by H, a polymer derived from polyethylene glycol, substituted or unsubstituted alkyl $C_1$-$C_{24}$, substituted or unsubstituted alkenyl $C_2$-$C_{24}$, substituted or unsubstituted alkynyl $C_2$-$C_{24}$, substituted or unsubstituted cycloalkyl $C_3$-$C_{24}$, substituted or unsubstituted cycloalkenyl $C_5$-$C_{24}$, substituted or unsubstituted cycloalkynyl $C_8$-$C_{24}$, substituted or unsubstituted aryl $C_6$-$C_{30}$, substituted or unsubstituted aralkyl $C_7$-$C_{24}$, substituted or unsubstituted heterocyclyl ring of 3-10 members, and substituted or unsubstituted heteroarylalkyl of 2 to 24 carbon atoms and 1 to 3 atoms other than carbon wherein the alkyl chain is of 1 to 6 carbon atoms and —$NR_3R_4$ is not an α-amino acid. Optionally, $R_3$ and $R_4$ can be bound by a saturated or unsaturated carbon-carbon bond, forming a cycle with the nitrogen atom. More preferably $R_2$ is —$NR_3R_4$ or —$OR_3$. More preferably, $R_3$ and $R_4$ are independently selected from the group formed by H, a polymer derived from polyethylene glycol with a molecular weight comprised between 200 and 35000 Daltons, methyl, ethyl, hexyl, dodecyl, or hexadecyl. Even more preferably $R_3$ and $R_4$ are independently selected from H, methyl, ethyl, hexyl, dodecyl and hexadecyl and still more preferably $R_3$ is H and $R_4$ is selected from the group formed by H, methyl, ethyl, hexyl, dodecyl, and hexadecyl. In accordance with an even more preferred embodiment, $R_2$ is selected from —OH and —$NH_2$.

In accordance with another embodiment of this invention $R_1$ is selected from the group formed by H, acetyl, lauroyl, myristoyl or palmitoyl, preferably $R_1$ is selected from the group formed by H, acetyl and palmitoyl and $R_2$ is selected from the group formed by —OH and —$NH_2$.

In accordance with another particular embodiment the most preferred structures of the polymer derived from polyethylene glycol are the group (—$CH_2$—$CH_2$—O)$_r$—H in which r is a number comprised between 4 and 795 and the group

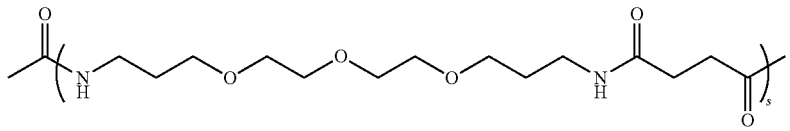

where s is a number between 1 and 125.

In accordance with another embodiment of this invention n, m, p and q are 0.

In accordance with another embodiment of this invention $AA_1$ is selected from the group formed by -Arg-, -His-, -Lys-, -Gln-, -Asn-, -Glu- and -Asp-, $AA_2$ is selected from the group formed by -Arg-, -His-, -Lys-, -Gln-, -Asn-, and -Asp-, $AA_3$ is selected from the group formed by -Leu-, -Met-, -MetO-, -MetO$_2$-, -Glu- and -Phe-, $AA_4$ is selected from the group formed by -His- and -Glu-, $AA_5$ is selected from the group formed by -Arg-, -His-, -Lys-, -Gln-, -Asn- and -Asp-, $AA_6$ is selected from the group formed by -Ile-, -Lys-, and -Arg-, $AA_7$ is selected from the group formed by -Met-, -MetO-, and -MetO$_2$-, $AA_8$ is selected from the group formed by -Asp-, -Gly- and -Ala-, $AA_9$ is selected from the group formed by -Gln-, -Asn- or a bond, with the condition that if $AA_1$ is -Lys-, $AA_2$ is -Arg-, $AA_3$ is -Phe-, $AA_4$ is -His-, $AA_5$ is -Asn-, $AA_6$ is -Ile-, $AA_8$ is -Gly- and $AA_9$ is a bond, then n+m+p+q is equal to 0.

In accordance with another embodiment of this invention $AA_1$ is selected from the group formed by -Arg-, -His-, -Lys-, -Gln-, -Asn-, -Glu- and -Asp-, $AA_2$ is selected from the group formed by -Arg-, -His-, -Lys-, -Gln-, -Asn-, and -Asp-, $AA_3$ is selected from the group formed by -Leu-, -Glu-, and -Phe-, $AA_4$ is selected from the group formed by -His- and -Glu-, $AA_5$ is selected from the group formed by -Arg-, -His-, -Lys-, -Gln-, -Asn- and -Asp-, $AA_6$ is selected from the group formed by -Ile- and -Lys-, $AA_7$ is selected from the group formed by -Met-, -MetO-, and -MetO$_2$-, $AA_8$ is -Asp- and $AA_9$ is selected from the group formed by -Gln-, -Asn- or a bond. In a preferred embodiment, n, m, p and q are 0.

In accordance with a preferred embodiment, $AA_1$ is selected from the group formed by -Arg-, -His-, -Lys-, -Gln-, -Asn-, -Glu- and -Asp-, $AA_2$ is selected from the group formed by -Arg-, -His-, -Lys-, -Gln-, -Asn-, and -Asp-, $AA_3$ is selected from the group formed by -Glu- and -Phe-, $AA_4$ is -His-, $AA_5$ is selected from the group formed by -Arg-, -His-, -Lys-, -Gln-, and -Asn-, $AA_6$ is -Lys-, $AA_7$ is selected from the group formed by -Met-, -MetO- and -MetO$_2$-, $AA_8$ is -Asp- and $AA_9$ is a bond. More preferably, n, m, p and q are 0.

In accordance with a preferred embodiment, $AA_1$ is selected from the group formed by -Gln-, -Asn-, -Glu- and -Asp-, $AA_2$ is selected from the group formed by -Gln-, -Asn-, and -Asp-, $AA_3$ is selected from the group formed by -Leu- and -Glu-, $AA_4$ is -Glu-, $AA_5$ is selected from the group formed by -Arg-, -His-, -Lys-, -Gln-, and -Asn-, $AA_6$ is -Ile-, $AA_7$ is selected from the group formed by -Met-, -MetO-, and -MetO$_2$-, $AA_8$ is -Asp- and $AA_9$ is selected from the group formed by -Gln- and -Asn-. More preferably, $AA_3$ is -Leu-. Even more preferably, n, m, p and q are 0.

In accordance with another embodiment of this invention $R_1$ is selected from the group formed by H, acetyl, lauroyl, myristoyl and palmitoyl, $AA_1$ is selected from the group formed by -L-Asn-, -L-Gln-, -L-His and -L-Asp-, $AA_2$ is selected from the group formed by -L-His-, -L-Gln-, and -L-Asn-, $AA_3$ is selected from the group formed by -L-Glu-, -L-Leu-, and -L-Phe-, $AA_4$ is selected from the group formed by -L-His- and -L-Glu-, $AA_5$ is selected from the group formed by -L-Arg-, -L-Gln-, -L-Asn- and -L-His-, $AA_6$ is selected from the group formed by -L-Ile- and -L-Lys-, $AA_7$ is selected from the group formed by -L-Met-, -L-MetO-, and -L-MetO$_2$-, $AA_8$ is -L-Asp-, $AA_9$ is selected from the group formed by -L-Gln-, -L-Asn- or a bond, and $R_2$ is selected from the group formed by —$NR_3R_4$ and —$OR_3$ where $R_3$ and $R_4$ are independently selected from the group formed by —$NR_3R_4$ and —$OR_3$ where $R_3$ and $R_4$ are independently selected from H, methyl, ethyl, hexyl, dodecyl and hexadecyl. More preferably, $R_1$ is acetyl or palmitoyl and $R_2$ is —$NH_2$. Even more preferably, n, m, p and q are 0.

In accordance with another embodiment of this invention $R_1$ is selected from the group formed by H, acetyl, lauroyl, myrisotyl and palmitoyl, $AA_1$ is selected from the group formed by -L-Asn-, -L-Glu-, -L-Arg-, -L-Lys-, -L-His-, -L-Glu- and -L-Asp-, $AA_2$ is selected from the group formed by -L-Asn-, -L-Gln-, -L-Arg-, -L-Lys, -L-His- and -L-Asp-, $AA_3$ is selected from the group formed by -L-Glu- and -L-Phe-, $AA_4$ is -L-His-, $AA_5$ is selected from the group formed by -L-Asn-, -L-Gln-, -L-Arg-, -L-Lys- and -L-His-, $AA_6$ is -L-Lys-, $AA_7$ is selected from the group formed by -L-Met-, -L-MetO-, and -L-MetO$_2$-, $AA_8$ is -L-Asp-, $AA_9$ is a bond, and $R_2$ is selected from the group formed by —NR$_3$R$_4$ and —OR$_3$ where $R_3$ and $R_4$ are independently selected from H, methyl, ethyl, hexyl, dodecyl and hexadecyl. More preferably, $R_1$ is acetyl or palmitoyl and $R_2$ is —NH$_2$. Even more preferably, n, m, p and q are 0.

In accordance with another embodiment of this invention $R_1$ is selected from the group formed by H, acetyl, lauroyl, myrisotyl and palmitoyl, $AA_1$ is selected from the group formed by -L-Asn-, -L-Gln-, -L-Glu-, -L-Asp-, $AA_2$ is selected from the group formed by -L-Gln-, -L-Asn-, and -L-Asp-, $AA_3$ is selected from the group formed by -L-Glu- and -L-Leu-, $AA_4$ is -L-Glu-, $AA_5$ is selected from the group formed by -L-Asn-, -L-Gln-, -L-Arg-, -L-Lys- and -L-His-, $AA_6$ is -L-Ile-, $AA_7$ is selected from the group formed by -L-Met-, -L-MetO- and -L-MetO$_2$-, $AA_8$ is -L-Asp-, $AA_9$ is selected from the group formed by -L-Gln- and -L-Asn-, and $R_2$ is selected from the group formed by —NR$_3$R$_4$ and —OR$_3$ where $R_3$ and $R_4$ are independently selected from H, methyl, ethyl, hexyl, dodecyl and hexadecyl. More preferably, $AA_3$ is -L-Leu-. More preferably, $R_1$ is acetyl or palmitoyl and $R_2$ is —NH$_2$. Even more preferably, n, m, p and q are 0.

In accordance with another embodiment of this invention $R_1$ is selected from the group formed by H, acetyl, lauroyl, myrisotyl and palmitoyl, $AA_1$ is -L-His-, $AA_2$ is -L-Gln-, $AA_3$ is -L-Glu-, $AA_4$ is -L-His-, $AA_5$ is -L-Arg-, $AA_6$ is -L-Lys-, $AA_7$ is -L-Met-, -L-MetO-, and -L-MetO$_2$-, $AA_8$ is -L-Asp-, $AA_9$ is a bond, and $R_2$ is —NR$_3$R$_4$ or —OR$_3$ where $R_3$ and $R_4$ are independently selected from H, methyl, ethyl, hexyl, dodecyl and hexadecyl, preferably, $R_2$ is —OH or —NH$_2$. More preferably, $R_1$ is acetyl or palmitoyl and $R_2$ is —NH$_2$. Even more preferably, n, m, p and q are 0.

In accordance with another embodiment of this invention $R_1$ is selected from the group formed by H, acetyl, lauroyl, myrisotyl and palmitoyl, $AA_1$ is -L-Asp-, $AA_2$ is -L-Gln-, $AA_3$ is -L-Glu-, $AA_4$ is -L-His-, $AA_5$ is -L-Gln-, $AA_6$ is -L-Lys-, $AA_7$ is -L-Met-, -L-MetO-, or -L-MetO$_2$-, $AA_8$ is -L-Asp-, $AA_9$ is a bond and $R_2$ is —NR$_3$R$_4$ or —OR$_3$ where $R_3$ and $R_4$ are independently selected from H, methyl, ethyl, hexyl, dodecyl and hexadecyl, preferably, $R_2$ is —OH or —NH$_2$. More preferably, $R_1$ is acetyl or palmitoyl and $R_2$ is —NH$_2$. Even more preferably, n, m, p and q are 0.

In accordance with another embodiment of this invention $R_1$ is selected from the group formed by H, acetyl, lauroyl, myrisotyl and palmitoyl, $AA_1$ is -L-Gln-, $AA_2$ is -L-His-, $AA_3$ is -L-Phe-, $AA_4$ is -L-His-, $AA_5$ is -L-Gln-, $AA_6$ is -L-Lys-, $AA_7$ is -L-Met-, -L-MetO-, or -L-MetO$_2$-, $AA_8$ is -L-Asp-, $AA_9$ is a bond and $R_2$ is —NR$_3$R$_4$ or —OR$_3$ where $R_3$ and $R_4$ are independently selected from H, methyl, ethyl, hexyl, dodecyl and hexadecyl, preferably, $R_2$ is —OH or —NH$_2$. More preferably, $R_1$ is acetyl or palmitoyl and $R_2$ is —NH$_2$. Even more preferably, n, m, p and q are 0.

In accordance with another embodiment of this invention $R_1$ is selected from the group formed by H, acetyl, lauroyl, myrisotyl and palmitoyl, $AA_1$ is -L-Asn-, $AA_2$ is -L-Asn-, $AA_3$ is -L-Leu-, $AA_4$ is -L-Glu-, $AA_5$ is -L-Asn-, $AA_6$ is -L-Ile-, $AA_7$ is -L-Met-, -L-MetO-, or -L-MetO$_2$-, $AA_8$ is -L-Asp-, $AA_9$ is -L-Gln- or -L-Asn- and $R_2$ is —NR$_3$R$_4$ or —OR$_3$ where $R_3$ and $R_4$ are independently selected from H, methyl, ethyl, hexyl, dodecyl and hexadecyl, preferably, $R_2$ is —OH or —NH$_2$. More preferably $R_1$ is acetyl or palmitoyl and $R_2$ is —NH$_2$. Even more preferably, n, m, p and q are 0.

In accordance with another embodiment of this invention $R_1$ is selected from the group formed by H, acetyl, lauroyl, myrisotyl and palmitoyl, $AA_1$ is -L-Gln-, $AA_2$ is -L-Gln-, $AA_3$ is -L-Leu-, $AA_4$ -L-Glu-, $AA_5$ is -L-Asn-, $AA_6$ is -L-Ile-, $AA_7$ is -L-Met-, -L-MetO-, and -L-MetO$_2$-, $AA_8$ is -L-Asp-, $AA_9$ is -L-Asn- and $R_2$ is —NR$_3$R$_4$ and —OR$_3$ where $R_3$ and $R_4$ are independently selected from H, methyl, ethyl, hexyl, dodecyl and hexadecyl, preferably $R_2$ is —OH or —NH$_2$. More preferably, $R_1$ is acetyl or palmitoyl and $R_2$ is —NH$_2$. Even more preferably, n, m, p and q are 0.

In accordance with another embodiment of this invention $R_1$ is selected from the group formed by H, acetyl, lauroyl, myrisotyl and palmitoyl, $AA_1$ is -L-Gln-, $AA_2$ is -L-Asn-, $AA_3$ is -L-Leu-, $AA_4$ is -L-Glu-, $AA_5$ is -L-His-, $AA_6$ is -L-Ile-, $AA_7$ is -L-Met-, -L-MetO-, and -L-MetO$_2$-, $AA_8$ is -L-Asp-, $AA_9$ is -L-Gln and $R_2$ is —NR$_3$R$_4$ or —OR$_3$ where $R_3$ and $R_4$ are independently selected from H, methyl, ethyl, hexyl, dodecyl and hexadecyl, preferably $R_2$ is —OH or —NH$_2$. More preferably, $R_1$ is acetyl or palmitoyl and $R_2$ is —NH$_2$. Even more preferably, n, m, p and q are 0.

In particular, the compounds in the invention which inhibit neuronal exocytosis, represented according to the formula (I) are selected from the group of peptide sequences outlined in Table 2, in which their sequence identifier is detailed:

TABLE 2

| SEQUENCE | IDENTIFIER |
|---|---|
| QREHRKMD | SEQ ID NO: 1 |
| KQEHHKMD | SEQ ID NO: 2 |
| KNEHRKMD | SEQ ID NO: 3 |
| KQEHRKMD | SEQ ID NO: 4 |
| HQEHRKMD | SEQ ID NO: 5 |
| EQEHRKMD | SEQ ID NO: 6 |
| DKEHRKMD | SEQ ID NO: 7 |
| NREHRKMD | SEQ ID NO: 8 |

TABLE 2-continued

| SEQUENCE | IDENTIFIER |
|---|---|
| HEEHRMMD | SEQ ID NO: 9 |
| HQYDEVMD | SEQ ID NO: 10 |
| DQEHQKMD | SEQ ID NO: 11 |
| DKEHNKMD | SEQ ID NO: 12 |
| ENEHDKMD | SEQ ID NO: 13 |
| DQEHRKMD | SEQ ID NO: 14 |
| NQEHRKMD | SEQ ID NO: 15 |
| DQEEQIMD | SEQ ID NO: 16 |
| DQDKQHMD | SEQ ID NO: 17 |
| ENEHRKMD | SEQ ID NO: 18 |
| EHEHRKMD | SEQ ID NO: 19 |
| QNEHHKMD | SEQ ID NO: 20 |
| KKEHQKMD | SEQ ID NO: 21 |
| HREHQKMD | SEQ ID NO: 22 |
| DHEHRKMD | SEQ ID NO: 23 |
| EREHRKMD | SEQ ID NO: 24 |
| HREHKKMD | SEQ ID NO: 25 |
| RDFHRKMD | SEQ ID NO: 26 |
| QHFHQKMD | SEQ ID NO: 27 |
| RDFHQKMD | SEQ ID NO: 28 |
| EKMHQIMG | SEQ ID NO: 29 |
| DQMHDIMG | SEQ ID NO: 30 |
| EQMHNIMG | SEQ ID NO: 31 |
| HRLHDRMD | SEQ ID NO: 32 |
| QKLHRRMD | SEQ ID NO: 33 |
| QDFHDIMA | SEQ ID NO: 34 |
| HDFHDIMA | SEQ ID NO: 35 |
| EQLEKRMD | SEQ ID NO: 36 |
| QHVHEKMD | SEQ ID NO: 37 |
| QHDHQLMD | SEQ ID NO: 38 |
| REWDHVMP | SEQ ID NO: 39 |
| His-Gln-Glu-His-Arg-Lys-MetO-Asp | SEQ ID NO: 40 |
| Asp-Gln-Glu-His-Gln-Lys-MetO-Asp | SEQ ID NO: 41 |
| Glu-Asn-Glu-His-Arg-Lys-MetO-Asp | SEQ ID NO: 42 |
| Gln-His-Phe-His-Gln-Lys-MetO-Asp | SEQ ID NO: 43 |
| His-Gln-Glu-His-Arg-Lys-MetO$_2$-Asp | SEQ ID NO: 44 |
| Asp-Gln-Glu-His-Gln-Lys-MetO$_2$-Asp | SEQ ID NO: 45 |
| Gln-His-Phe-His-Gln-Lys-MetO$_2$-Asp | SEQ ID NO: 46 |
| DNLEKIMDQ | SEQ ID NO: 47 |

TABLE 2-continued

| SEQUENCE | IDENTIFIER |
|---|---|
| NNLENIMDN | SEQ ID NO: 48 |
| NNIENIMPN | SEQ ID NO: 49 |
| ENLEKIMDQ | SEQ ID NO: 50 |
| QQLENIMDN | SEQ ID NO: 51 |
| QNLERIMDQ | SEQ ID NO: 52 |
| QNLEKIMDQ | SEQ ID NO: 53 |
| QQLENKMEN | SEQ ID NO: 54 |
| QELENIMDN | SEQ ID NO: 55 |
| QQLEKIMDQ | SEQ ID NO: 56 |
| QQLEHIMDQ | SEQ ID NO: 57 |
| EQLEKIMDQ | SEQ ID NO: 58 |
| NNLENIMDQ | SEQ ID NO: 59 |
| NELENHMDQ | SEQ ID NO: 60 |
| NNYENIMDN | SEQ ID NO: 61 |
| QNLEHIMDQ | SEQ ID NO: 62 |
| QNWEHLMDQ | SEQ ID NO: 63 |
| NDIKHMMEQ | SEQ ID NO: 64 |
| EHQEHRKMD | SEQ ID NO: 65 |
| HQEHRKMDN | SEQ ID NO: 66 |
| EDQEHQKMD | SEQ ID NO: 67 |
| DQEHQKMDN | SEQ ID NO: 68 |
| EQHFHQKMD | SEQ ID NO: 69 |
| QHFHQKMDN | SEQ ID NO: 70 |
| DENEHRKMD | SEQ ID NO: 71 |
| ENEHRKMDQ | SEQ ID NO: 72 |
| Asn-Asn-Leu-Glu-Asn-Ile-MetO-Asp-Asn | SEQ ID NO: 73 |
| Gln-Gln-Leu-Glu-Asn-Ile-MetO-Asp-Asn | SEQ ID NO: 74 |
| Gln-Gln-Leu-Glu-Lys-Ile-MetO-Asp-Gln | SEQ ID NO: 75 |
| Asn-Asn-Leu-Glu-Asn-Ile-MetO-Asp-Gln | SEQ ID NO: 76 |
| Gln-Asn-Leu-Glu-His-Ile-MetO-Asp-Gln | SEQ ID NO: 77 |
| Glu-His-Gln-Glu-His-Arg-Lys-MetO-Asp | SEQ ID NO: 78 |
| Asp-Gln-Glu-His-Gln-Lys-MetO-Asp-Asn | SEQ ID NO: 79 |
| Gln-His-Phe-His-Gln-Lys-MetO-Asp-Asn | SEQ ID NO: 80 |
| Asn-Asn-Leu-Glu-Asn-Ile-MetO$_2$-Asp-Asn | SEQ ID NO: 81 |
| Gln-Gln-Leu-Glu-Asn-Ile-MetO$_2$-Asp-Asn | SEQ ID NO: 82 |
| Asn-Asn-Leu-Glu-Asn-Ile-MetO$_2$-Asp-Glu | SEQ ID NO: 83 |
| Gln-Asn-Leu-Glu-His-Ile-MetO$_2$-Asp-Gln | SEQ ID NO: 84 |
| Glu-His-Gln-Glu-His-Arg-Lys-MetO$_2$-Asp | SEQ ID NO: 85 |
| DEHQEHRKMD | SEQ ID NO: 86 |

TABLE 2-continued

| SEQUENCE | IDENTIFIER |
|---|---|
| HQEHRKMDNR | SEQ ID NO: 87 |
| HEDQEHQKMD | SEQ ID NO: 88 |
| DQEHQKMDNK | SEQ ID NO: 89 |
| NEQHFHQKMD | SEQ ID NO: 90 |
| QHFHQKMDNK | SEQ ID NO: 91 |
| HNNLENIMDN | SEQ ID NO: 92 |
| NNLENIMDNQ | SEQ ID NO: 93 |
| DQQLENIMDN | SEQ ID NO: 94 |
| QQLENIMDNK | SEQ ID NO: 95 |
| HNNLENIMDQ | SEQ ID NO: 96 |
| NNLENIMDQQ | SEQ ID NO: 97 |
| KQNLEHIMDQ | SEQ ID NO: 98 |
| QNLEHIMDQR | SEQ ID NO: 99 |
| EQQLEHIMDQ | SEQ ID NO: 100 |
| QQLEHIMDQR | SEQ ID NO: 101 |
| Asp-Glu-His-Gln-Glu-His-Arg-Lys-MetO-Asp | SEQ ID NO: 102 |
| Asp-Gln-Glu-His-Gln-Lys-MetO-Asp-Asn-Lys | SEQ ID NO: 103 |
| Asn-Glu-Gln-His-phe-His-Gln-Lys-MetO-Asp | SEQ ID NO: 104 |
| His-Asn-Asn-Leu-Glu-Asn-Ile-MetO-Asp-Asn | SEQ ID NO: 105 |
| Gln-Gln-Leu-Glu-Asn-Ile-MetO-Asp-Asn-Lys | SEQ ID NO: 106 |
| Asn-Asn-Leu-Glu-Asn-Ile-MetO-Asp-Gln-Gln | SEQ ID NO: 107 |
| Lys-Gln-Asn-Leu-Glu-His-Ile-MetO-Asp-Gln | SEQ ID NO: 108 |
| Glu-Gln-Gln-Leu-Glu-His-Ile-MetO-Asp-Gln | SEQ ID NO: 109 |
| Asp-Glu-His-Gln-Glu-His-Arg-Lys-MetO$_2$-Asp | SEQ ID NO: 110 |
| His-Asn-Asn-Leu-Glu-Asn-Ile-MetO$_2$-Asp-Asn | SEQ ID NO: 111 |
| Gln-Gln-Leu-Glu-Asn-Ile-MetO$_2$-Asp-Asn-Lys | SEQ ID NO: 112 |
| Lys-Gln-Asn-Leu-Glu-His-Ile-MetO$_2$-Asp-Gln | SEQ ID NO: 113 |
| HNNLENIMDNR | SEQ ID NO: 114 |
| NNLENIMDNQQ | SEQ ID NO: 115 |
| DQQLENIMDNR | SEQ ID NO: 116 |
| QQLENIMDNKH | SEQ ID NO: 117 |
| HNNLENIMDQR | SEQ ID NO: 118 |
| NNLENIMDQQR | SEQ ID NO: 119 |
| AKQNLEHIMDQ | SEQ ID NO: 120 |
| QNLEHIMDQRK | SEQ ID NO: 121 |
| EQQLEHIMDQR | SEQ ID NO: 122 |
| QQLEHIMDQRK | SEQ ID NO: 123 |
| His-Asn-Asn-Leu-Glu-Asn-Ile-MetO-Asp-Asn-Arg | SEQ ID NO: 124 |
| Gln-Gln-Leu-Glu-Asn-Ile-MetO-Asp-Asn-Lys-His | SEQ ID NO: 125 |

TABLE 2-continued

| SEQUENCE | IDENTIFIER |
|---|---|
| Asn-Asn-Leu-Glu-Asn-Ile-MetO-Asp-Gln-Gln-Arg | SEQ ID NO: 126 |
| Ala-Lys-Gln-Asn-Leu-Glu-His-Ile-MetO-Asp-Gln | SEQ ID NO: 127 |
| Glu-Gln-Gln-Leu-Glu-His-Ile-MetO-Asp-Gln-Arg | SEQ ID NO: 128 |
| His-Asn-Asn-Leu-Glu-Asn-Ile-MetO$_2$-Asp-Asn-Arg | SEQ ID NO: 129 |
| Gln-Gln-Leu-Glu-Asn-Ile-MetO$_2$-Asp-Asn-Lys-His | SEQ ID NO: 130 |
| Ala-Lys-Gln-Asn-Leu-Glu-His-Ile-MetO$_2$-Asp-Gln | SEQ ID NO: 131 | their stereoisomers, mixtures thereof and/or their cosmetically or pharmaceutically acceptable salts.

The compounds of this invention can exist as stereoisomers or mixtures of stereoisomers; for example, the amino acids which comprise them can have the configuration L-, D-, or be racemic independently of each other. Therefore, it is possible to obtain isomeric mixtures as well as racemic mixtures or diastereomeric mixtures, or pure diastereomers or enantiomers, depending on the number of asymmetric carbons and on which isomers or isomeric mixtures are present. The preferred structures of the compounds of the invention are pure isomers, i.e., enantiomers or diastereomers.

For example, when it is stated that $AA_1$ can be -Lys-, it is understood that $AA_1$ is selected from -L-Lys-, -D-Lys- or mixtures of both, racemic or non-racemic. The preparation procedures described in this document enable the person skilled in the art to obtain each of the stereoisomers of the compound of the invention by choosing the amino acid with the right configuration.

In the context of this invention, the term "amino acids" includes the amino acids encoded by the genetic code as well as non-encoded amino acids, whether they are natural or not. Examples f non-encoded amino acids are, without restriction, citrulline, ornithine, sarcosine, desmosine, norvaline, 4-aminobutyric acid, 2-aminobutyric acid, 2-aminoisobutyric acid, 6-aminohexanoic acid, 1-naphthylalanine, 2-naphthylalanine, 2-aminobenzoic acid, 4-aminobenzoic acid, 4-chlorophenylalanine, 2,3-diaminopropionic acid, 2,4-diaminobutyric acid, cycloserine, carnitine, cystine, penicillamine, pyroglutamic acid, thienylalanine, hydroxyproline, allo-isoleucine, allo-threonine, isonipecotic acid, isoserine, phenylglycine, statin, β-alanine, norleucine, N-methyl amino acids, α-amino acids and β-amino acids, among others, as well as their derivatives. A list of non-natural amino acids can be found in the article "*Unusual amino acids in peptide synthesis*" by D. C. Roberts and F. Vellaccio, in *The Peptides*, Vol. 5 (1983), Chapter VI, Gross E. and Meienhofer J., Eds., Academic Press, New York, USA or in the commercial catalogs of the companies specialized in the field.

In the context of this invention, when n, m, p or q are not 0 it is clearly understood that the nature of W, X, Y and/or Z does not hinder the activity of the compounds of the invention, but that it contributes to the inhibition of neuronal exocytosis or has no effect on it.

The cosmetically and pharmaceutically acceptable salts of the peptides provided by this invention are also found within the field of this invention. The term "cosmetically or pharmaceutically acceptable salts" means a salt recognized for its use in animals and more specifically in human beings, and includes salts used to form base addition salts, either they are inorganic, such as and not restricted to, lithium, sodium, potassium, calcium, magnesium, manganese, copper, zinc or aluminum among others, either they are organic, such as and not restricted to, ethylamine, diethylamine, ethylenediamine, ethanolamine, diethanolamine, arginine, lysine, histidine or piperazine among others, or acid addition salts, either they are organic, such as and not restricted to, acetate, citrate, lactate, malonate, maleate, tartrate, fumarate, benzoate, aspartate, glutamate, succinate, oleate, trifluoroacetate, oxalate, pamoate or gluconate among others, or inorganic, such as and not restricted to, chloride, sulfate, borate or carbonate, among others. The nature of the salt is not critical, provided that it is cosmetically or pharmaceutically acceptable. The cosmetically or pharmaceutically acceptable salts of the peptides of the invention can be obtained by the conventional methods, well known in the prior art [Berge S. M. et al., "*Pharmaceutical Salts*", (1977), *J. Pharm. Sci.*, 66, 119].

Preparation Procedures of the Compounds of the Invention

Synthesis of the compounds of the invention, their stereoisomers, mixtures thereof and/or their cosmetically or pharmaceutically acceptable salts can be carried out according to conventional methods, known in the prior art, such as using solid phase peptide synthesis methods [Stewart J. M and Young J. D., "*Solid Phase Peptide Synthesis, 2nd edition*", (1984), Pierce Chemical Company, Rockford, Ill.; Bodanzsky M. and Bodanzsky A., "*The practice of Peptide Synthesis*", (1994), Springer Verlag, Berlin; Lloyd-Williams P. et al., "*Chemical Approaches to the Synthesis of Peptides and Proteins*", (1997), CRC, Boca Raton, Fla., USA], synthesis in solution, enzymatic synthesis [Kullmann W. "*Proteases as catalysts for enzymic syntheses of opioid peptides*", (1980), *J. Biol. Chem.*, 255(17), 82348238] or any combination thereof. Compounds can also be obtained by fermentation of a strain of bacteria, modified or unmodified, by genetic engineering with the objective of producing the desired sequences, or by controlled hydrolysis of proteins with animal, fungal, or preferably plant origins, which free peptide fragments which contain, at least, the desired sequence.

For example, a method of obtaining the compounds (I) of the invention, their stereoisomers and mixtures thereof comprises the stages of:

coupling of an amino acid, with the N-terminal and protected and the C-terminal end free, with an amino acid with the N-terminal end free and the C-terminal end protected or bound to a solid support;

elimination of the group protecting the N-terminal end;

repetition of the coupling sequence and elimination of the group protecting the N-terminal end until the desired peptide sequence is obtained, elimination of the group protecting the C-terminal end or cleavage of the solid support.

Preferably, the C-terminal end is bound to a solid support and the procedure is carried out in solid phase and, therefore, comprises the coupling of an amino acid with the protected N-terminal end and the free C-terminal end with an amino acid with the N-terminal end free and the C-terminal end bound to a polymeric support; elimination of the group protecting the N-terminal end; and repetition of this sequence as many times as is necessary to thus obtain the compound of the desired length, finally followed by the cleavage of the synthesized compound from the original polymeric support.

The functional groups of the side chains of the amino acids are maintained conveniently protected with temporary or permanent protective groups throughout synthesis, and can be unprotected simultaneously or orthogonally to the process of cleavage of the peptide from the polymeric support.

Alternatively, solid phase synthesis can be carried out using a convergent strategy coupling a peptide with the polymeric support or with a peptide or amino acid previously bound to the polymeric support. Convergent synthesis strategies are widely known by persons skilled in the art and are described in Lloyd-Williams P. et al., "Convergent Solid-Phase Peptide Synthesis", (1993), Tetrahedron, 49(48), 11065-11133.

The procedure can comprise the additional stages of deprotection of the N-terminal and C-terminal ends and/or cleavage of the peptide from the polymeric support in an indiscriminate order, using standard procedures and conditions known in the prior art, after which the functional groups of these ends can be modified. The optional modification of the N-terminal and C-terminal ends can be carried out with the peptide of formula (I) anchored to the polymeric support or once the peptide has been separated from the polymeric support.

Optionally, $R_1$ can be introduced by the reaction of the N-terminal end of the compound of the invention with a $R_1$—X compound, wherein $R_1$ has the aforementioned meaning and X is a leaving group, such as and not restricted to, the tosyl group, the mesyl group and halogen groups among others; through a nucleophilic substitution reaction, in the presence of an adequate base and solvent, wherein the fragments that have the functional groups not involved in the N—C bond formation are suitably protected with temporary or permanent protective groups.

Optionally and/or additionally, the $R_2$ radicals can be introduced by the reaction of a compound $HR_2$ wherein $R_2$ is —$OR_3$, —$NR_3R_4$ or —$SR_3$, with a complementary fragment which corresponds to the compound of formula (I) in which $R_2$ is —OH in the presence of an adequate solvent and a base such as, N,N-diisopropylehtylamine (DIEA) or triethylamine or an additive such as 1-hydroxybenzotriazole (HOBt) or 1-hydroxyazabenzotriazole (HOAt) and a dehydrating agent, such as a carbodiimide, a uronium salt, a phosphonium salt or amidinium salt, among others, or by prior formation of an acyl halide with, for example, thionyl chloride, and thereby obtaining a peptide according to the invention of general formula (I), wherein the fragments that have the functional groups not involved in the N—C bond formation are suitably protected with temporary or permanent protective groups, or alternatively other $R_2$ radicals may be introduced by simultaneous incorporation to the cleavage process of the peptide from the polymeric support.

A person skilled in the art would easily understand that the deprotection/cleavage steps of the C-terminal and N-terminal ends and their subsequent derivatization can be performed in a different order, according to the processes known in the prior art.

The term "protective group" relates to a group which blocks an organic functional group and which can be removed in controlled conditions. The protective groups, their relative reactivities and the conditions in which they remain inert are known to the person skilled in the art.

Examples of representative protective groups for the amino group are amides, such as amide acetate, amide benzoate, amide pivalate; carbamates such as benzyloxycarbonyl (Cbz or Z), 2-chlorobenzyl (ClZ), para-nitrobenzyloxycarbonyl (pNZ), tert-butyloxycarbonyl (Boc), 2,2,2-trichloroethyloxycarbonyl (Troc), 2-(trimethylsilyl)ethyloxycarbonyl (Teoc), 9-fluorenylmethyloxycarbonyl (Fmoc) or allyloxycarbonyl (Alloc), Trityl (Trt), methoxytrityl (Mtt), 2,4-dintrophenyl (Dnp), N-[1-(4,4-dimethyl-2,6-dioxocyclohex-1-ylidene)ethyl (Dde), 1-(4,4-dimethyl-2,6-dioxocyclohexylidene)-3-methylbutyl (ivDde), 1-(1-adamantyl)-1-methylethoxycarbonyl (Adpoc), among others, preferably Boc or Fmoc.

Examples of representative protective groups for the carboxyl group are esters, such as the tert-butyl ester (tBu), allyl ester (All), triphenylmethyl ester (Trt ester), cyclohexyl ester (cHx), benzyl ester (Bzl), ortho-nitrobenzyl ester, para-nitrobenzyl ester, para-methoxybenzyl ester, trimethylsilylethyl ester, 2-phenylisopropyl ester, fluorenylmethyl ester (Fm), 4-{N-[1-(4,4-dimethyl-2,6-dioxocyclohexylidene)-3-methylbutyl]amino}benzyl ester (Dmab), among others; preferred protective groups of the invention are the All, tBu, cHx, Bzl and Trt esters.

The side chains of the trifunctional amino acids can be protected during the synthetic process with temporary or permanent protective groups orthogonal to the protective groups of the N-terminal and C-terminal ends.

The hydroxyl group of the tyrosine side chain can be protected with the 2-bromobenzyloxycarbonyl group (2-BrZ), tBu, All, Bzl or 2,6-dichlorobenzyl (2,6-diClZ) among others. The histidine side chain can be protected by a protective group selected from the group formed by Tos, Dnp, methyl (Me), Boc, benzyloxymethyl (Bom), Bzl, Fmoc, Mts, Trt and Mtt. The amide group of the glutamine and asparagine side chain can be protected by the Trt group or xanthyl group (Xan) or can be used unprotected. For the protection of the carboxyl group of the aspartic acid and glutamic acid side chain esters can be used such as tBu ester. All ester, triphenylmethyl ester (Trt ester), cHx ester, Bzl ester, orto-nitrobenzyl ester, para-nitrobenzyl ester, para-methoxybenzyl ester, trimethylsilylethyl ester, 2-phenylisopropyl ester, Fm ester or Dmab ester, among others. The arginine side chain can be protected by a protective group selected from the group formed by Tos, 4-methoxy-2,3,6-trimethylbenzenesulfonyl (Mtr), Alloc, nitro, 2,2,4,6,7-pentamethyldihydrobenzofuran-5-sulfonyl (Pbf) and 2,2,5,7,8-pentamethylchroman-6-sulfonyl (Pmc). The indole group of the tryptophan side chain can be protected by the formyl group (For), Boc, Mts or can be used unprotected. For the protection of the amino groups of the lysine side chains amides can be used, such as amide acetate, amide benzoate, amide pivalate, carbamates such as Cbz or Z, ClZ, pNZ, Boc, Troc, Teoc, Fmoc or Alloc, Trt, Mtt, Dnp, Dde, ivDde, Adpoc, among others. The methionine side chain can be protected in sulfoxide form, in sulfone form or used without protection. The methionyl(sulfoxide) and methionyl(sulfone) side chains are not protected.

In a preferred embodiment, the protective group strategy used is the strategy wherein the amino groups are protected by Boc, the carboxyl groups are protected by Bzl, cHx or All, the tyrosine side chain is protected with 2-BrZ or Bzl, the histidine side chain is protected by the Tos or Bom group, the aspartic acid and glutamic acid side chains are protected with Bzl, cHx or All, glutamine and asparagine are used without protection in their side chain, methionine is used without protection in its side chain, the arginine side chain is protected by Tos, the tryptophan side chain is protected by For or Mts and the lysine side chain is protected by ClZ, Fmoc, or Alloc.

In another preferred embodiment, the protective group strategy used is the strategy wherein the amino groups are protected by Fmoc, the carboxyl groups are protected by the tBu, All or Trt esters, the tyrosine side chain is protected by tBu, the histidine side chain is protected by the Trt or Mtt group, the aspartic acid and glutamic acid side chains are protected with tBu or All, glutamine and asparagine are protected by the Trt group in their side chain, methionine is used without protection in its side chain, the arginine side chain is protected by Pmc or Pbf, the tryptophan side chain is protected by Box or is used unprotected, and the lysine side chain is protected by Boc, Trt or Alloc.

Examples of these and other additional protective groups, their introduction and removal, can be found in the literature [Atherton B. and Sheppard R. C., "*Solid Phase Peptide Synthesis: A practical approach*", (1989), IRL Oxford University Press]. The term "protective groups" also includes the polymeric supports used in solid phase synthesis.

When synthesis takes place totally or partially in solid phase, the possible solid supports used in the procedure of the invention involve polystyrene supports, polyethylene glycol grafted to polystyrene and similar, such as and not restricted to, p-methylbenzhydrylamine resins (MBHA) [Matsueda G. R. et al., "*A p-methylbenzhydrylamine resin for improved solid phase synthesis of peptide amides*", (1981), *Peptides*, 2, 4550], 2-chlorotrityl resins [Barlos K. et al., "*Darstellung geschützler PeptidFragmente unter Einsatz substituierter TriphenylmethylHarze*", (1989), *Tetrahedron Lett.,* 30, 39433946, Barlos K. et al., "*Veresterung von partiell geschützten PeptidFragmenten mit Harzen, Einsatz von 2-Chlorotritylchlorid zur Synthese von Lue1Gastrin I*", (1989), *Tetrahedron Lett.,* 30, 39473951], TentaGel® resins (Rapp Polymere GmbH), ChemMatrix® resins (Matrix Innovation, Inc.) and similar, which may or may not include a labile linker, such as 5-(4-aminomethyl-3,5-dimethoxyphenoxy)valeric acid (PAL) [Albericio F. et al., "*Preparation and application of the 5-(4-(9-fluorenylmethyloxycarbonyl) aminomethyl-3,5-dimethoxy-phenoxy)valeric acid (PAL) handle for the solid phase synthesis of C-terminal peptide amides under mild conditions*", (1990), *J. Org. Chem.,* 55, 37303743], 2-[4-aminomethyl-(2,4-dimethoxyphenyl)]phenoxyacetic acid (AM) [Rink H., "*Solid phase synthesis of protected peptide fragments using a trialkoxydiphenyl-methylester resin*", (1987), *Tetrahedron Lett.,* 28, 3787-3790], Wang [Wang S. S., "*p-Alkoxybenzyl Alcohol Resin and p-Alkoxybenzyloxycarbonylhydrazide Resin for Solid Phase Synthesis or Protected Peptide Fragments*", (1973), *J. Am. Chem. Soc.,* 95, 1328-1333] and similar, which enable simultaneous deprotection and cleavage of the peptide from the polymeric support.

Cosmetic or Pharmaceutical Compositions of the Invention

The compounds of the invention can be administered to inhibit neuronal exocytosis by any means which causes contact between the compounds and the site of action in a mammal's body, preferably that of a human being, and in the form of a composition which contains them.

To this regard, another aspect of the invention is a cosmetic or pharmaceutical composition which comprises at least one compound of general formula (I), its stereoisomers, mixtures thereof, and/or its cosmetically or pharmaceutically acceptable salts together with at least one cosmetically or pharmaceutically acceptable adjuvant. These compositions can be prepared by conventional means known to persons skilled in the art ["*Harry's Cosmeticology*", Seventh edition, (1982), Wilkinson J. B., Moore R. J., ed. Longman House, Essex, GB].

The compounds of this invention have variable solubility in water, according to the nature of their amino acid sequence or any possible modifications in the N-terminal and/or C-terminal ends. Therefore, the compounds of this invention can be incorporated into the compositions by aqueous solution, and those which are not soluble in water can be solubilized in cosmetically or pharmaceutically acceptable conventional solvents such as and not restricted to, ethanol, propanol, isopropanol, propylene glycol, glycerin, butylene glycol or polyethylene glycol or any combination thereof.

The cosmetically or pharmaceutically effective amount of the compounds of the invention which should be administered, as well as their dosage, will depend on numerous factors, including age, state of the patient, the nature or severity of the condition, disorder or disease to be treated and/or cared for, the route and frequency of administration and the particular nature of the compounds to be used.

"Cosmetically and pharmaceutically effective amount" is understood to mean a non-toxic but sufficient amount of the compound or compounds of the invention to provide the desired effect. The compounds of the invention are used in the cosmetic or pharmaceutical composition of this invention at cosmetically or pharmaceutically effective concentrations to achieve the desired effect; in a preferred form with regards to the total weight of the composition, between 0.00000001% (in weight) and 20% (in weight); preferably between 0.000001% (in weight) and 10% (in weight) and even more preferably between 0.00001% (in weight) and 5% (in weight).

The compounds of general formula (I), their stereoisomers, mixtures thereof and/or their cosmetic or pharmaceutically acceptable salts, can also be incorporated into cosmetic or pharmaceutical delivery systems and/or sustained release systems.

The term "delivery systems" relates to a diluent, adjuvant, excipient or carrier with which the compound of the invention is administered. These cosmetic or pharmaceutical carriers can be liquids, such as water, oils, or surfactants, including those of petroleum, animal, plant or synthetic origin, such as and not restricted to, peanut oil, soybean oil, mineral oil, sesame oil, castor oil, polysorbates, sorbitan esters, ether sulfates, sulfates, betaines, glycosides, maltosides, fatty alcohols, nonoxynols, poloxamers, polyoxyethylenes, polyethylene glycols, dextrose, glycerol, digitonin and similar. A person skilled in the art knows the diluents, adjuvants or excipients which can be used in the different delivery systems in which the compound of the invention can be administered.

The term "sustained release" is used in a conventional sense relating to a delivery system of a compound which provides the gradual release of this compound during a period of time and preferably, although not necessarily, with relatively constant compound release levels over a long period of time.

Examples of delivery or sustained release systems include, without restriction, liposomes, mixed liposomes, oleosomes, niosomes, ethosomes, milliparticles, microparticles, nanoparticles and solid lipid nanoparticles, nanostructured lipid carriers, sponges, cyclodextrins, vesicles, micelles, mixed micelles of surfactants, surfactant-phospholipid mixed micelles, millispheres, microspheres and nanospheres, liposphres, millicapsules, microcapsules and nanocapsules, as well as in microemulsions and nanoemulsions, which can be added to achieve a greater penetration of the active principle and/or improve its pharmacokinetic and pharmacodynamic properties. Preferred delivery or sustained release systems are liposomes, surfactant-phospholipid mixed micelles, microemulsions, more preferably water-in-oil microemulsions with an internal structure of reverse micelle and nanocapsules containing microemulsions.

The sustained release systems can be prepared by methods known in the prior art, and the compositions which contain them can be administered, for example, by topical or transdermal administration, including adhesive patches, non-adhesive patches, occlusive patches and microelectric patches, or by systemic administration, for example and not restricted to, oral or parenteral route, including nasal, rectal or subcutaneous implantation or injection, or direct implantation or injection into a specific body part, and preferably should release a relatively constant quantity of the peptides of the invention. The amount of compound contained in the sustained release system will depend, for example, on where the composition is to be administered, the kinetics and duration of the release of the compound of the invention, as well as the nature of the condition, disorder and/or disease to be treated and/or cared for.

The compounds of this invention can also be adsorbed on solid organic polymers or solid mineral supports such as and not restricted to, talc, bentonite, silica, starch or maltodextrin among others.

The compositions which contain the compounds of the general formula (I), their stereoisomers, mixtures thereof and/or their cosmetically or pharmaceutically acceptable salts can also be incorporated into fabrics, non-woven fabrics and medical devices which are in direct contact with the skin, thus releasing the compounds of the invention whether by biodegradation of the binding system to the fabric, non-woven fabric or medical device, or by friction between them and the body, due to bodily moisture, the skin's pH or body temperature. Furthermore, the compounds of the invention can be incorporated into the fabrics and non-woven fabrics used to make garments that are in direct contact with the body. Preferably, the fabrics, non-woven fabrics and medical devices containing the compounds of the invention are used for the treatment and/or care of conditions, disorders and/or diseases which improve or are prevented, delayed or hindered by the inhibition of neuronal exocytosis.

Examples of fabrics, non-woven fabrics, garments, medical devices and means for immobilizing the compounds to them, among which are the delivery systems and/or the sustained release systems described above, can be found in the literature and are known in the prior art [Schaab C. K. (1986) HAPPI May 1986; Nelson G., "Application of microencapsulation in textiles", (2002), Int. J. Pharm., 242(1-2), 55-62; "Biofunctional Textiles and the Skin" (2006) Curr. Probl. Dermatol. v. 33, Hipler U. C. and Elsner P., eds. S. Karger A G, Gasel, Switzerland; Malcolm R. K. et al., "Controlled release of a model antibacterial drug from a novel self-lubricating silicone biomaterial", (2004), J. Cont. Release, 97(2), 313-320]. The preferred fabrics, non-woven fabrics, garments and medical devices are bandages, gauzes, t-shirts, socks, tights, underwear, girdles, gloves, diapers, sanitary napkins, dressings, bedspreads, wipes, adhesive patches, non-adhesive patches, occlusive patches, microelectric patches and/or face masks.

The cosmetic and pharmaceutical compositions which contain the compounds of the invention, their stereoisomers, mixtures thereof and/or their cosmetically or pharmaceutically acceptable salts, can be used in different types of compositions of topical or transdermal application which optionally include cosmetically or pharmaceutically acceptable excipients necessary for formulating the desired administration form. A person skilled in the art knows the different excipients which can be used in the cosmetic or pharmaceutical compositions which contain the compounds of the invention.

The compositions of topical or transdermal application can be produced in any solid, liquid or semi-solid formulation, such as and not restricted to, creams, multiple emulsions such as and not restricted to, oil and/or silicone in water emulsions, water-in-oil and/or silicone emulsions, water/oil/water or water/silicone/water type emulsions, and oil/water/oil or silicone/water/silicone type emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, polysaccharide films, ointments, mousses, pomades, powders, bars, pencils and sprays or aerosols (sprays), including leave-on and rinse-off formulations. These topical or transdermal application formulations can be incorporated using techniques known by the person skilled in the art into different types of solid accessories such as and not restricted to, bandages, gauzes, t-shirts, socks, tights, underwear, girdles, gloves, diapers, sanitary napkins, dressings, bedspreads, wipes, adhesive patches, non-adhesive patches, occlusive patches, microelectric patches or face masks, or they can be incorporated into different make-up products such as make-up foundation, such as fluid foundations and compact foundations, make-up removal lotions, make-up removal milks, under-eye concealers, eye shadows, lipsticks, lip protectors, lip gloss and powders, among others.

The cosmetic or pharmaceutical compositions of the invention may include agents which increase the percutaneous absorption of the compounds of this invention, such as and not restricted to, dimethyl sulfoxide, dimethylacetamide, dimethylformamide, surfactants, azone (1-dodecylazacycloheptane-2-one), alcohol, urea, ethoxydiglycol, acetone, propylene glycol or polyethylene glycol, among others. Furthermore, the cosmetic or pharmaceutical compositions of this invention can be applied to local areas to be treated by means of iontophoresis, sonophoresis, electroporation, microelectric patches, mechanical pressure, osmotic pressure gradient, occlusive cure, microinjections or needle-free injections by means of pressure, such as injections by oxygen pressure, or any combination thereof, to achieve a greater penetration of the compound of the invention. The application area will be determined by the nature of the condition, disorder and/or disease to be treated and/or cared for.

Furthermore, the cosmetic compositions containing the compounds of general formula (I), their stereoisomers, mixtures thereof and/or their cosmetically or pharmaceutically acceptable salts can be used in different types of formulations for oral administration, preferably in the form of oral cosmetic or drugs, such as and not restricted to, capsules, including gelatin capsules, soft capsules, hard capsules, tablets, including sugar coated tablets, pills, powders, granules, chewing gum, solutions, suspensions, emulsions, syrups, elixirs, polysaccharide films, jellies or gelatins, and any other form known by the person skilled in the art. In a particular embodiment, the compounds of the invention can be incorporated into any form of functional food or fortified food, such as and not restricted to, dietary bars or compact or non-compact powders. These powders can be dissolved in water, soda, dairy products, soy derivatives or can be incorporated into dietary bars. The compounds of this invention can be formulated with common excipients and adjuvants for oral compositions or food supplements, such as and not restricted to, fat components, aqueous components, humectants, preservatives, texturizing agents, flavors, aromas, antioxidants and colorants common in the food industry.

Cosmetic or pharmaceutical compositions containing the compounds of general formula (I), their stereoisomers, mixtures thereof and/or their cosmetically or pharmaceutically acceptable salts can also be administered, as well as by topical or transdermal route, by any other appropriate route, such as oral or parenteral route, for which they will include the pharmaceutically acceptable excipients necessary for the formulation of the desired administration form. In the context of this invention, the term "parenteral" includes nasal, auricular, ophthalmic, rectal, urethral, vaginal, subcutaneous, intradermal, intravascular injections such as intravenous, intramuscular, intraocular, intravitreous, intracorneal, intraspinal, intramedullary, intracranial, intracervical, intracerebral, intrameningeal, intraarticular, intrahepatic, intrathoracic, intratracheal, intrathecal and intraperitoneal, and any another similar injection or infusion technique. A person skilled in the art knows the different means by which the cosmetic or pharmaceutical compositions which contain the compounds of the invention can be administered.

Among the cosmetically or pharmaceutically acceptable excipients and/or adjuvants contained in the cosmetic or pharmaceutical compositions described in this invention are additional ingredients commonly used in cosmetic or pharmaceutical compositions, such as and not restricted to, other agents which inhibit neuronal exocytosis, other anticholinergic agents, other agents which inhibit muscular contraction, other anti-aging agents, other anti-wrinkle agents, other antiperspirant agents, other anti-inflammatory agents and/or analgesics, other anti-itching agents, calming agents, anesthetic agents, inhibitors of acetylcholine-receptor aggregation, agents that inhibit acetylchloinesterase, skin relaxant agents, melanin synthesis stimulating or inhibiting agents, whitening or depigmenting agents, propigmenting agents, self-tannin agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, anti-glycation agents, antihistamine agents, antiviral agents, antiparasitic agents, emulsifiers, emollients, organic solvents, liquid propellants, skin conditioners, humectants, substances that retain moisture, alpha hydroxy acids, beta hydroxy acids, moisturizers, epidermal hydrolytic enzymes, vitamins, amino acids, proteins, pigments or colorants, dyes, biopolymers, gelling polymers, thickeners, surfactants, softening agents, emulsifiers, binding agents, preservatives, agents able to reduce or treat the bags under the eyes, exfoliating agents, keratolytic agents, flaking agents, antimicrobial agents, antifungal agents, fungistatic agents, bactericidal agents, bacteriostatic agents, agents stimulating the synthesis of dermal or epidermal macromolecules and/or capable of inhibiting or preventing or delaying their degradation, collagen synthesis-stimulating agents, elastin synthesis-stimulation agents, decorin synthesis-stimulation agents, laminin sysnthesis-stimulation agents, defensin sysnthesis-stimulation agents, chaperone synthesis-stimulation agents, cAMP synthesis-stimulation agents, AQP-3 modulating agents, aquaporin synthesis modulating agents, proteins from the aquaporin family, hyaluronic acid synthesis-stimulation agents, glycosaminoglycan synthesis-stimulation agents, fibronectin synthesis-stimulation agents, sirtuin synthesis-stimulation agents, sirtuin activating agents, heat shock proteins, heat shock protein synthesis-stimulation agents, agents stimulating the synthesis of lipids and components of the stratum corneum, ceramides, fatty acids, agents that inhibit collagen degradation, matrix metalloproteinase inhibitory agents, agents that inhibit elastin degradation, agents that inhibit serine proteases such as kallikreins, leukocyte elastase or cathepsin G, agents stimulating fibroblast proliferation, agents stimulating keratinocyte proliferation, agents stimulating adipocyte proliferation, agents stimulating melanocyte proliferation, agents stimulating keratinocyte differentiation, agents stimulating or delaying adipocyte differentiation, antihyperkeratosis agents, comedolytic agents, anti-psoriasis agents, DNA repair agents, DNA protecting agents, stabilizers, agents for the treatment and/or care of sensitive skin, firming agents, anti-stretch mark agents, binding agents, agents regulating sebum production, lipolytic agents or agents stimulating lipolysis, adipogenic agents, agents modulating PGC-1α expression, agents modulating the activity of PPARγ agents which increase or reduce the triglyceride content of adipocytes, anti-cellulite agents, agents which inhibit the activity of PAR-2, agents stimulating healing, coadjuvant healing agents, agents stimulating reepithelialization, coadjuvant reepithelialization agents, cytokine growth factors, agents acting on capillary circulation and/or microcirculation, agents stimulating angiogenesis, agents that inhibit vascular permeability, venotonic agents, agents acting on cell metabolism agents to improve dermal-epidermal junction, agents inducing hair growth, hair growth inhibiting or retardant agents, hair loss retardant agents, preservatives, perfumes, cosmetic and/or absorbent and/or body odor masking deodorants, chelating agents, plant extracts, essential oils, marine extracts, agents obtained from a biotechnological process, mineral salts, cell extracts, sunscreens and organic or mineral photoprotective agents active against ultraviolet A and/or B rays and/or infrared A rays, or mixtures thereof, provided that they are physically and chemically compatible with the rest of components in the composition and particularly with the compounds of the invention. Likewise, the nature of these additional ingredients should not unacceptably alter the benefits of the compounds of this invention. The nature of these additional ingredients can be synthetic or natural, such as plant extracts, or come from a biotechnological procedure, or from a combination of a synthetic procedure and a biotechnological procedure. Additional examples can be found in *CTFA International Cosmetic Ingredient Dictionary & Handbook, 12th Edition* (2008). In the context of this invention, biotechnological procedure is understood to be any procedure to produce the active ingredient, or part of it, in an organism, or in part of it.

An additional aspect of this invention refers to a cosmetic or pharmaceutical composition which comprises a cosmetically or pharmaceutically effective quantity of at least one compound general formula (I), its stereoisomers, mixtures thereof and/or its cosmetically or pharmaceutically acceptable salts, as well as a cosmetically or pharmaceutically effective quantity of at least one extract, synthetic compound or product of biotechnological origin which is an antiwrinkle agent and/or anti-aging agent such as and not restricted to the extracts or hydrolyzed extracts of *Vitis vinifera, Rosa canina, Curcuma longa, Theobroma cacao, Ginkgo biloba, Leontaopodium alpinum* or *Dunaliella salina* among others. Matrixyl® [INCI: Palmitoyl Pentapeptide-4], Matrixyl® 3000® [INCI: Palmitoyl Tetrapeptide-7, Palmitoyl Oligopeptide], Matrixyl® Synthe'6™ [INCI: Glycerin, Water, Hydroxypropyl Cyclodextrin, Palmitoyl Tripeptide-38], Essenskin™ [INCI: calcium hydroxymethionine], Renovage [INCI: teprenone], Resistem™ [INCI: Globularia Cordifolia Ferment] or Dermaxyl® [INCI: Palmitoyl Oligopeptide] marketed by Sederma/Croda, Vialox® [INCI: Pentapeptide-3], Syn® Ake® [INCI: Dipeptide Diaminobutyroyl Benzylamide Diacetate], Syn®-Coll [INCI: Palmitoyl Tripeptide-5], Phytaluronate [INCI: Locust Bean (*Ceratonia siliqua*) Gum] or Preregen® [INCI: *Glycine soja* (Soybean) Protein, Oxido Reductases] marketed by Pentapharm/DSM, Myoxinol™ [INCI: Hydrolyzed *Hibiscus esculentus* Extract], Syniorage™ [INCI: Acetyle Tetrapeptide-11], Dermican™ [INCI: Acetyl Tetrapeptide-9] or DN AGE™ LS [INCI: *Cassia alata* leaf Extract] marketed by Laboratoires Sérobiologiques/Cognis/BASF, Algisum C® [INCI: Methylsilanol Mannuronate] or Hydroxyprolisilane CN® [INCI: Methylsilanol Hydroxyproline Aspartate] marketed by Exsymol, Argireline® [INCI: Acetyl Hexapeptide-8], SNAP-7 [INCI: Acetyl Heptapeptide-4], SNAP-8 [INCI: Acetyl Octapeptide-3], Leuphasyl® [INCI: Pentapeptide-18], Inyline™ [INCI: Acetyl Hexapeptide-30], Aldenine® [INCI: Hydrolyzed Wheat Protein, Hydrolyzed Soy Protein, Tripeptide-1], Preventhelia™ [INCI: Diaminopropionoyl Tripeptide-33], Decorinyl® [INCI: Tripeptide-10 Citrulline], Decorinol® [INCI: Tripeptide-9 Citrulline], Trylagen® [INCI: Pseudoalteromonas Ferment Extract, Hydrolyzed Wheat Protein, Hydrolyzed Soy Protein, Tripeptide-10 Citrulline, Tripeptide-1], Eyeseryl® [INCI: Acetyl Tetrapeptide-5], Peptide AC29 [INCI: Acetyl Tripeptide-30 Citrulline], Relistase™ [INCI: Acetylarginyltriptophyl Diphenylglycine], Thermostressine® [INCI: Acetyle Tetrapeptide-22], Lipochroman™ [INCI: Dimethylmethoxy Chromanol], Chromabright™ [INCI: Dimethylmethoxy Chromanyl Palmitate], Antarcticine® [INCI: pseudoalteromonas Ferment Extract], dGlyage™ [INCI: Lysine HCl, Lecithin, Tripeptide-9 Citrulline], Vilastene™ [INCI: Lysine HCl, Lecithin, Tripeptide-10 Citrulline], Hyadisine™ [INCI: Pseudoalteromonas Ferment Extract], Hyanify™ [proposed INCI: Saccharide Isomerate], Diffuporine™ [INCI: Acetyl Hexapeptide-37], Silusyne™ [INCI: Soybean (*Glycine Soja*) Oil, Sorbitan Sesquioleate, Isohexadecane, Sodium Hyaluronate, Lauryldimonium Hydroxypropyl Hydrolyzed Soy Protein, Acetyl Hexapeptide-3] or Adifyline™ [INCI: Acetyl Hexapeptide-38] marketed by Lipotec, Kollaren® [INCI: Tripeptide-1, Dextran] marketed by Institut Europeen de Biologie Cellulaire, Collaxyl® IS [INCI: Hexapeptide-9], Laminixyl IS™ [INCI: Heptapeptide], Orsirtine™ GL [INCI: *Oryza sativa* (Rice) Extract], D'Orientine™ IS [INCI: *Phoenix dactylifera* (Date) Seed Extract], Phytoquintescine™ [INCI: Einkorn (*Triticum monococcum*) Extract] or Quintescine™ IS [INCI: Dipeptide-4] marketed by Vincience/ISP/Ashland, BONT-L-Peptide [INCI: Palmitoyl Hexapeptide-19] marketed by Infinitec Activos, Deepaline™ PVB [INCI: Palmitoyl hydrolyzed Wheat Protein] or Sepilift® DPHP [INCI: Dipalmitoyl Hydroxyproline] marketed by Seppic, Gatuline® Expression [INCI: *Acemella oleracea* Extract], Gatuline® In-Tense [INCI: *Spilanthes acemella* Flower Extract] or Gatuline® Age Defense 2 [INCI: *Juglans regia* (Walnut) Seed Extract] marketed by Gattefossé, Thalassine™ [INCI: Algae Extract] marketed by Biotechmarine, ChroNOline™ [INCI: Caprooyl Tetrapeptide-3] or Thymulen-4 [INCI: Acetyl Tetrapeptide-2] marketed by Atrium/Unipex Innovations, EquiState [INCI: *Pyrus malus* Fruit Extract, *Glycine soja* Seed Extract] or Juvenesce [INCI: Ethoxydiglicol and Caprylic Triglycerid, Retinol, Ursolic Acid, Phytonadione, Ilomastat] marketed by Coletica/Engelhard/BASF, Ameliox [INCI: Carnosine, Tocopherol, *Silybum marianum* Fruit Extract] or PhytoCellTec *Malus Domestica* [INCI: *Malus domestica* Fruit Cell Culture] marketed by Mibelle Biochemistry, Bioxilift [INCI: *Pimpinella anisum* Extract] or SMS Anti-Wrinkle® [INCI: *Annona squamosa* Seed Extract] marketed by Silab, antagonists of the $Ca^{2+}$ channel such as and not restricted to, alverine, manganese or magnesium salts, certain secondary or tertiary amines, retinol and its derivatives, idebenone and its derivatives, Coenzyme Q10 and its derivatives, boswellic acid and its derivatives, GHK and its derivatives, carnosine and its derivatives, DNA repair enzymes such as and not restricted to, photolyase or T4 endonuclease V, or chloride channel agonists among others and/or mixtures thereof.

An additional aspect of this invention relates to a cosmetic or pharmaceutical composition which comprises a cosmetically or pharmaceutically effective amount of at least one compound of general formula (I), its stereoisomers, mixtures thereof and/or its cosmetically or pharmaceutically acceptable salts, and, in addition, a cosmetically or pharmaceutically effective amount of at least one natural extract or essential oil which is an anti-itching agent, for example and not restricted to, extracts of *Abelmoschus esculentus, Actaea alba, Aglala odorata, Alkanna tinctoria, Althaea officinalis, Altingia excelsa, Andropogon virginicus, Aralia nudicaulis, Aralia racemosa, Argemone mexicana, Barleria prionitis, Camelia sinensis, Caesalpinia digyna, Campsis grandiflora, Carissa congesta, Carthamus oxyacantha, Cassia tora, Chrysanthemum indicum, Cimicifuga racemosa, Cinnamomum camphora, Clematis vitalba, Cuscuta reflexa, Diospyros peregrina, Enicostema axillare, Hammamelis virginiana, Jatropha multifida, Lavandula officinalis, Lavandula latifolia, Liquidambar orientalis, Lithospermum officinale, Madhuca longifolia, Martynia annua, Medicago sativa, Michelia champaca, Mikania glomerate, Mimosa pudica, Oryza sativa, Phaseolus vulgaris, Phyllanthus urinaria, Phyllanthus virgatus, Pistacia vera, Polygonum hydropiper, Quercus ilex, Rauvolfia caffra, Ricinus communis, Rubus idaeus, Sagittaria sagittifolia, Sandoricum koetjape, Sapindus mukorrossi, Schleichera oleosa, Sesbania grandiflora, Spondias dulcis, Tilia* sp., *Toona ciliata, Tragia involucrata, Trichosanthes quinquangulata, Vaccaria pyramidata, Ventilago madraspatana, Veratrum album* or *Xanthium strumarium* among others or as well as at least one synthetic compound or product of biotechnological origin which is an anti-itching agent, for example and not restricted to, mepyramine (pyrilamine), antazoline, diphenhydramine, carbinoxamine, doxylamine, clemastine, dimenhydrinate, pheniramine, chlorphenamine (chlorpheniramine), deschlorpheniramine, bronpheniramine, triprolidine, cyclizine, chlorcyclizine, hydroxyzine, meclizine, cetirizine, levocetirizine, promethazine, thenaldine, alimemazine (trimeprazine), cyproheptaidne, azatidine, ketoifen, acrivastine, astemizole, cetirizine, loratadine, desloratadine, mizolastine, terfenadine, fexofenadine, azelastine, levocabastine, olopatadine, corticosteroids such as cortisone, hydrocortisone, dexamethasone, prednisone; Neutrazen™ [INCI: Water, Butylene Glycol, Dextran, Palmitoyl Tripeptide-8] marketed by Atrium/Unipex Innovations, Meliprene® [INCI: Dextran, Acetil Heptapeptide-1] marketed by Institut Européen de Biologie Cellulaire/Unipex Innovations, Delisens™ [proposed INCI: Acetyl hexapeptide-46] marketed by Lipotec, Skinasensyl™ [INCI: Acetyl Tetrapeptide-15] marketed by Laboratoires Sérobiologiques/Cognis/BASF, SymSitive® 1609 [INCI: 4-t-Butylcyclohexanol] marketed by Symrise, Symbiocell™ [INCI: Extract from *Cestrum Latifolium*] marketed by BASF, Gatuline® Derma-Sensitive [INCI: Octyldodecyl Myristate, Capparis Spinosa Fruit Extract] marketed by Gattefossé or MAXnolia [INCI: Magnolia Officinalis Bark Extract, *Vitis Vinifera/Vitis Vinifera* (Grape) Seed Extract, Tocopherol] marketed by Mibelle Biochemistry among others, or mixtures thereof.

An additional aspect of this invention relates to a cosmetic or pharmaceutical composition containing a cosmetically or pharmaceutically effective quantity of at least one compound of general formula (I), its stereoisomers, mixtures thereof and/or its cosmetically or pharmaceutically acceptable salts, and also a cosmetically or pharmaceutically effective amount of at least one anti-inflammatory agent and/or analgesic selected, for example and not restricted to, from the group formed by the extract of madecassoside, extract of echinacin, amaranth seed oil, sandalwood oil, peach tree leaf extract, extract of *Aloe vera, Arnica montana, Artemisia vulgaris, Asarum maximum, Calendula officinalis, Capsicum, Centipeda cunninghamii, Chamomilla recutita, Crinum asiaticum, Hamamelis virginiana, Harpagophytum procumbens, Hypericum perforatum, Lilium candidum, Malva sylvestris, Melaleuca alternifolia, Origanum majorana, Origanum vulgare, Prunus laurocerasus, Rosmarinus officialis, Salix alba, Silybum marianum, Tanacetum parthenium, Thymus vulgaris, Uncaria guianensis* or *Vaccinum myrtillus*, mometasone furoate, prednisolone, non-steroidal anti-inflammatory drugs including cyclooxygenase or lipoxygenase inhibitors, benzydamine, acetylsalicylic acid, rosmarinic acid, ursolic acid, glycyrrhizinate derivatives, α-bisabolol, azulene and analogs, sericoside, ruscogenin, escin, escoline, rutin and analogs, hydrocortisone, clobetasol, dexamethasone, halobetasol, diflorasone, fluocinonide, amicinonide, triamcinolone, fluticasone, fluocinolone, flurandrenolide, prednicarbate, prednisone, paracetemol, amoxiprin, benorilate, choline salicylate, faislamine, methyl salicylate, magnesium salicylate, salsalate, diclofenac, aceclofenac, acemetacin, bromfenac, etodolac, indomethacin, oxamethacin, proglumetacin, sulindac, tolmetin, ibuprofen, dexibuprofen, carprofen, fenbufen, fenoprofen, flurbiprofen, ketoprofen, dexketoprofen, ketorolac, loxoprofen, naproxen, miroprofen, oxaprozin, pranoprofen, tiaprofenic acid, suporfen, mefenamic acid, meclofenamate, meclofenamic acid, flufenamic acid, tolfenamic acid, nabumetone, phenylbutazone, azapropazone, clofezone, kebuzone, metamizole, mofebutazone, oxyphenbutazone, phenazone, sulfinpyrazone, piroxicam, lornoxicam, meloxicam, tenoxicam, celecoxib, etoricoxib, lumiracoxib, parecoxib, rofecoxib, valdecoxib, nimesulide, naproxcinod, fluproquazone or licofelone, omega-3 and omega-6 fatty acids, morphine, codeine, oxycodone, hydrocodone, diamorphine, pethidine, tramadol, buprenorphine, benzocaine, lidocaine, chloroprocaine, tetracaine, procaine, amitriptyline, carbamazepine, gabapentine, pregabaline, bisabolol, Neutrazen™ [INCI: Water, Butylene Glycol, Dextran, Palmitoyl Tripeptide-8] marketed by Atrium/Unipex Innovations, Delisens™ [proposed INCI: Acetyl Hexapeptide-46] marketed by Lipotec, Meliprene® [INCI: Dextran, Acetyl Heptapeptide-1] marketed by Institut Européen de Biologie Cellutaire/Unipex Innovations, Skinasensyl™ [INCI: Acetyl Tetrapeptide-15] or Anasensyl™ [INCI: Mannitol, Ammonium Glycyrrhizate, Caffeine, Hippocastanum (horse Chestnut) Extract] marketed by Laboratoires Serobiologiques/Cognis/BASF, Calmosensine™ [INCI: Acetyle Dipeptide-1] marketed by Sederma/Croda, coenzyme Q10 or alkylglycerin ethers, among others, or mixtures thereof.

Another additional aspect of this invention relates to a cosmetic or pharmaceutical composition containing a cosmetically or pharmaceutically effective quantity of at least one compound of general formula (I), its stereoisomers, mixtures thereof and/or its cosmetically or pharmaceutically acceptable salts, and also a cosmetically or pharmaceutically effective amount of at least one agent which inhibits neuronal exocytosis, antichlolinergic agent, inhibitor of acetylcholine-receptor aggregation and/or a muscle contraction inhibitor selected, for example and not restricted to, from the group formed by extracts of *Atropa belladonna, Hyoscyamus niger, Mandragora officinarum, Chondodendron tomentosum*, plants from the *Brugmansias* genus, or from the *Daturas* genus, *Clostridium botulinum* toxin, peptides derived from the protein SNAP-25, peptides derived from the protein synaptotagmin, peptides derived from the protein syntaxin, peptides derived from the protein synaptobrevin, peptides derived from the protein snapin, baclofen, carbidopa, levodopa, bromocriptine, chlorphenesin, chlorzoxazone, donepezil, mephenoxalone, reserpine, tetrabenazine, dantrolene, thiocolchicoside, tizanidine, chlonidine, procyclidine, glycopyrrolate, atropine, hyoscyamine, benztropine, scopolamine, prometazine, diphenhydramine, dimenhydrinate, dicyclomine, cyclobenzaprine, orphenadrine, flavoxate, cyclopentolate, ipratropium, oxybutynin, pirenzepine, tiotropium, trihexyphenidyl, tolterodine, tropicamide, solifenacin, darifenacin, mebeverine, trimethaphan, atracurium, cisatracurium, doxacurium, fazadinium, metocurine, mivacurium, pancuronium, pipecuronium, rapacuronium, tubocuranine, dimethyl tubocuranine, rocuronium, vecuronium, suxamethonium, 18-methoxycoronaridine, carisoprodol, febarbamate, meprobamate, metocarbamol, phenprobamate, tibamate, anticonvulsant agents such as levetiracetam, stiripentol, phenobarbital, methylphenobarbital, pentobarbital, metarbital, barbexaclone, primidone, carbamazepine, oxcarbazepine, benzodiazepines, for example and not restricted to, clonazepam, cloxazolam, clorazepate, diazepam, fluotprazepam, lorazepam, midazolam, nitrazepam, nimetazepam, fenazepam, temazepam, tetrazepam, clobazam, Argireline® [INCI: Acetyl Hexapeptide-8], SNAP-7 [INCI: Acetyl Heptapeptide-4], SNAP-8 [INCI: Acetyle Octapeptide-3], Leuphasyl®[INCI: Pentapeptide-18] or Inyline™ [INCI: Acetyl Hexapeptide-30] marketed by Infinitec Activos, and Vialox® [INCI: Pentapeptide-3] or Syn® Ake® [INCI: Dipeptide Diaminobutyroyl Benzylamide Diacetate] marketed by Pentapharm/DSM among others, or mixtures thereof.

Another additional aspect of this invention relates to a cosmetic or pharmaceutical composition containing a cosmetically or pharmaceutically effective quantity of at least one compound of general formula (I), its stereoisomers, mixtures thereof and/or its cosmetically or pharmaceutically acceptable salts, and also a cosmetically or pharmaceutically effective amount of at least one cosmetic and/or absorbent and/or body odor masking deodorant and/or antiperspirant agent, perfume and/or perfumed oil selected, for example and not restricted to, from the group formed by the complex zinc salt of ricinoleic acid, derived from abiotic acid, salvia essence, chamomile essence, carnation essence, lemon balm essence, mint essence, cinnamon leaf essence, lime blossom essence, juniper berry essence, vetiver essence, frankincense essence, galbanum essence, labdanum essence, lavender essence, peppermint essence, benzoin, bergamot, dihydromyrcenol, lilial, lyral, cintronellol, lemon essence, mandarin essence, orange essence, lavender essence, muscatel, geranium bourbon essence, aniseed, cilantro, cumin, juniper, extracts of fleur-de-lis, lily, roses, jasmine, neroli, benzyl acetate, p-tert-butylcyclohexyl acetate, linalyl acetate, phenylethyl acetate, ethylmethylphenyl glycinate, linalyl benzoate, benzyl formiate, alylcyclohexyl propionate, stiralyl propionate, benzyl salicylate, benzylethylether, linear alkanes with from 8 to 18 carbon atoms, citral ricinoleic acid, citronellal, citronellyl oxyacetaldehyde, cyclamen aldehyde, hydroxycitronellal, bourgeonal, ionones, methyl cedryl ketone, anethole, eugenol, isoeugenol, geraniol, linalool, terpineol, phenylethylalcohol, α-hexylcinnamaldehyde, geraniol, benzylacetone, cyclamenaldehyde, ambroxan, indole, hedione, sandelice, cyclovertal, β-damascone, allyl amyl glycolate, dihydromyrcenol, phenoxyethyl isobutyrate, cyclohexyl salicylate, phenylacetic acid, geranyl acetate, romilate, irotyl, floramate, aluminum salts such as alum, aluminum chloride, aluminum chlorohydrate, aluminum dichlorohydrate, aluminum sesquichlorohydrate, aluminum hydroxy allantoinate, aluminum sesquichlorohydrate, aluminum hydroxy allantionate, aluminum chlorotartrate, aluminum and zirconium trichlorohydrate, aluminum and zirconium tetrachlorohydrate, aluminum and zirconium pentachlorohydrate and/or mixtures thereof, Leuphasyl® [INCI: Pentapeptide-18], SNAP-7 [INCI: Acetyl Heptapeptide-4], SNAP-8 [INCI: Acetyl Ocatapeptide-3], Argireline® [INCI: Acetyl Hexapeptide-8] or Inyline™ [INCI: Acetyle Hexapeptide-30] marketed by Lipotec, Vialox® [INCI: Pentapeptide 3] or Syn® Ake® [INCI: Dipeptide Diaminobutyroyl Benzylamide Diacetate] marketed by Pentapharm/DSM and BONT-L-Peptide [INCI: Palmitoyl Hexapeptide-19] marketed by Infinitec Activos among others, or mixtures thereof.

Applications

In another aspect, this invention relates to a compound of general formula (I):

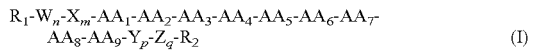

its stereoisomers, mixtures thereof and/or its cosmetically or pharmaceutically acceptable salts, characterized in that:
  $AA_1$ is selected from the group formed by -Arg-, -His-, -Lys-, -Gln-, -Asn-, -Glu- and -Asp-;
  $AA_2$ is selected from the group formed by -Arg-, -His-, -Lys-, -Gln-, -Asn-, -Glu- and -Asp-;
  $AA_3$ is selected from the group formed by -Leu-, -Ile-, -Val-, -Met-, -MetO-, -MetO$_2$-, -Glu-, -Asp-, -Phe-, -Trp- and -Tyr-;
  $AA_4$ is selected from the group formed by -Lys-, -His-, -Glu-, and -Asp-;
  $AA_5$ is selected from the group formed by -Arg-, -His-, -Lys-, -Gln-, -Asn-, -Glu- and -Asp-;
  $AA_6$ is selected from the group formed by -Met-, -MetO-, -MetO$_2$-, -Ile-, -Leu-, -Val-, -His-, -Lys- and -Arg-;
  $AA_7$ is selected from the group formed by -Met-, -MetO-, and -MetO$_2$-;
  $AA_8$ is selected from the group formed by -Glu-, -Asp-, -Gly-, -Ala-, and -Pro-;
  $AA_9$ is selected from the group formed by -Gln-, -Asn- or a bond;
  W, X, Y, Z are amino acids and are independently selected from amongst themselves;
  n, m, p and q are independently selected from amongst themselves and have a value of 0 or 1;
  n+m+p+q is smaller or equal to 2;

with the condition that if $AA_1$ is -Arg-, $AA_2$ is -Gln-, $AA_3$ is -Leu-, $AA_4$ is -Glu-, $AA_5$ is -His-, $AA_6$ is -Val- and $AA_9$ is a bond, then $AA_8$ is selected from the group formed by -Glu-, -Gly-, -Ala- and -Pro-;
and with the condition that if X is -Asn-, $AA_1$ is -Lys-, $AA_2$ is -Arg-, $AA_3$ is -Phe-, $AA_4$ is -His-, $AA_5$ is -Asn-, $AA_6$ is -Ile-, $AA_8$ is -Gly- and $AA_9$ is a bond, n is 0, then Y or Z are not -Arg-;
  $R_1$ is selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group formed by H, substituted or unsubstituted non-cyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;
  $R_2$ is selected from the group formed by —$NR_3R_4$, —$OR_3$ and —$SR_3$ wherein $R_3$ and $R_4$ are independently selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and
  $R_1$ and $R_2$ are not α-amino acids,
for its use in medicine.

In another aspect, the invention relates to a compound of general formula (I):

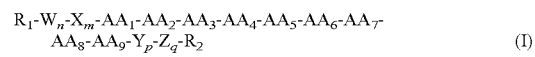

its stereoisomers, mixtures thereof and/or its cosmetically or pharmaceutically acceptable salts, characterized in that:
  $AA_1$ is selected from the group formed by -Arg-, -His-, -Lys-, -Gln-, -Asn-, -Glu- and -Asp-;
  $AA_2$ is selected from the group formed by -Arg-, -His-, -Lys-, -Gln-, -Asn-, -Glu- and -Asp-;
  $AA_3$ is selected from the group formed by -Leu-, -Ile-, -Val-, -Met-, -MetO-, -MetO$_2$-, -Glu-, -Asp-, -Phe-, -Trp- and -Tyr-;
  $AA_4$ is selected from the group formed by -Lys-, -His-, -Glu-, and -Asp-;
  $AA_5$ is selected from the group formed by -Arg-, -His-, -Lys-, -Gln-, -Asn-, -Glu- and -Asp-;
  $AA_6$ is selected from the group formed by -Met-, -MetO-, -MetO$_2$-, -Ile-, -Leu-, -Val-, -His-, -Lys- and -Arg-;
  $AA_7$ is selected from the group formed by -Met-, -MetO-, and -MetO$_2$-;
  $AA_8$ is selected from the group formed by -Glu-, -Asp-, -Gly-, -Ala-, and -Pro-;
  $AA_9$ is selected from the group formed by -Gln-, -Asn- or a bond;
  W, X, Y, Z are amino acids and are independently selected from amongst themselves;
  n, m, p and q are independently selected from amongst themselves and have a value of 0 or 1;
  n+m+p+q is smaller or equal to 2;
  $R_1$ is selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group formed by H, substituted or unsubstituted non-cyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;

$R_2$ is selected from the group formed by —$NR_3R_4$, —$OR_3$ and —$SR_3$ wherein $R_3$ and $R_4$ are independently selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and $R_1$ and $R_2$ are not α-amino acids, for its use in the treatment and/or prevention, delay, or hindering of pain, inflammation, itching, hyperhidrosis and/or of neurological, compulsive and/or neurophsychiatric diseases and/or disorders which are improved by the inhibition of neuronal exocytosis, selected from the group formed by muscular spasticity, dystonia, focal dystonia, blepharospasm, torsion dystonia, cervical dystonia or torticollis laryngeal dystonia or spasmodic dysphonia, oromandibular dystonia, extremity dystonia, writer's cramp, musician's cramp, foot dystonia, bruxism, facial scoliosis, hemifacial spasm, tics, strabismus, segmentary dystonia, Meige's syndrome, multifocal dystonia, hemidystonia, dopamine-responsive dystonia, Segawa's dystonia, trembling, Parkinson's disease, nerve impingements, Alzheimer's disease and Tourette's syndrome.

In another aspect, the invention relates to a compound of general formula (I):

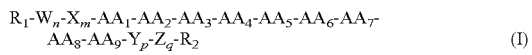

(I)

its stereoisomers, mixtures thereof and/or its cosmetically or pharmaceutically acceptable salts, characterized in that:

$AA_1$ is selected from the group formed by -Arg-, -His-, -Lys-, -Gln-, -Asn-, -Glu- and -Asp-;

$AA_2$ is selected from the group formed by -Arg-, -His-, -Lys-, -Gln-, -Asn-, -Glu- and -Asp-;

$AA_3$ is selected from the group formed by -Leu-, -Ile-, -Val-, -Met-, -MetO-, -MetO$_2$-, -Glu-, -Asp-, -Phe-, -Trp- and -Tyr-;

$AA_4$ is selected from the group formed by -Lys-, -His-, -Glu-, and -Asp-;

$AA_5$ is selected from the group formed by -Arg-, -His-, -Lys-, -Gln-, -Asn-, -Glu- and -Asp-;

$AA_6$ is selected from the group formed by -Met-, -MetO-, -MetO$_2$-, -Ile-, -Leu-, -Val-, -His-, -Lys- and -Arg-;

$AA_7$ is selected from the group formed by -Met-, -MetO-, and -MetO$_2$-;

$AA_8$ is selected from the group formed by -Glu-, -Asp-, -Gly-, -Ala-, and -Pro-;

$AA_9$ is selected from the group formed by -Gln-, -Asn- or a bond;

W, X, Y, Z are amino acids and are independently selected from amongst themselves;

n, m, p and q are independently selected from amongst themselves and have a value of 0 or 1;

n+m+p+q is smaller or equal to 2;

$R_1$ is selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group formed by H, substituted or unsubstituted non-cyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;

$R_2$ is selected from the group formed by —$NR_3R_4$, —$OR_3$ and —$SR_3$ wherein $R_3$ and $R_4$ are independently selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and $R_1$ and $R_2$ are not α-amino acids, for its use in the treatment of skin, hair and/or mucous membranes.

In another aspect, the invention relates to a compound of general formula (I):

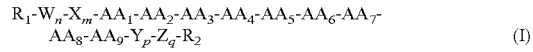

(I)

its stereoisomers, mixtures thereof and/or its cosmetically or pharmaceutically acceptable salts, characterized in that:

$AA_1$ is selected from the group formed by -Arg-, -His-, -Lys-, -Gln-, -Asn-, -Glu- and -Asp-;

$AA_2$ is selected from the group formed by -Arg-, -His-, -Lys-, -Gln-, -Asn-, -Glu- and -Asp-;

$AA_3$ is selected from the group formed by -Leu-, -Ile-, -Val-, -Met-, -MetO-, -MetO$_2$-, -Glu-, -Asp-, -Phe-, -Trp- and -Tyr-;

$AA_4$ is selected from the group formed by -Lys-, -His-, -Glu-, and -Asp-;

$AA_5$ is selected from the group formed by -Arg-, -His-, -Lys-, -Gln-, -Asn-, -Glu- and -Asp-;

$AA_6$ is selected from the group formed by -Met-, -MetO-, -MetO$_2$-, -Ile-, -Leu-, -Val-, -His-, -Lys- and -Arg-;

$AA_7$ is selected from the group formed by -Met-, -MetO-, and -MetO$_2$-;

$AA_8$ is selected from the group formed by -Glu-, -Asp-, -Gly-, -Ala-, and -Pro-;

$AA_9$ is selected from the group formed by -Gln-, -Asn- or a bond;

W, X, Y, Z are amino acids and are independently selected from amongst themselves;

n, m, p and q are independently selected from amongst themselves and have a value of 0 or 1;

n+m+p+q is smaller or equal to 2;

$R_1$ is selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group formed by H, substituted or unsubstituted non-cyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;

R$_2$ is selected from the group formed by —NR$_3$R$_4$, —OR$_3$ and —SR$_3$ wherein R$_3$ and R$_4$ are independently selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and R$_1$ and R$_2$ are not α-amino acids, for the cosmetic, non-therapeutic treatment and/or care of the skin, hair and/or mucous membranes, in particular for the prevention, delay, or hindering of aging and/or photoaging of the skin, hair and/or mucous membranes, the treatment and/or prevention, delay, or hindering of wrinkles and/or expression wrinkles, treatment and/or prevention, delay, or hindering of perspiration, treatment and/or care of disorders of the skin selected from the group formed by calluses, warts, treatment stimulating hair growth and/or prevention or delay of hair loss.

In another aspect the invention relates to a compound of general formula (I):

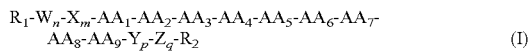

(I)

its stereoisomers, mixtures thereof and/or its cosmetically or pharmaceutically acceptable salts, characterized in that:

AA$_1$ is selected from the group formed by -Arg-, -His-, -Lys-, -Gln-, -Asn-, -Glu- and -Asp-;

AA$_2$ is selected from the group formed by -Arg-, -His-, -Lys-, -Gln-, -Asn-, -Glu- and -Asp-;

AA$_3$ is selected from the group formed by -Leu-, -Ile-, -Val-, -Met-, -MetO-, -MetO$_2$-, -Glu-, -Asp-, -Phe-, -Trp- and -Tyr-;

AA$_4$ is selected from the group formed by -Lys-, -His-, -Glu-, and -Asp-;

AA$_5$ is selected from the group formed by -Arg-, -His-, -Lys-, -Gln-, -Asn-, -Glu- and -Asp-;

AA$_6$ is selected from the group formed by -Met-, -MetO-, -MetO$_2$-, -Ile-, -Leu-, -Val-, -His-, -Lys- and -Arg-;

AA$_7$ is selected from the group formed by -Met-, -MetO-, and -MetO$_2$-;

AA$_8$ is selected from the group formed by -Glu-, -Asp-, -Gly-, -Ala-, and -Pro-;

AA$_9$ is selected from the group formed by -Gln-, -Asn- or a bond;

W, X, Y, Z are amino acids and are independently selected from amongst themselves;

n, m, p and q are independently selected from amongst themselves and have a value of 0 or 1;

n+m+p+q is smaller or equal to 2;

R$_1$ is selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and R$_5$—CO—, wherein R$_5$ is selected from the group formed by H, substituted or unsubstituted non-cyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;

R$_2$ is selected from the group formed by —NR$_3$R$_4$, —OR$_3$ and —SR$_3$ wherein R$_3$ and R$_4$ are independently selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and R$_1$ and R$_2$ are not α-amino acids, for its use in the inhibition of neuronal exocytosis.

Alternatively, in another aspect, the invention relates to a method of treatment and/or prevention, delay, or hindering of pain, inflammation, itching, hyperhidrosis and/or of neurological, compulsive and/or neuropsychiatric diseases and/or disorders which are improved by the inhibition of neuronal exocytosis, selected from the group formed by muscular spasticity, dystonia, focal dystonia, blepharospasm, torsion dystonia, cervical dystonia or torticollis, laryngeal dystonia or spasmodic dysphonia, oromandibular dystonia, extremity dystonia, writer's cramp, musician's cramp, foot dystonia, bruxism, facial scoliosis, hemifacial spasm, tics, strabismus, segmentary dystonia, Meige's syndrome, multifocal dystonia, hemidystonia, dopamine-responsive dystonia, Segawa's dystonia, trembling, Parkinson's disease, nerve impingements, Alzheimer's disease and Tourette's syndrome, which comprises the administration of a cosmetically or pharmaceutically effective quantity of at least one compound of general formula (I):

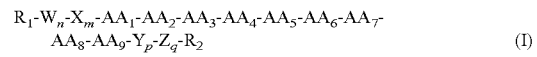

(I)

its stereoisomers, mixtures thereof and/or its cosmetically or pharmaceutically acceptable salts, characterized in that:

AA$_1$ is selected from the group formed by -Arg-, -His-, -Lys-, -Gln-, -Asn-, -Glu- and -Asp-;

AA$_2$ is selected from the group formed by -Arg-, -His-, -Lys-, -Gln-, -Asn-, -Glu- and -Asp-;

AA$_3$ is selected from the group formed by -Leu-, -Ile-, -Val-, -Met-, -MetO-, -MetO$_2$-, -Glu-, -Asp-, -Phe-, -Trp- and -Tyr-;

AA$_4$ is selected from the group formed by -Lys-, -His-, -Glu-, and -Asp-;

AA$_5$ is selected from the group formed by -Arg-, -His-, -Lys-, -Gln-, -Asn-, -Glu- and -Asp-;

AA$_6$ is selected from the group formed by -Met-, -MetO-, -MetO$_2$-, -Ile-, -Leu-, -Val-, -His-, -Lys- and -Arg-;

AA$_7$ is selected from the group formed by -Met-, -MetO-, and -MetO$_2$-;

AA$_8$ is selected from the group formed by -Glu-, -Asp-, -Gly-, -Ala-, and -Pro-;

AA$_9$ is selected from the group formed by -Gln-, -Asn- or a bond;

W, X, Y, Z are amino acids and are independently selected from amongst themselves;

n, m, p and q are independently selected from amongst themselves and have a value of 0 or 1;

n+m+p+q is smaller or equal to 2;

R$_1$ is selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and R$_5$—CO—, wherein R$_5$ is selected from the group formed by H, substituted or unsubstituted non-cyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;

R$_2$ is selected from the group formed by —NR$_3$R$_4$, —OR$_3$ and —SR$_3$ wherein R$_3$ and R$_4$ are independently selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and R$_1$ and R$_2$ are not α-amino acids.

In another aspect, the invention relates to a method of treatment and/or care of the skin, hair and/or mucous membranes which comprises the administration of a cosmetically or pharmaceutically effective quantity of at least compound of general formula (I):

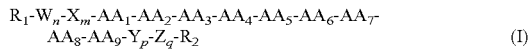

(I)

its stereoisomers, mixtures thereof and/or its cosmetically or pharmaceutically acceptable salts, characterized in that:
  AA$_1$ is selected from the group formed by -Arg-, -His-, -Lys-, -Gln-, -Asn-, -Glu- and -Asp-;
  AA$_2$ is selected from the group formed by -Arg-, -His-, -Lys-, -Gln-, -Asn-, -Glu- and -Asp-;
  AA$_3$ is selected from the group formed by -Leu-, -Ile-, -Val-, -Met-, -MetO-, -MetO$_2$-, -Glu-, -Asp-, -Phe-, -Trp- and -Tyr-;
  AA$_4$ is selected from the group formed by -Lys-, -His-, -Glu-, and -Asp-;
  AA$_5$ is selected from the group formed by -Arg-, -His-, -Lys-, -Gln-, -Asn-, -Glu- and -Asp-;
  AA$_6$ is selected from the group formed by -Met-, -MetO-, -MetO$_2$-, -Ile-, -Leu-, -Val-, -His-, -Lys- and -Arg-;
  AA$_7$ is selected from the group formed by -Met-, -MetO-, and -MetO$_2$-;
  AA$_8$ is selected from the group formed by -Glu-, -Asp-, -Gly-, -Ala-, and -Pro-;
  AA$_9$ is selected from the group formed by -Gln-, -Asn- or a bond
  W, X, Y, Z are amino acids and are independently selected from amongst themselves;
  n, m, p and q are independently selected from amongst themselves and have a value of 0 or 1;
  n+m+p+q is smaller or equal to 2;
  R$_1$ is selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and R$_5$—CO—, wherein R$_5$ is selected from the group formed by H, substituted or unsubstituted non-cyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;

R$_2$ is selected from the group formed by —NR$_3$R$_4$, —OR$_3$ and —SR$_3$ wherein R$_3$ and R$_4$ are independently selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and R$_1$ and R$_2$ are not α-amino acids.

In another aspect the invention relates to a method of inhibition of neuronal exocytosis which comprises the administration of a cosmetically or pharmaceutically effective quantity of at least a compound of general formula (I):

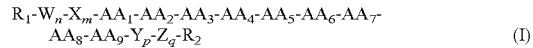

(I)

its stereoisomers, mixtures thereof and/or its cosmetically or pharmaceutically acceptable salts, characterized in that:
  AA$_1$ is selected from the group formed by -Arg-, -His-, -Lys-, -Gln-, -Asn-, -Glu- and -Asp-;
  AA$_2$ is selected from the group formed by -Arg-, -His-, -Lys-, -Gln-, -Asn-, -Glu- and -Asp-;
  AA$_3$ is selected from the group formed by -Leu-, -Ile-, -Val-, -Met-, -MetO-, -MetO$_2$-, -Glu-, -Asp-, -Phe-, -Trp- and -Tyr-;
  AA$_4$ is selected from the group formed by -Lys-, -His-, -Glu-, and -Asp-;
  AA$_5$ is selected from the group formed by -Arg-, -His-, -Lys-, -Gln-, -Asn-, -Glu- and -Asp-;
  AA$_6$ is selected from the group formed by -Met-, -MetO-, -MetO$_2$-, -Ile-, -Leu-, -Val-, -His-, -Lys- and -Arg-;
  AA$_7$ is selected from the group formed by -Met-, -MetO-, and -MetO$_2$-;
  AA$_8$ is selected from the group formed by -Glu-, -Asp-, -Gly-, -Ala-, and -Pro-;
  AA$_9$ is selected from the group formed by -Gln-, -Asn- or a bond;
  W, X, Y, Z are amino acids and are independently selected from amongst themselves;
  n, m, p and q are independently selected from amongst themselves and have a value of 0 or 1;
  n+m+p+q is smaller or equal to 2;
  R$_1$ is selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and R$_5$—CO—, wherein R$_5$ is selected from the group formed by H, substituted or unsubstituted non-cyclic aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;

R$_2$ is selected from the group formed by —NR$_3$R$_4$, —OR$_3$ and —SR$_3$ wherein R$_3$ and R$_4$ are independently selected from the group formed by H, a polymer derived from polyethylene glycol, substituted or unsubstituted non-cyclic aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl; and R$_1$ and R$_2$ are not α-amino acids.

In accordance with a preferred embodiment, R$_1$ is selected from the group formed by H, a polymer derived from polyethylene glycol and R$_5$—CO—, is selected from the group formed by substituted or unsubstituted alkyl radical C$_1$-C$_{24}$, substituted or unsubstituted alkenyl C$_2$-C$_{24}$, substituted or unsubstituted alkynyl C$_2$-C$_{24}$, substituted or unsubstituted cycloalkyl C$_3$-C$_{24}$, substituted or unsubstituted cycloalkenyl $C_5$-$C_{24}$, substituted or unsubstituted cycloalkynyl $C_8$-$C_{24}$, substituted or unsubstituted aryl $C_6$-$C_{30}$, substituted or unsubstituted aralkyl $C_7$-$C_{24}$, substituted or unsubstituted heterocyclyl ring of 3-10 members, and substituted or unsubstituted heteroarylalkyl of 2 to 24 carbon atoms and 1 to 3 atoms other than carbon and an alkyl chain of 1 to 6 carbon atoms and $R_3$—CO is not an α-amino acid. More preferably, $R_1$ is selected from the group formed by H, a polymer derived from polyethylene glycol of a molecular weight comprised between 1200 and 35000 Daltons, acetyl, tert-butanoyl, prenyl, hexanoyl, 2-methylhexanoyl, cyclohexanecarboxyl, octanoyl, decanoyl, lauroyl, myristoyl, palmitoyl, stearoyl, oleoyl and linoleoyl. Even more preferably, $R_1$ is H, acetyl, lauroyl, myristoyl or palmitoyl. In an even more preferably embodiment, $R_1$ is acetyl or palmitoyl.

In accordance with another preferred embodiment, $R_2$ is selected from the group formed by —$NR_3R_4$, —$OR_3$, —$SR_3$, wherein $R_3$ and $R_4$ are independently selected from the group formed by H, a polymer derived from polyethylene glycol, substituted or unsubstituted alkyl $C_1$-$C_{24}$, substituted or unsubstituted alkenyl $C_2$-$C_{24}$, substituted or unsubstituted alkynyl $C_2$-$C_{24}$, substituted or unsubstituted cycloalkyl $C_3$-$C_{24}$, substituted or unsubstituted cycloalkenyl $C_5$-$C_{24}$, substituted or unsubstituted cycloalkynyl $C_8$-$C_{24}$, substituted or unsubstituted aryl $C_6$-$C_{30}$, substituted or unsubstituted aralkyl $C_7$-$C_{24}$, substituted or unsubstituted heterocyclyl ring of 3-10 members, and substituted or unsubstituted heteroarylalkyl of 2 to 24 carbon atoms and 1 to 3 atoms other than carbon wherein the alkyl chain is of 1 to 6 carbon atoms and —$NR_3R_4$ is not an α-amino acid. Optionally, $R_3$ and $R_4$ can be bound by a saturated or unsaturated carbon-carbon bond, forming a cycle with the nitrogen atom, More preferably $R_2$ is —$NR_3R_4$ or —$OR_3$. More preferably, $R_3$ and $R_4$ are selected from the group formed by H, a polymer derived from polyethylene glycol of a molecular weight comprised between 200 and 35000 Daltons, methyl, ethyl, hexyl, dodecyl and hexadecyl. Even more preferably $R_3$ is H and $R_4$ is selected from the group formed by H, methyl, ethyl, hexyl, dodecyl and hexadecyl. In accordance with an even more preferred embodiment, $R_2$ is selected form —OH and —$NH_2$.

In accordance with another preferred embodiment $AA_1$ is selected from the group formed by -Arg-, -His-, -Lys-, -Gln-, -Asn-, -Glu- and -Asp-, $AA_2$ is selected from the group formed by -Arg-, -His-, -Lys-, -Gln-, -Asn-, and -Asp-, $AA_3$ is selected from the group formed by -Leu-, -Met-, -MetO-, -MetO$_2$-, -Glu- and -Phe-, $AA_4$ is selected from the group formed by -His- and -Glu-, $AA_5$ is selected from the group formed by -Arg-, -His-, -Lys-, -Gln-, -Asn-, and -Asp-, $AA_6$ is selected from the group formed by -Ile-, -Lys-, and -Asp-, $AA_7$ is selected from the group formed by -Met-, -MetO-, and -MetO$_2$-, $AA_8$ is selected from the group formed by -Asp-, -Gly-, and -Ala-, $AA_9$ is selected from the group formed by -Gln-, -Asn-, or a bond, with the condition that if $AA_1$ is -Lys-, $AA_1$ is -Arg-, $AA_3$ is -Phe-, $AA_4$ is -His-, $AA_5$ is -Asn-, $AA_6$ is -Ile-, $AA_8$ is -Gly- and $AA_9$ is a bond, then n+m+p+q is equal to 0.

In accordance with another preferred embodiment of this invention $AA_1$ is selected from the group formed by -Arg-, -His-, -Lys-, -Gln-, -Asn-, -Glu- and -Asp-, $AA_2$ is selected from the group formed by -Arg-, -His-, -Lys-, -Gln-, -Asn-, and -Asp-, $AA_3$ is selected from the group formed by -Leu-, -Glu- and -Phe-, $AA_4$ is selected from the group formed by -His- and -Glu-, $AA_5$ is selected from the group formed by -Arg-, -His-, -Lys-, -Gln-, and -Asn-, $AA_6$ is selected from the group formed by -Ile- and -Lys-, $AA_7$ is selected from the group formed by -Met-, -MetO-, and -MetO$_2$-, $AA_8$ is -Asp-, and $AA_9$ is selected from the group formed by -Gln-, -Asn-, or a bond. In a preferred embodiment, n, m p and q are 0.

In accordance with another preferred embodiment $AA_1$ is selected from the group formed by -Arg-, -His-, -Lys-, -Gln-, -Asn-, -Glu- and -Asp-, $AA_2$ is selected from the group formed by -Arg-, -His-, -Lys-, -Gln-, -Asn-, and -Asp-, $AA_3$ is selected from the group formed by -Glu- and -Phe-, $AA_4$ is -His-, $AA_5$ is selected from the group formed by -Arg-, -His-, -Lys-, -Gln- and -Asn-, $AA_6$ is -Lys-, $AA_7$ is selected from the group formed by -Met-, -MetO-, and -MetO$_2$-, $AA_8$ is -Asp-, and $AA_9$ is a bond. More preferably, n, m, p and q are 0.

In accordance with another preferred embodiment $AA_1$ is selected from the group formed by -Gln-, -Asn-, -Glu- and -Asp-, $AA_2$ is selected from the group formed by -Gln-, -Asn-, and -Asp-, $AA_3$ is selected from the group formed by -Leu- and -Glu-, $AA_4$ is -Glu-, $AA_5$ is selected from the group formed by -Arg-, -His-, -Lys-, -Gln-, and -Asn-, $AA_6$ is -Ile-, $AA_7$ is selected from the group formed by -Met-, -MetO-, and -MetO$_2$-, $AA_8$ is -Asp- and $AA_9$ is selected from the group formed by -Gln-, -Asn-. More preferably, $AA_3$ is -Leu-. Even more preferably, n, m, p and q are 0.

In accordance with another even more preferred embodiment of this invention $R_1$ is selected from the group formed by H, acetyl, lauroyl, myristoyl and palmitoyl, $AA_1$ is selected from the group formed by -L-Asn-, -L-Gln-, -L-His and -L-Asp-, $AA_2$ is selected from the group formed by -L-His-, -L-Gln-, and -L-Asn-, $AA_3$ is selected from the group formed by -L-Glu-, -L-Leu-, and -L-Phe-, $AA_4$ is selected from the group formed by -L-His- and -L-Glu-, $AA_5$ is selected from the group formed by -L-Arg-, -L-Gln-, -L-Asn- and -L-His-, $AA_6$ is selected from the group formed by -L-Ile- and -L-Lys-, $AA_7$ is selected from the group formed by -L-Met-, -L-MetO-, and -L-MetO$_2$-, $AA_8$ is -L-Asp-, $AA_9$ is selected from the group formed by -L-Gln-, -L-Asn- or a bond, and $R_2$ is selected from the group formed by —$NR_3R_4$ and —$OR_3$ where $R_3$ and $R_4$ are independently selected from the group formed by —$NR_3R_4$ and —$OR_3$ where $R_3$ and $R_4$ are independently selected from H, methyl, ethyl, hexyl, dodecyl and hexadecyl. More preferably, $R_3$ is acetyl or palmitoyl and $R_2$ is —$NH_2$. Even more preferably, n, m, p and q are 0.

In accordance with another embodiment of this invention $R_1$ is selected from the group formed by H, acetyl, lauroyl, myristoyl and palmitoyl, $AA_1$ is selected from the group formed by -L-Asn-, -L-Gln-, -L-Arg-, -L-Lys-, -L-His-, -L-Glu and -L-Asp-, $AA_2$ is selected from the group formed by -L-Asn-, -L-Gln-, -L-Arg-, -L-Lys-, -L-His- and -L-Asp-, $AA_3$ is selected from the group formed by -L-Glu- and -L-Phe-, $AA_4$ is -L-His-, $AA_5$ is selected from the group formed by -L-Asn-, -L-Gln-, -L-Arg-, -L-Lys- and -L-His-, $AA_6$ is -L-Lys-, $AA_7$ is selected from the group formed by -L-Met-, -L-MetO-, and -L-MetO$_2$-, $AA_8$ is -L-Asp-, $AA_9$ is a bond, and $R_2$ is selected from the group formed by —$NR_3R_4$ and —$OR_3$ where $R_3$ and $R_4$ are independently selected from H, methyl, ethyl, hexyl, dodecyl and hexadecyl. More preferably, $R_1$ is acetyl or palmitoyl and $R_2$ is —$NH_2$. Even more preferably, n, m, p and q are 0.

In accordance with another embodiment of this invention $R_1$ is selected from the group formed by H, acetyl, lauroyl, myristoyl and palmitoyl, $AA_1$ is selected from the group formed by -L-Asn-, -L-Gln-, -L-Glu- and -L-Asp-, $AA_2$ is selected from the group formed by -L-Gln-, -L-Asn-, and -L-Asp-, $AA_3$ is selected from the group formed by -L-Glu- and -L-Leu-, $AA_4$ is -L-Glu-, $AA_5$ is selected from the group formed by -L-Asn-, -L-Gln-, -L-Arg-, -L-Lys- and -L-His-, $AA_6$ is -L-Ile-, $AA_7$ is selected from the group formed by -L-Met-, -L-MetO-, and -L-MetO$_2$-, AA$_8$ is -L-Asp-, AA$_9$ is selected from the group formed by -L-Gln- and -L-Asn-, and R$_2$ is selected from the group formed by —NR$_3$R$_4$ and —OR$_3$ where R$_3$ and R$_4$ are independently selected from H, methyl, ethyl, hexyl, dodecyl and hexadecyl. More preferably, AA$_3$ is -L-Leu-. More preferably, R$_1$ is acetyl or palmitoyl and R$_2$ is —NH$_2$. Even more preferably, n, m, p and q are 0.

In a preferred embodiment, the itching is selected from itching associated with conditions, diseases and/or disorders, for example and not restricted to, dermatitis, atopic dermatitis, contact dermatitis, diaper dermatitis, dermatitis herpetiformis, photodermatosis, photosensitivity, pregnancy related dermatitis, menopause related dermatitis, eczema, sensitive skin, psoriasis, chickenpox, herpes, herpes zoster, Netherton's syndrome, peeling skin syndrome, lichen planus, acne, dandruff, seborrhea, seborrheic dermatitis, alopecia, athlete's foot, candidiasis, hemorrhoids, vaginal itching, perianal itching, angogenital itching, sunburn, hives, pruritic otitis, itchy eyes, senile purritus, aquagenic pruritus, prurigo nodularis, prurigo planus, pityriasis rosea, xerosis and dry skin, or itching associated with dialysis, infection from human immunodeficiency virus, malignant neoplasms, Hodgkin's disease, leukemia, myeloma, lymphoma, solid tumors, adenocarcinoma, lung cancer, hepatic diseases, jaundice, cholestatis, liver failure, cirrhosis, polycythemia, hypereosinophilic syndrome, essential thrombocythemia, myelodysplastic syndrome, iron-deficiency anemia, system lupus erythematosus, endocrine disease, thyroid diseases, hyperthyroidism, hypothyroidism, parathyroid diseases, diabetes mellitus, kidney diseases, kidney failure, uremia, parasitic diseases, scabies, lice, intestinal worms, allergic reactions, allergies to medicines, food allergies, allergies to chemical products, exposure to poisonous plants, exposure to insect bites, chemotherapy, stress and anxiety, among others.

In another particular embodiment, the pain is selected, for example and not restricted to, from the group formed by acute pain, chronic pain, nocicpetive pain, neuorpathic pain, inflammatory pain, visceral pain, abdominal pain, digestive system pain, respiratory system pain, urogenital system pain, endocrine system pain, heart pain, pancreatic pain, liver pain, paid due to gallstones, cholestasis, intestinal pain, stomach pain, pain due to duodenal ulcers, pain due to esophagitis, pain due to gastroesophageal reflux, spleen pain, blood vessel pain, thalamic pain syndrome, irritable bowel syndrome, pain associated with Crohn's disease, pain associated with ulcerative colitis, diverticulitis, gastrointestinal mucositis, headache, tension-type headache, sinusitis-associated headache, migraine, eye pain, dry eye syndrome, post-operative pain, post-operative pain due to surgical incisions, post-operative pain due to bone grafting, post-operative pain due to bone substitution, post-operative pain due to infections, post-operative paid due to limb amputations, pain due to bone fractures, pain due to cancer, pain due to bone cancer, pain associated with benign bone tumors, pain associated with osteoid osteomas, pain associated with osteoblastomas, pain due to cancer treatment, pain due to chemotherapy, pain due to emesis, pain due to emesis as a consequence of chemotherapy treatment, musculoskeletal pain, spastic muscle pain, fibromyalgia, complex regional pain syndrome, psychogenic pain, neuralgic pain, pain due to demyelinating diseases, neck pain associated with cervical dystonia, back pain, lumbago, sciatica, neurogenic inflammation, neuritis, causalgia, touch sensitivity, sensitivity to cold, sensitivity to heat, cutaneous irritation, post-hair removal cutaneous irritation, post-shaving cutaneous irritation, psoriasis, sensitive skin, dermatitis, atopic dermatitis, contact dermatitis, diaper dermatitis seborrheic dermatitis, eczema, lichen planus, burns, sunburn, arthritis, rheumatoid arthritis, osteoarthritis, psoriatic arthritis, uveitis, pain due to nerve lesions, neuralgia, postherpetic neuralgia, neuropathies, peripheral neuropathies, phantom pains, allodynia, hyperalgesia, cold hyperalgesia, pain due to carpal tunnel syndrome, burning pain, Grierson-Gopalan syndrome (better known as burning feet syndrome), burning mouth syndrome, paresthesias, Fabry's disease, facial pain, trigeminal neuralgia, neuropathic pain due to diabetes, neuropathic pain due to AIDS, orofacial pain, dental pain, pain due to tooth extraction, pain due to wisdom tooth extraction, tooth sensitivity to cold, tooth sensitivity to heat, oral mucositis, temporomandibular joint pain, joint pain caused by gout, pain associated with tattooing or tattoo removal processes, pain due to bunions, testicular pain, myofascial pain, urinary bladder pain, urinary tract pain, cystitis, pain due to kidney stones, renal colic, vulvar pain, vaginal pain, post-birth pain, menstrual pain, scrotal pain, perineal pain, pelvic pain or hypersensitivity, cutaneous pain or irritation after surgery, after intense pulsed light treatment (IPL), after treatment with monochromatic pulsed light (laser), after a treatment with chemical flaking agents or after overexposure to external aggressive agents and pain due to chronic alcoholism, among others.

In another particular embodiment, inflammation is selected, for example and not restricted to, from the group formed by neurogenic inflammation, join inflammation, tendon inflammation, muscular inflammation, sepsis, vascular inflammation, respiratory inflammation, chronic obstructive pulmonary disease, rhinitis, allergic rhinitis, asthma, otitis, intestinal inflammation, Crohn's disease, pancreatitis, hepatitis, conditions related to chronic inflammation, to acute inflammation, nephritis, system lupus erythematosus, arthritis, rheumatoid arthritis, adult and juvenile rheumatoid arthritis, Still's disease, psoriatic arthritis, osteoarthritis, arthritis caused by gout, rheumatoid spondylitis, glomerulonephritis, neuritis, inflammation of the nerve tissue, multiple sclerosis, immunological system disorders, Sjögren's syndrome, atherosclerosis, myocarditis, pericarditis, vasculitis, inflammatory skin conditions, psoriasis, sensitive skin, dermatitis, atopic dermatitis, contact dermatitis, diaper dermatitis, seborrheic dermatitis, eczema, rosacea, acne, hyperproliferative skin disease, burns, sunburn, cutaneous inflammation after surgery, after intense pulsed light treatment (IPL), after treatment with monochromatic pulsed light (laser), after a treatment with chemical flaking agents or after overexposure to external aggressive agents, inflammation of the vaginal mucous membranes, vulvodynia, vaginitis, inflammation of the oral mucous membranes, gingivitis, periodontitis, inflammatory eye diseases, uveitis, ocular and vernal conjunctivitis, sarcoidosis, peptic ulcers, urticaria, bullous pemphigoid, scleroderma, fibrosis, angioedema, anaphylaxis, alopecia, hepatic cirrhosis, restenosis, polymyalgia, rheumatica, seronegative spondyloarthropathies, including ankylosing spondylitis and Reiter's disease, dermatomyositis, inclusion body myositis, polymyositis and lymphangioleiomyomatosis, among others.

In another particular embodiment, the neurological, compulsive and neuropsychiatric diseases and/or disorders which are improved by inhibition of neuronal exocytosis are selected, for example and not restricted to, from the group formed by muscular spasticity, dystonia, and more specifically focal dystonia such as blepharospasm, torsion dystonia, cervical dystonia or torticollis, laryngeal dystonia or spasmodic dysphonia, oromandibular dystonia, extremity dystonia such as writer's cramp, musician's cramp or foot dystonia, bruxism, facial scoliosis, hemifacial spasm, tics and/or strabismus; segmentary dystonia, Meige's syndrome, multifocal dystonia, hemidystonia, dopamine-responsive dystonia, Segawa's dystonia, trembling, Parkinson's disease, nerve impingements, Alzheimer's disease and Tourette's syndrome, among others.

In another particular embodiment, the cosmetic, non-therapeutic treatment and/or care of the skin, is a treatment and/or prevention, delay, or hindering of aging and/or photoaging, treatment and/or prevention, delay, or hindering of wrinkles and/or expression wrinkles, treatment and/or prevention, delay, or hindering of perspiration, treatment and/or care of skin disorders selected, for example and not restricted to, from the group formed by calluses and warts, among others. In an even more particular embodiment in its treatment and/or care of the facial skin.

In another particular embodiment, the treatment and/or care of the hair is a hair-growth stimulating and/or hair loss prevention treatment.

In another particular embodiment, the treatment and/or prevention, delay, or hindering of perspiration, and the treatment and/or prevention, delay, or hindering of hyperhidrosis, are treatments and/or prevention, delay, or hindering of perspiration or axillary, facial, genital, palmar or plantar hyperhidrosis.

In another particular embodiment, the compounds of the invention can be administered by any means that causes contact between the compounds and the site of action in a mammal's body, preferably that of a human being, and in the form of a composition which contains them. The administration of the compounds of this invention is carried out topically, transdermally, orally or parenterally. In a more particular aspect topical or transdermal application is carried out by iontophoresis, sonophoresis, electroporation, mechanical pressure, osmotic pressure gradient, occlusive cure, microinjections, by needle-free injections by means of pressure, by microelectric patches, face masks or any combination thereof.

The frequency of the application can vary greatly, depending on the needs of each subject, with a recommendation of an application from once a month to ten times a day, preferably from once a week to four times a day, more preferably from three times a week to twice a day, even more preferably once a day.

EXAMPLES OF ADMINISTRATION

The following specific examples provided herein illustrate the nature of this invention. These examples are included for illustrative purposes only and should not be construed as limitations on the invention claimed herein.

General Methodology

Abbreviations

The abbreviations used for amino acids follow the 1983 IUPAC-IUB Joint Commission on biochemical Nomenclature recommendations outlined in *Eur. J. Biochem*., (1984), 138, 9-37.

®, resin; 2,6-diClz, 2,6-dichlorobenzyl; 2-BrZ, 2-bromobenzyloxycarbonyl 2-ClTrt-®, 2-chlorotrityl resin; Ac, acetyl; Adpoc, 1-(1-adamantyl)-1-methylethoxy-carbonyl: Ala, alanine; All, allyl; Alloc, allyloxycarbonyl; AM, 2-[4-aminomethyl-(2,4-dimethoxyphenyl)]phenoxyacetic acid; Arg, arginine; Asn, asparagine; Asp, aspartic acid; Boc, tert-butyloxycarbonyl, Bom, benzyloxymethyl; Brz, benzyl; Cbz, benzyloxycarbonyl; cHx, cyclohexyl; ClZ, 2-chlorobenzyl; Cys, cysteine; C-terminal, carboxy-terminal; DCM, dichloromethane, methylene chloride; Dde, N-[1-(4, 4-dimethyl-2,6-dioxocyclohex-1-ylidene)ethyl; DIEA, N,N'-diisopropylethylamine; DIPCDI, N,N'-diisopropylcarbodiimide; Dmab, 4-(N-[1-(4,4-dimethyl-2,6-dioxocyclohexylidene)-3-methylbutyl]amino)benzyl; DMF, N,N-dimethylformamide; Dnp, 2,4-dinitrophenyl; EDTA, ethylenediaminetetraacetic acid; equiv. equivalent; ESI-MS, electrospray ionization mass spectrometry; Fm, fluorenylmethyl Fmoc, 9-fluorenylmethyloxycarbonyl; For, formyl; Gln, glutamine; Glu, glutamic acid, Gly, glycine; GST, glutathione S-transferase; His, histidine; HOAt, 1-hydroxyazabenzotriazole; HOBt, 1-hydroxybenzotriazole, HPLC, high performance liquid chromatography; Ile, isoleucine; INCI, International Nomenclature of Cosmetic Ingredients; IPL, Intense Pulsed Light; ivDde, 1-(4,4-dimethyl-2,6-dioxocyclohexylidene)-3-methyl-butyl; LDMA-25, lauryldimonium hydrolyzed protein; Leu, leucine; Lys, lysine; MBHA, p-methylbenzhydrylamine; Me, methyl, MeCN, acetonitrile; MeOH, methanol; Met, methionine, MetO, methionine(sulfoxide); $MetO_2$, methionine(sulfone); MLV, multilamellar vesicles; Mtr, 4-methoxy-2,3,6-trimethylbenzenesulfonyl; Mts, mesitylenesulfonyl, Mtt, methoxytrityl or methyltrityl; Myr, myristoyl; MW, molecular weight; N-terminal, amino terminal; PAL, t-(4-aminomethyl-3,5-dimethoxyphenoxy)valeric acid; Palm, palmitoyl; Pbf, 2,2,4,6,7-pentamethyldihydrobenzofuran-5-sulfonyl; PEG, polyethylene glycol, Phe, phenylalanine; Pmc, 2,2,5, 7,8-pentamethylchroman-6-sulfonyl; pNZ, p-nitrobenzyloxycarbonyl; Pro, proline; q.s., quantity sufficient; q.s.p., quantity sufficient for; SEM, standard error of the mean; Ser, serine; SNAP-25, synaptosomal-associated protein 25; SNARE, Soluble NSF Attachment Protein Receptor; tBu, tert-butyl; Teoc, 2-(trimethylsilyl)ethyloxycarbonyl; TFA, trifluoroacetic acid; THF, tetrahydrofuran, Thr, threonine; TIS, triisopropylsilane; Tos, tosyl or p-toluenesulfonyl; TPA, 12-O-tetradecanoylphorbol-13-acetate; Troc, 2,2,2-trichloroethoxycarbonyl; Trp, tryptophan; Trt, triphenylmethyl or trityl; Tyr, tyrosine; IUPAC, International Union of Pure and Applied Chemistry; IUB, International Union of Biochemistry; ULV, unilamellar vesicles; UVA, ultraviolet radiation A; UVB, ultraviolet radiation B; Val, valine; VAMP, vesicle-associated membrane proteins; Xan, xanthyl; Z, benzyloxycarbonyl.

Chemical Synthesis

All synthetic processes were carried out in polypropylene syringes fitted with porous polyethylene discs. All the reagents and solvents were synthesis quality and were used without any additional treatment. The solvents and soluble reagents were removed by suction. The Fmoc group was removed with piperidine-DMF (2 G, v/v) (1×1 min, 1×5 min; 5 mL/g resin) [Lloyd-Williams P. et. al., "*Chemical Approaches to the Synthesis of Peptides and Proteins*", (1997), CRC, Boca Raton (FL, USA)]. Washes between stages of deprotection, coupling, and, again, deprotection, were carried out with DMF (3×1 min) each time using 10 mL solvent/g resin. The coupling reactions were performed with 3 mL solvent/g resin. The control of the couplings was performed by carrying out the ninhydrin test [Kaiser E. et al., "*Color test for detection of free terminal amino groups in the solid-phase synthesis of peptides*", (1970), Anal. Biochem., 34(2), 595-598] or chloranil test [Christensen T., "*A Qualitative Test for Monitoring Coupling Completeness in Solid Phase Peptide Synthesis Using Chloranil*", (1979),

*Acta Chem. Scand.*, 33B, 763-766]. All synthetic reactions and washes were carried out at 25° C.

The HPLC chromatographic analysis was carried out with a Shimadzu equipment (Kyoto, Japan) using a reversed-phase column thermostatized at 30° C. (250×4.0 mm, Kromasil $C_8$, 5 μm, Akzo Nobel, Sweden). The elution was carried out suing a gradient of acetonitrile (+0.07% TFA) in water (+0.1% TFA) at a flow rate of 1 mL/min and detection was carried out at 220 nm. The electrospray ionization mass spectrometry was carried out in a WATERS Alliance ZQ 2000 detector using a mixture of $MeCN:H_2O$ 4:1 (+0.1% TFA) as the mobile phase and a flow rate of 0.2 mL/min.

Example 1

Obtaining Fmoc-$W_n$-$X_m$-$AA_1$-$AA_2$-$AA_3$-$AA_4$-$AA_5$-$AA_6$-$AA_7$-$AA_8$-$AA_9$-$Y_p$-$Z_q$-AM-MBHA-®, wherein $AA_1$ is -L-Gln-, -L-Asn-, -L-Glu- or -L-Asp-; $AA_2$ is -L-Gln-, -L-Asn-, or -L-Glu-; $AA_3$ is -L-Leu-; $AA_4$ is -L-Glu-; $AA_5$ is -L-Arg-, -L-His-, -L-Lys- or -L-Asn-; $AA_6$ is -L-Ile-; $AA_7$ is -L-Met- or -L-MetO-; $AA_8$ is -L-Asp-; $AA_9$ is -L-Gln- or -L-Asn-; and n, m, p and q are 0

5 mmol (1 equiv) of the Fmoc-AM-MBHA resin with a functionalization of 0.73 mmol/g were treated with piperidine-DMF according to the described general protocol in order to remove the Fmoc group. 2.5 equiv of Fmoc-L-Gln(Trt)-OH or Fmoc-L-Asn(Trt)-OH were incorporated onto the deprotected resin in the presence of 2.5 equiv of DIPCDI and 2.5 equiv of HOBt, using DMF as a solvent, for 1 hour.

The resins were then washed as described in the general methods and the deprotection treatment of the Fmoc group was repeated to couple the next amino acid. The Fmoc N-terminal group was deprotected as described in the general methods and 2.5 equiv of Fmoc-L-Asp(OtBu)-OH; 2.5 equiv of Fmoc-L-Met-OH or Fmoc-L-MetO-OH; 2.5 equiv of Fmoc-L-Ile-OH; 2.5 equiv of Fmoc-L-Arg(Pbf)-OH, Fmoc-L-His(Trt)-OH, Fmoc-L-Lys(Boc)-OH or Fmoc-L-Asn(Trt)-OH; 2.5 equiv of Fmoc-L-Glu(OtBu)-OH; 2.5 equiv of Fmoc-L-Leu-OH; 2.5 equiv of Fmoc-L-Gln(Trt)-OH, Fmoc-L-Asn(Trt)-OH or Fmoc-L-Glu(OtBu)-OH and finally 2.5 equiv of Fmoc-L-Gln(Trt)-OH, Fmoc-L-Asn(Trt)-OH, Fmoc-L-Glu(OtBu)-OH or Fmoc-L-Asp(OtBu)-OH were sequentially coupled onto the peptidyl resins for 1 hour, each coupling in the presence of 2.5 equiv of HOBt and 2.5 equiv of DIPCDI and using DMF as a solvent.

After the synthesis, the peptidyl resins were washed with DCM (5×3 min) and dried under nitrogen stream.

Example 2

Prophetic Synthesis of Fmoc-$W_n$-$X_m$-$AA_1$-$AA_2$-$AA_3$-$AA_4$-$AA_5$-$AA_6$-$AA_7$-$AA_8$-$AA_9$-$Y_p$-$Z_q$-O-2-ClTrt-®, wherein $AA_1$ is -L-Arg-, -L-His-, -L-Lys-, -L-Gln-, -L-Asn-, -L-Glu- or -L-Asp-; $AA_2$ is -L-Arg-, -L-His-, -L-Lys-, -L-Gln-, -L-Asn-, -L-Glu- or -L-Asp-; $AA_3$ is -L-Leu-, -L-Ile-, -L-Val-, -L-Met-, -L-MetO-, -L-MetO$_2$-, -L-Glu-, -L-Asp-, -L-Phe-, -L-Trp- or -L-Tyr-; $AA_4$ is -L-Lys-, -L-His-, -L-Glu- or -L-Asp-; $AA_5$ is -L-Arg-, -L-His-, -L-Lys-, -L-Gln-, -L-Asn-, -L-Glu- or -L-Asp-; $AA_6$ is -L-Met, -L-MetO, -L-MetO$_2$, -L-Ile-, -L-Leu-, -L-Val-, -L-His-, -L-Lys- or -L-Arg-; $AA_7$ is -L-Met or -L-MetO- or -L-MetO$_2$; $AA_8$ is -L-Glu-, -L-Asp-, -Gly-, -L-Ala- or -L-Pro-; $AA_9$ is -L-Gln or -L-Asn; and n, m, p and q are 0.

8.8 mmol (1 equiv) of Fmoc-L-Gln(Trt)-OH or Fmoc-L-Asn(Trt)-OH dissolved in 55 mL of DCM to which 0.86 equiv of DIEA are added, are coupled to the dry 2-chlorotrityl resin (5.5 g; 8.8 mmol). They are stirred for 5 min, after which 1.66 equiv of DIEA are added. The mixture is allowed to react for 40 min. The remaining chloride groups are blocked by treatment with 4.4 mL of MeOH.

The N-terminal Fmoc group is deprotected as described in the general methods and 2.5 equiv of Fmoc-L-Glu(OtBu)-OH, Fmoc-L-Asp(OtBu)-OH, Fmoc-Gly-OH, Fmoc-L-Ala-OH or Fmoc-L-Pro-OH are coupled onto the peptidyl resins in presence of 2.5 equiv of DIPCDI and 2.5 equiv of HOBt, using DMF as a solvent, for 1 hour. The resins are then washed as described in the general methods and the deprotection treatment of the Fmoc group is repeated to couple the next amino acid. Following the protocols described, 2.5 equiv of Fmoc-L-Met-OH, Fmoc-L-MetO-OH or Fmoc-L-MetO$_2$-OH; 2.5 equiv of Fmoc-L-Met-OH, Fmoc-L-MetO-OH, Fmoc-L-MetO$_2$-OH, Fmoc-L-Ile-OH, Fmoc-L-Leu-OH, Fmoc-L-Val-OH, Fmoc-L-His(Trt)-OH, Fmoc-L-Lys(Boc)-OH or Fmoc-L-Arg(Pbf)-OH; 2.5 equiv of Fmoc-L-Arg(Pbf)-OH, Fmoc-L-His(Trt)-OH, Fmoc-L-Lys(Boc)-OH, Fmoc-L-Gln(Trt)-OH, Fmoc-L-Asn(Trt)-OH, Fmoc-L-Glu(OtBu)-OH or Fmoc-L-Asp(OtBu)-OH; 2.5 equiv of Fmoc-L-Lys(Boc)-OH, Fmoc-L-His(Trt)-OH, Fmoc-L-Glu(OtBu)-OH or Fmoc-L-Asp(OtBu)-OH; 2.5 equiv of Fmoc-L-Leu-OH, Fmoc-L-Ile-OH, Fmoc-L-Val-OH, Fmoc-L-Met-OH, Fmoc-L-MetO-OH, Fmoc-L-MetO$_2$-OH, Fmoc-L-Glu(OtBu)-OH, Fmoc-L-Asp(OtBu)-OH, Fmoc-L-Phe-OH, Fmoc-L-Trp(Boc)-OH or Fmoc-L-Tyr(tBu)-OH; 2.5 equiv of Fmoc-L-Arg(Pbf)-OH, Fmoc-L-His(Trt)-OH, Fmoc-L-Lys(Boc)-OH, Fmoc-L-Gln(Trt)-OH, Fmoc-L-Asn(Trt)-OH, Fmoc-L-Glu(OtBu)-OH or Fmoc-L-Asp(OtBu)-OH and finally 2.5 equiv of Fmoc-L-Arg(Pbf)-OH, Fmoc-L-His(Trt)-OH, Fmoc-L-Lys(Boc)-OH, Fmoc-L-Gln(Trt)-OH, Fmoc-L-Asn(Trt)-OH, Fmoc-L-Glu(OtBu)-OH or Fmoc-L-Asp(OtBu)-OH are sequentially coupled in the presence of 2.5 equiv of HOBt and 2.5 equiv of DIPCDI in each coupling.

After the synthesis, the peptidyl resins are washed with DCM (5×3 min) and dried under nitrogen stream.

Example 3

Obtaining Fmoc-$W_n$-$X_m$-$AA_1$-$AA_2$-$AA_3$-$AA_4$-$AA_5$-$AA_6$-$AA_7$-$AA_8$-$AA_9$-$Y_p$-$Z_q$-AM-MBHA-®, $AA_1$ is -L-Arg-, -L-His-, -L-Lys-, -L-Gln-, -L-Asn-, -L-Glu- or -L-Asp-; $AA_2$ is -L-Arg-, -L-His-, L-Lys-, -L-Gln-, -L-Asn-, or -L-Asp-; $AA_3$ is -L-Leu-, -L-Met-, -L-Glu-, -L-Asp- or -L-Phe-; $AA_4$ is -L-His- or -L-Glu-; $AA_5$ is -L-Arg-, -L-His-, -L-Lys-, -L-Gln-, -L-Asn- or -L-Asp; $AA_6$ is -L-Ile-, -L-Lys-, or -L-Arg-; $AA_7$ is -L-Met- or -L-MetO-; $AA_8$ is -L-Asp-, -L-Gly- or -L-Ala; $AA_9$ is a bond; and n, m, p and q are 0.

5 mmol (1 equiv) of the Fmoc-AM-MBHA resin with a functionalization of 0.73 mmol/g were treated with piperidine-DMF according to the described general protocol in order to remove the Fmoc group. 2.5 equiv of Fmoc-L-Asp(OtBu)-OH, Fmoc-Gly-OH, or Fmoc-L-Ala-OH were incorporated onto the deprotected resin in the presence of 2.5 equiv of DIPCDI and 2.5 equiv of HOBt, using DMF as a solvent, for 1 hour.

The resins were then washed as described in the general methods and the deprotection treatment of the Fmoc group was repeated to couple the next amino acid. The Fmoc N-terminal group was deprotected as described in the general methods, and 2.5 equiv of Fmoc-L-Met-OH or Fmoc-L-MetO-OH; 2.5 equiv of Fmoc-L-Ile-OH, Fmoc-L-Lys(Boc)-OH or Fmoc-L-Arg(Pbf)-OH; 2.5 equiv of Fmoc-L-Arg(Pbf)-OH, Fmoc-L-His(Trt)-OH, Fmoc-L-Lys(Boc)-OH, Fmoc-L-Gln(Trt)-OH, Fmoc-L-Asn(Trt)-OH, or Fmoc-L-Asp(OtBu)-OH; 2.5 equiv of Fmoc-L-His(Trt)-OH or Fmoc-L-Glu(OtBu)-OH; 2.5 equiv of Fmoc-L-Leu-OH, Fmoc-L-Met-OH, Fmoc-L-Glu(OtBu)-OH, Fmoc-L-Asp (OtBu)-OH, Fmoc-L-Phe-OH; 2.5 equiv of Fmoc-L-Gln(Trt)-OH, Fmoc-L-Asn(Trt)-OH or Fmoc-L-Asp(OtBu)-OH and finally 2.5 equiv of Fmoc-L-Arg(Pbf)-OH, Fmoc-L-His(Trt)-OH, Fmoc-L-Lys(Boc)-OH, Fmoc-L-Gln(Trt)-OH, Fmoc-L-Asn(Trt)-OH, Fmoc-L-Glu(OtBu)-OH or Fmoc-L-Asp(OtBu)-OH were sequentially coupled onto the peptidyl resins for 1 hour, each coupling in the presence of 2.5 equiv of HOBt and 2.5 equiv of DIPCDI, and using DMF as a solvent.

After the synthesis, the peptidyl resins were washed with DCM (5×3 min) and dried under nitrogen stream.

Example 4

Prophetic Synthesis of Obtaining Fmoc-$W_n$-$X_m$-$AA_1$-$AA_2$-$AA_3$-$AA_4$-$AA_5$-$AA_6$-$AA_7$-$AA_8$-$AA_9$-$Y_p$-$Z_q$-O-2-ClTrt-®, wherein $AA_1$ is -L-Arg-, -L-His-, -L-Lys-, -L-Gln-, -L-Asn-, -L-Glu- or -L-Asp-; $AA_2$ is -L-Arg-, -L-His-, -L-Lys-, -L-Gln-, -L-Asn-, -L-Glu- or -L-Asp-; $AA_3$ is -L-Leu-, -L-Ile-, -L-Val-, -L-Met-, -L-MetO-, -L-MetO$_2$-, -L-Glu-, -L-Asp-, -L-Phe-, -L-Trp- or -L-Tyr-; $AA_4$ is -L-Lys-, -L-His-, -L-Glu- or -L-Asp-; $AA_5$ is -L-Arg-, -L-His-, -L-Lys--L-Gln-, -L-Asn-, -L-Glu- or -L-Asp; $AA_6$ is -L-Met-, -L-MetO-, -L-MetO$_2$-, -L-Ile-, -L-Leu-, -L-Val-, -L-His-, -L-Lys- or -L-Arg-; $AA_7$ is -L-Met- or -L-MetO- or -L-MetO$_2$; $AA_8$ is -L-Glu-, -L-Asp-, -Gly-, -L-Ala- or -L-Pro-; $AA_9$ is a bond; and n, m, p and q are 0.

8.8 mmol (1 equiv) of Fmoc-L-Glu(OtBu)-OH, Fmoc-L-Asp(OtBu)-OH, Fmoc-L-Gly-OH, Fmoc-L-Ala-OH, or Fmoc-L-Pro-OH dissolved in 55 mL of DCM together with 0.86 equiv of DIEA are added to the dry 2-chlorotrityl resin (5.5 g; 8.8 mmol). They are stirred for 5 min, after which 1.66 equiv of DIEA are added. The mixture is allowed to react for 40 min. The remaining chloride groups are blocked by treatment with 4.4 mL of MeOH.

The N-terminal Fmoc group is deprotected as described in the general methods and 2.5 equiv of Fmoc-L-MetOH, Fmoc-L-MetO-OH or Fmoc-L-MetO$_2$-OH are coupled onto the peptidyl resins in the presence of 2.5 equiv of DIPCDI and 2.5 equiv of HOBt using DMF as a solvent for 1 hour. The resins are then washed as described in the general methods and the deprotection treatment of the Fmoc group is repeated to couple the next amino acid. Following the protocols described, 2.5 equiv of Fmoc-L-Met-OH, Fmoc-L-MetO-OH, Fmoc-L-MetO$_2$-OH, Fmoc-L-Ile-OH, Fmoc-L-Leu-OH, Fmoc-L-Val-OH, Fmoc-L-His(Trt)-OH, Fmoc-L-Lys(Boc)-OH or Fmoc-L-Arg(Pbf)-OH; 2.5 equiv of Fmoc-L-Arg(Pbf)-OH, Fmoc-L-His(Trt)-OH, Fmoc-L-Lys(Boc)-OH, Fmoc-L-Gln(Trt)-OH, Fmoc-L-Asn(Trt)-OH, Fmoc-L-Glu(OtBu)-OH or Fmoc-L-Asp(OtBu)-OH; 2.5 equiv of Fmoc-L-Lys(Boc)-OH, Fmoc-L-His(Trt)-OH, Fmoc-L-Glu(OtBu)-OH or Fmoc-L-Asp(OtBu)-OH; 2.5 equiv of Fmoc-L-Leu-OH, Fmoc-L-Ile-OH, Fmoc-L-Val-OH, Fmoc-L-Met-OH, Fmoc-L-MetO-OH, Fmoc-L-MetO$_2$-OH, Fmoc-L-Glu(OtBu)-OH, Fmoc-L-Asp(OtBu)-OH, Fmoc-L-Phe-OH, Fmoc-L-Trp(Boc)-OH or Fmoc-L-Tyr(tBu)-OH; 2.5 equiv of Fmoc-L-Arg(Pbf)-OH, Fmoc-L-His(Trt)-OH, Fmoc-L-Lys(Boc)-OH, Fmoc-L-Gln(Trt)-OH, Fmoc-L-Asn(Trt)-OH, Fmoc-L-Glu(OtBu)-OH or Fmoc-L-Asp(OtBu)-OH and finally 2.5 equiv of Fmoc-L-Arg(Pbf)-OH, Fmoc-L-His(Trt)-OH, Fmoc-L-Lys(Boc)-OH, Fmoc-L-Gln(Trt)-OH, Fmoc-L-Asn(Trt)-OH, Fmoc-L-Glu(OtBu)-OH or Fmoc-L-Asp(OtBu)-OH are sequentially coupled, each coupling in the presence of 2.5 equiv of HOBt and 2.5 equiv of DIPCDI.

After the synthesis, the peptidyl resins are washed with DCM (5×3 min) and dried under nitrogen stream.

Example 5

General Process for Cleavage of Fmoc N-Terminal Protective Group.

The N-terminal Fmoc group of the peptidyl resins obtained in examples 1 and 3 was deprotected as described in the general methods (20% piperidine in DMF, 1×5 min+1×20 min). The peptidyl resins were washed with DMF (5×1 min), DCM (4×1 min), diethyl ether (4×1 min) and dried under vacuum.

Prophetically, using the same protocol the N-terminal Fmoc group of the peptidyl resins obtained in examples 2 and 4 are deprotected, washed and dried.

Example 6

Process for Introducing the $R_1$ Palmitoyl Group onto the Peptidyl Resins Obtained in Example 5 for SEQ ID NO:51.

10 equiv of palmitic acid pre-dissolved in DMF (1 mL) were added onto 1 mmol (1 equiv) of the peptidyl resins obtained in Example 5 for SEQ ID NO:51, in the presence of 10 equiv of HOBt and 10 equiv of DIPCDI. They were allowed to react for 15 hours, after which the resins were washed with THF (5×1 min), DCM (4×1 min), DMF (5×1 min), MeOH (5×1 min), DMF (54×1 min), THF (5×1 min), DMF (5×1 min), DCM (4×1 min), ether (3×1 min), and dried under vacuum.

Prophetically, following the same protocol the $R_1$ palmitoyl group is introduced onto the other peptidyl resins obtained in Examples 1 and 4 after deprotecting the N-terminal following the protocol described in Example 5.

Example 7

Process for Introducing the $R_1$ Acetyl Group onto the Peptidyl Resins Obtained in Example 5.

1 mmol (1 equiv) of the peptidyl resins obtained in Example 5 was treated with 25 equiv of acetic anhydride in the presence of 25 equiv of DIEA, using 5 mL of DMF as a solvent. They were allowed to react for 30 min, after which the peptide resins were washed with DMF (5×1 min), DCM (4×1 min), diethyl ether (4×1 min) and were dried under vacuum.

Prophetically, following the same protocol the $R_1$ acetyl group is introduced onto the peptidyl resins prophetically obtained in Examples 5.

Example 8

Cleavage Process of the Peptidyl Resins Obtained in Examples 6 and 7 from the Polymeric Support.

200 mg of the dried peptidyl resins obtained in Examples 6 and 7 were treated with 5 mL of TFA:TIS:H$_2$O (90:5:5) for 2 hours at room temperature under stirring. The filtrates were collected onto 50 mL cold diethyl ether, filtered through polypropylene syringes fitted with porous polyethylene discs, and washed 5 times with 50 mL diethyl ether. The final precipitates were dried under vacuum.

HPLC analysis of the obtained peptides in gradients of MeCN (+0.07% TFA) in H$_2$O (+0.1% TFA) showed a purity exceeding 80% in all cases. The identity of the peptides obtained was confirmed by ESI-MS.

Example 9

Prophetic Cleavage Process from the Polymeric Support and Functionalization with $R_2$ Substituted Amine: Obtaining Ac-$W_n$-$X_m$-$AA_1$-$AA_2$-$AA_3$-$AA_4$-$AA_5$-$AA_6$-$AA_7$-$AA_8$-$AA_9$-$Y_p$-$Z_q$-NH—$(CH_2)_{15}$—$CH_3$, wherein $AA_1$ is -L-Arg-, -L-His-, -L-Lys- or -L-Gln-, -L-Asn-, -L-Glu- or -L-Asp; $AA_2$ is -L-Arg-, -L-His-, -L-Lys-, -L-Gln-, -L-Asn-, -L-Glu or -L-Asp-; $AA_3$ is -L-Leu-, -L-Ile-, -L-Val-, -L-Met-, -L-MetO-, -L-MetO$_2$-, -L-Glu-, -L-Asp-, -L-Phe-, -L-Trp- or -L-Tyr-; $AA_4$ is -L-Lys-, -L-His-, -L-Glu- or -L-Asp-; $AA_5$ is -L-Arg-, -L-His-, -L-Lys-, -L-Gln-, -L-Asn-, -L-Glu- or -L-Asp-; $AA_6$ is -L-Met-, -L-MetO-, -L-Met-O$_2$-, -L-Ile-, -L-Leu-, -L-Val-, -L-His-, -L-Lys- or -L-Arg-; $AA_7$ is -L-Met-, -L-MetO- or -L-MetO$_2$-; $AA_8$ is -L-Glu-, -L-Asp-, -Gly-, -L-Ala- or -L-Pro-; $AA_9$ is -L-Gln-, -L-Asn- or a bond; and n, m, p and q are 0.

The compounds Ac-$W_n$-$X_m$-$AA_1$-$AA_2$-$AA_3$-$AA_4$-$AA_5$-$AA_6$-$AA_7$-$AA_8$-$AA_9$-$Y_p$-$Z_q$-OH with fully protected side chains are obtained by treating 150 mg of the prophetic peptidyl resins Ac-$W_n$-$X_m$-$AA_1$-$AA_2$-$AA_3$-$AA_4$-$AA_5$-$AA_6$-$AA_7$-$AA_8$-$AA_9$-$Y_p$-$Z_q$-O-2ClTrt-® from Example 7, previously desiccated under vacuum in the presence of KOH, with 3 mL of a 3% solution of TFA in DCM for 5 min. The filtrates are collected onto 50 mL of cold diethyl ether and the treatment is repeated three times. The ether solutions are evaporated to dryness at reduced pressure and room temperature, the precipitates are redissolved in 50% of MeCN in H$_2$O and they are lyophilized. 10 mg of the obtained crude peptides are weighed in a flask and 3 equiv of hexadecylamine and 25 mL of anhydrous DMF are added. 2 equiv of DIPCDI are added and allowed to react under magnetic stirring at 47° C. The reactions are monitored by HPLC until disappearance of the initial products. The solvents are evaporated to dryness and co-evaporated twice with DCM. The obtained residues [Ac-$W_n$-$X_m$-$AA_1$-$AA_2$-$AA_3$-$AA_4$-$AA_5$-$AA_6$-$AA_7$-$AA_8$-$AA_9$-$Y_p$-$Z_q$-NH—$(CH_2)_{15}$—$CH_3$ with fully protected side chains] are redissolved in 25 mL of a mixture of TFA-DCM-anisole (49:49:2) and allowed to react for 30 min at room temperature. 250 mL of cold diethyl ether are added, the solvents are evaporated under reduced pressure and two additional co-evaporations with ether are carried out. The residues are dissolved in a mixture of 50% MeCN in H$_2$O and lyophilized.

Purity of the obtained peptides is determined by HPLC analysis in gradients of MeCN (+0.07% TFA) in H$_2$O (+0.1% TFA). The identity of the peptides obtained is confirmed by ESI-MS.

Example 10

Following the protocols described in examples 1 to 9, routinely varying the nature of the reagents and the peptide sequences, the following compounds included in the scope of this invention were also obtained.

TABLE 3

| Identifier | Average MW | Experimental MW |
| --- | --- | --- |
| Ac-SEQ ID NO: 1-NH$_2$ | 1140.29 | 1140.43 ± 0.25 |
| Ac-SEQ ID NO: 2-NH$_2$ | 1093.23 | 1093.86 ± 0.77 |

TABLE 3-continued

| Identifier | Average MW | Experimental MW |
| --- | --- | --- |
| Ac-SEQ ID NO: 3-NH$_2$ | 1098.25 | 1099.08 ± 1.06 |
| Ac-SEQ ID NO: 4-NH$_2$ | 1112.28 | 1112.26 ± 0.36 |
| Ac-SEQ ID NO: 5-NH$_2$ | 1121.25 | 1121.25 ± 0.17 |
| Ac-SEQ ID NO: 6-NH$_2$ | 1113.22 | 1113.37 ± 0.20 |
| Ac-SEQ ID NO: 7-NH$_2$ | 1099.24 | 1099.73 ± 0.27 |
| Ac-SEQ ID NO: 8-NH$_2$ | 1126.27 | 1126.31 ± 0.17 |
| Ac-SEQ ID NO: 11-NH$_2$ | 1071.14 | 1070.67 ± 0.88 |
| Ac-SEQ ID NO: 12-NH$_2$ | 1057.15 | 1057.16 ± 0.04 |
| Ac-SEQ ID NO: 13-NH$_2$ | 1058.09 | 1057.50 ± 0.86 |
| Ac-SEQ ID NO: 14-NH$_2$ | 1099.19 | 1099.77 ± 0.67 |
| Ac-SEQ ID NO: 15-NH$_2$ | 1098.21 | 1099.42 ± 1.44 |
| Ac-SEQ ID NO: 18-NH$_2$ | 1099.19 | 1101.01 ± 2.46 |
| Ac-SEQ ID NO: 19-NH$_2$ | 1122.23 | 1123.35 ± 1.58 |
| Ac-SEQ ID NO: 20-NH$_2$ | 1079.16 | 1078.73 ± 1.18 |
| Ac-SEQ ID NO: 21-NH$_2$ | 1084.27 | 1083.73 ± 1.84 |
| Ac-SEQ ID NO: 22-NH$_2$ | 1121.25 | 1121.49 ± 0.52 |
| Ac-SEQ ID NO: 23-NH$_2$ | 1108.20 | 1108.17 ± 0.54 |
| Ac-SEQ ID NO: 24-NH$_2$ | 1141.28 | 1142.17 ± 1.48 |
| Ac-SEQ ID NO: 25-NH$_2$ | 1121.29 | 1121.91 ± 0.67 |
| Ac-SEQ ID NO: 26-NH$_2$ | 1145.31 | 1145.00 ± 1.70 |
| Ac-SEQ ID NO: 27-NH$_2$ | 1111.25 | 1112.40 ± 1.29 |
| Ac-SEQ ID NO: 28-NH$_2$ | 1117.25 | 1116.62 ± 1.85 |
| Ac-SEQ ID NO: 29-NH$_2$ | 1014.24 | 1014.20 ± 0.13 |
| Ac-SEQ ID NO: 30-NH$_2$ | 987.13 | 987.11 ± 0.09 |
| Ac-SEQ ID NO: 31-NH$_2$ | 1000.17 | 1000.13 ± 0.14 |
| Ac-SEQ ID NO: 32-NH$_2$ | 1120.26 | 1120.41 ± 0.29 |
| Ac-SEQ ID NO: 33-NH$_2$ | 1124.34 | 1124.63 ± 0.31 |
| Ac-SEQ ID NO: 34-NH$_2$ | 1017.13 | 1017.46 ± 0.39 |
| Ac-SEQ ID NO: 35-NH$_2$ | 1026.14 | 1026.18 ± 0.17 |
| Ac-SEQ ID NO: 36-NH$_2$ | 1089.24 | 1089.06 ± 0.75 |
| Ac-SEQ ID NO: 40-NH$_2$ | 1137.25 | 1137.79 ± 0.58 |
| Ac-SEQ ID NO: 41-NH$_2$ | 1087.14 | 1087.24 ± 0.19 |
| Ac-SEQ ID NO: 43-NH$_2$ | 1127.25 | 1127.96 ± 1.70 |
| Ac-SEQ ID NO: 47-NH$_2$ | 1146.29 | 1146.39 ± 0.10 |
| Ac-SEQ ID NO: 48-NH$_2$ | 1117.21 | 1115.38 ± 2.51 |
| Ac-SEQ ID NO: 50-NH$_2$ | 1160.31 | 1160.16 ± 0.75 |
| Ac-SEQ ID NO: 51-NH$_2$ | 1145.26 | 1145.27 ± 2.60 |
| Palm-SEQ ID NO: 51-NH$_2$ | 1341.64 | 1341.32 ± 0.79 |
| Ac-SEQ ID NO: 52-NH$_2$ | 1187.34 | 1186.80 ± 1.38 |
| Ac-SEQ ID NO: 53-NH$_2$ | 1159.33 | 1159.53 ± 0.76 |
| Ac-SEQ ID NO: 56-NH$_2$ | 1173.36 | 1173.32 ± 2.23 |
| Ac-SEQ ID NO: 57-NH$_2$ | 1182.32 | 1182.04 ± 1.25 |
| Ac-SEQ ID NO: 58-NH$_2$ | 1174.34 | 1175.64 ± 1.62 |
| Ac-SEQ ID NO: 59-NH$_2$ | 1131.23 | 1130.82 ± 0.66 |
| Ac-SEQ ID NO: 62-NH$_2$ | 1168.30 | 1168.28 ± 0.33 |
| Ac-SEQ ID NO: 73-NH$_2$ | 1133.2 | 1133.47 ± 2.18 |
| Ac-SEQ ID NO: 74-NH$_2$ | 1161.26 | 1161.19 ± 0.67 |
| Ac-SEQ ID NO: 76-NH$_2$ | 1147.22 | 1148.26 ± 1.83 |
| Ac-SEQ ID NO: 77-NH$_2$ | 1184.30 | 1184.34 ± 0.13 |

Example 11

Study of the Inhibition of the SNARE Complex Formation with Detection of the Complex by ELISA With the aim of determining the capacity of inhibition of the SNARE complex formation by the compounds of the invention, the competitive inhibition of the compounds compared to SNAP-25 was studied with regards to the formation of this complex. The proportion of SNARE complex formed was determined by the ELISA technique, using one of the proteins from the complex bound to GST. In a 96-well plate VAMP was immobilized (using a 0.037 μM solution) and subsequently the free spaces were blocked with BSA (3%). Parallel to this process, SNAP-25 bound to GST (0.0185 μM), syntaxin (0.037 μM) and a compound of the invention (2.5 mM and 0.5 mM compounds) were incubated for 1 hour. After incubation, the samples were transferred to the plate with immobilized VAMP and were incubated for 1 hour to allow the formation of the SNARE complex. Afterward, the plate was washed and the complex was detected by a primary antibody anti-GST (Antibody anti-GST epitope TAG, Fisher Cat. no: PA1-982A). The reading was carried out at a wavelength of 490 nm in a TECAN GENios spectrophotometric reader.

Table 4 shows the results of the competitive inhibition of the formation of the SNARE complex by the compounds of the invention versus SNAP-25. The percentage of inhibition of the formation of the complex is inversely proportional to the quantity of SNARE complex spectrophotometrically detected.

TABLE 4

| Compound | % inhibition formation SNARE complex Concentration of compound | |
|---|---|---|
| | 2.5 mM | 0.5 mM |
| Ac-SEQ ID NO: 1-$NH_2$ | 58 | 28 |
| Ac-SEQ ID NO: 2-$NH_2$ | 51 | 19 |
| Ac-SEQ ID NO: 3-$NH_2$ | 51 | 16 |
| Ac-SEQ ID NO: 4-$NH_2$ | 64 | 30 |
| Ac-SEQ ID NO: 5-$NH_2$ | 73 | 35 |
| Ac-SEQ ID NO: 6-$NH_2$ | 68 | 23 |
| Ac-SEQ ID NO: 7-$NH_2$ | 63 | 20 |
| Ac-SEQ ID NO: 8-$NH_2$ | 56 | 18 |
| Ac-SEQ ID NO: 11-$NH_2$ | 75 | 32 |
| Ac-SEQ ID NO: 12-$NH_2$ | 47 | 25 |
| Ac-SEQ ID NO: 14-$NH_2$ | 52 | 12 |
| Ac-SEQ ID NO: 15-$NH_2$ | 52 | 13 |
| Ac-SEQ ID NO: 18-$NH_2$ | 75 | 30 |
| Ac-SEQ ID NO: 19-$NH_2$ | 68 | 19 |
| Ac-SEQ ID NO: 20-$NH_2$ | 57 | 25 |
| Ac-SEQ ID NO: 21-$NH_2$ | 56 | 22 |
| Ac-SEQ ID NO: 23-$NH_2$ | 55 | Not studied |
| Ac-SEQ ID NO: 25-$NH_2$ | 56 | 17 |
| Ac-SEQ ID NO: 26-$NH_2$ | 61 | 2 |
| Ac-SEQ ID NO: 27-$NH_2$ | 69 | 34 |
| Ac-SEQ ID NO: 28-$NH_2$ | 60 | 18 |
| Ac-SEQ ID NO: 29-$NH_2$ | 60 | 21 |
| Ac-SEQ ID NO: 33-$NH_2$ | 49 | 5 |
| Ac-SEQ ID NO: 34-$NH_2$ | 68 | 26 |
| Ac-SEQ ID NO: 35-$NH_2$ | 65 | 15 |
| Ac-SEQ ID NO: 36-$NH_2$ | 64 | 6 |
| Ac-SEQ ID NO: 40-$NH_2$ | Not studied | 42 |
| Ac-SEQ ID NO: 47-$NH_2$ | 53 | Not studied |
| Ac-SEQ ID NO: 48-$NH_2$ | 83 | 43 |
| Ac-SEQ ID NO: 50-$NH_2$ | 57 | 15 |
| Ac-SEQ ID NO: 51-$NH_2$ | 90 | 63 |
| Ac-SEQ ID NO: 52-$NH_2$ | 64 | 11 |
| Ac-SEQ ID NO: 53-$NH_2$ | 67 | 21 |
| Ac-SEQ ID NO: 56-$NH_2$ | 65 | 31 |
| Ac-SEQ ID NO: 57-$NH_2$ | 68 | 31 |
| Ac-SEQ ID NO: 58-$NH_2$ | 68 | 26 |
| Ac-SEQ ID NO: 59-$NH_2$ | 65 | 56 |
| Ac-SEQ ID NO: 62-$NH_2$ | 62 | 37 |
| Ac-SEQ ID NO: 74-$NH_2$ | Not studied | 34 |

Example 12

Study of the Inhibition of the SNARE Complex Formation with Detection of the Complex by Electrophoresis VAMP (6 µM), syntaxin (6 µM) and the compound of the invention (5 mM or 1 mM compounds) were incubated for 3 hours. Subsequently, SNAP-25 (0.6 µM) was added and the mixture was incubated for an additional 15 hours to allow the formation of the SNARE complex. After incubation, the loading buffer (Laemli Simple Buffer) was added and the mixture was analyzed by 10% acrylamide SDS-PAGE in gel. The amount of complex was determined by MediaCybernetics image analysis software Image-Pro Plus.

Table 5 shows the results of the inhibition of the formation of the SNARE complex. The percentage of inhibition of the formation of the complex is inversely proportional to the quantity of SNARE complex detected.

TABLE 5

| Compound | % inhibition formation SNARE complex Concentration of compound | |
|---|---|---|
| | 5 mM | 1 mM |
| Ac-SEQ ID NO: 5-$NH_2$ | 100 | 100 |
| Ac-SEQ ID NO: 11-$NH_2$ | 100 | 76 |
| Ac-SEQ ID NO: 27-$NH_2$ | 100 | 78 |
| Ac-SEQ ID NO: 48-$NH_2$ | 100 | 4 |
| Ac-SEQ ID NO: 51-$NH_2$ | 100 | 41 |
| Ac-SEQ ID NO: 59-$NH_2$ | 82 | 16 |
| Ac-SEQ ID NO: 62-$NH_2$ | 80 | 72 |

Example 13

Quantification of the Release of Noradrenaline Induced by TPA/Ionomycin in a Neuroblastoma Cell Line by ELISA The induction of the release of noradrenaline with TPA (12-O-tetradecanoylphorbol-13-acetate)/Ionomycin enables direct measurement of neuronal exocytosis. For the study of the inhibitory effect of the compounds of the invention on the release of noradrenaline, cells of a human neuroblastoma cell line were pre-incubated ($1 \times 10^8$ cells/well) for 60 minutes with the compound of the invention (1 µM, 10 µM, 100 µM, 500 µM or 1 mM compounds), and afterward the release of noradrenaline was induced. The release of the noradrenaline neurotransmitter was induced by an 8 minute pre-treatment with a solution of 12-O-tetradecanoylphorbol-13-acetate (TPA) 100 nM, which mobilized the intracellular vesicles which contained the neurotransmitter; followed by a 5 minute incubation with TPA/Ionomycin (100 nM/10 µM), which induced the release of the neurotransmitter contained in these vesicles. The quantity of neurotransmitter released into the growth medium was quantified by ELISA (Noradrenaline ELISA kit, IBL International ref. RE59261), in an assay mediated by specific antibodies against noradrenaline and completed by an enzymatic reaction based on the reaction of alkaline phosphatase, which resulted in a quantifiable color indication. For this, absorbance at 405 nm was measured in Thermo Scientific Multiskan Ascent equipment.

The blocking of the SNARE complex by the compounds of the invention lead to an inhibition of neuronal exocytosis and therefore, a decrease in the levels of released noradrenaline (Table 6).

TABLE 6

| TREATMENT | DOSE | % RELEASED NORADRENALINE | |
|---|---|---|---|
| | | Average | SEM |
| TPA/ION | | 100.00 | 3.11 |
| Ac-SEQ ID NO: 5-$NH_2$ | 10 µM | 85.68 | 8.81 |
| | 100 µM | 81.50 | 3.94 |
| | 1000 µM | 51.45 | 0.35 |
| Ac-SEQ ID NO: 51-$NH_2$ | 10 µM | 81.13 | 11.13 |
| | 100 µM | 101.40 | 9.38 |
| | 1000 µM | 35.37 | 1.84 |
| Ac-SEQ ID NO: 62-$NH_2$ | 10 µM | 77.76 | 8.74 |
| | 100 µM | 82.72 | 5.58 |
| | 1000 µM | 63.99 | 3.61 |

Example 14

Prophetic Preparation of a Cosmetic Facial Composition Containing Ac-SEQ ID NO:5-$NH_2$.

In a suitable vessel the components of phase A are dissolved. Next, carbomer is slowly added (INCI: CARBOMER) (phase A1), under stirring, until it is completely dissolved. The mixture is heated to 70-75° C.

In another vessel the components of phase B are mixed together and the mixture is heated to 70-75° C.

Next the mixture of phase B is added to the aqueous solution of Phases A+A1, stirred with a turbine to form an emulsion.

The compound Ac-SEQ ID NO:5-NH$_2$, ALDENINE® C (INCI; WATER (AQUA), HYDROLYZED SOY PROTEIN, HYDROLYZED WHEAT PROTEIN, XANTHAN GUM, TRIPEPTIDE-1), aqueous solution of LEUPHASYL® (INCI; WATER (AQUA), GLYCERIN, PENTAPEPTIDE-18, CAPRYLYL GLYCOL), SILICONE DC 200 (INCI: DIMETHICONE) and SILICONE DC 245 (INCI: CYCLOPENTASILOXANE) (phase C), are added stepwise under stirring to the previous emulsion at 40° C. until homogenization. Next, perfume (INCI: FRAGRANCE (PARFUM)) (phase D), is slowly added under stirring until homogenized.

Finally, the pH of the mixture is adjusted to 5.5-7.0 with aqueous solution of 20% sodium hydroxide.

TABLE 7

| Phase | Cosmetic facial composition INGREDIENT | % in weight |
|---|---|---|
| A | WATER (AQUA) | q.s.p. 100 |
| A | DISODIUM EDTA | 0.30 |
| A | PHENONIP ® (INCI: PHENOXYETHANOL, METHYLPARABEN, ETHYLPARABEN, BUTYLPARABEN, PROPYLPARABEN, ISOBUTYLPARABEN). | |
| | PHENOXYETHANOL, | 0.610 |
| | METHYLPARABEN | 0.130 |
| | ETHYLPARABEN | 0.033 |
| | BUTYLPARABEN | 0.033 |
| | PROPYLPARABEN | 0.017 |
| | ISOBUTYLPARABEN | 0.017 |
| A | IMIDAZOLIDINYL UREA | 0.20 |
| A | GLYCERIN | 3.00 |
| A1 | CARBOMER | 0.60 |
| B | MINERAL OIL (PARAFFINUM LIQUIDUM) | 7.00 |
| B | BHT | 0.05 |
| B | CETYL ALCOHOL | 0.80 |
| B | BEESWAX (CERAALBA) | 0.50 |
| B | STEARYL ALCOHOL | 1.50 |
| B | LIPOMULSE ®165 (INCI: GLYCERYL STEARATE, PEG-100 STEARATE): | |
| | GLYCERYL STEARATE | 1.25 |
| | PEG-100 STEARATE | 1.25 |
| B | DIMETHYLMETHOXY CHROM ANOL | 0.01 |
| B | BENZOPHENONE-3 | 0.20 |
| B | ETHYLHEXYL METHOXYCINNAMATE | 0.90 |
| B | CETEARYL ALCOHOL | 1.00 |
| C | Ac-SEQ ID NO: 5-NH$_2$ | 0.10 |
| C | ALDENINE ® C (INCI: WATER (AQUA), HYDROLYZED SOY PROTEIN, HYDROLYZED WHEAT PROTEIN, XANTHAN GUM, TRIPEPTIDE-1): | |
| | WATER (AQUA) | 1.195 |
| | HYDROLYZED SOY PROTEIN | 0.500 |
| | HYDROLYZED WHEAT PROTEIN | 0.300 |
| | XANTHAN GUM | 0.003 |
| | TRIPEPTIDE-1 | 0.002 |
| C | LEUPHASYL ® SOLUTION (INCI: WATER (AQUA), GLYCERIN, PENTAPEPTIDE-18, CAPRYLYL GLYCOL): | |
| | WATER (AQUA) | 4.473 |
| | GLYCERIN | 0.500 |
| | PENTAPEPTIDE-18 | 0.003 |
| | CAPRYLYL GLYCOL | 0.024 |
| C | DIMETHICONE | 0.10 |
| C | CYCLOPENTASILOXANE | 1.00 |
| D | FRAGRANCE (PARFUM) | 0.05 |

TABLE 7-continued

| Phase | Cosmetic facial composition INGREDIENT | % in weight |
|---|---|---|
| E | 20% SODIUM HYDROXIDE | g.s.p. pH 5.5-7 |

Example 15

Preparation of a Cosmetic Facial Composition Containing Ac-SEQ ID NO:51-NH$_2$

In a suitable vessel the components from phase A were dissolved and the mixture was healed to 70-75° C.

Next the mixture of phase B was added to the aqueous solution of Phase A under turbine stirring to form an emulsion. The emulsion was heated to 40° C. and the compound Ac-SEQ ID NO:51-NH$_2$, aqueous solution of ARGIRELINE® (INCI: WATER (AQUA), ACETYL HEXAPEPTIDE-8) and ANTARCTICINE® (INCI: WATER (AQUA), PSEUDOALTEROMONAS FERMENT EXTRACT) (phase C) were added under stirring. Finally, the perfume (INCI: FRAGRANCE (PARFUM) (phase D) was added.

TABLE 8

| Phase | Cosmetic facial composition INGREDIENT | % in weight |
|---|---|---|
| A | WATER (AQUA) | q.s.p. 100 |
| A | GLYCERIN | 3.00 |
| A | MAGNESIUM SULFATE | 1.00 |
| A | PHENONIP ® (INCI: PHENOXYETHANOL, METHYLPARABEN, ETHYLPARABEN, BUTYLPARABEN, PROPYLPARABEN, ISOBUTYLPARABEN). | |
| | PHENOXYETANOL, | 0.363 |
| | METHYLPARABEN | 0.077 |
| | ETHYLPARABEN | 0.020 |
| | BUTYLPARABEN | 0.020 |
| | PROPYLPARABEN | 0.010 |
| | ISOBUTYLPARABEN | 0.010 |
| A | DISODIUM EDTA | 0.15 |
| A | IMIDAZOLIDINYL UREA | 0.1 |
| B | MINERAL OIL (PARAFFINUM LIQUIDUM) | 10.00 |
| B | ETHYLHEXYL COCOATE | 10.00 |
| B | CETYL PEG/PPG-10/1 DIMETHICONE | 2.00 |
| B | BEESWAX (CERAALBA) | 1.50 |
| B | HYDROGENATED CASTOR OIL | 1.00 |
| B | TOCOPHERYL ACETATE | 0.10 |
| C | Ac-SEQ ID NO: 5-NH$_2$ | 0.10 |
| C | ARGIRELINE ® SOLUTION (INCI: WATER (AQUA), ACETYL HEXAPEPTIDE-8): | |
| | WATER (AQUA) | 9.995 |
| | ACETYL HEXAPEPTIDE-8 | 0.005 |
| C | ANTARCTICINE ® (INCI: WATER (AQUA), PSEUDOALTEROMONAS FERMENT EXTRACT): | |
| | WATER (AQUA) | 3.750 |
| | PSEUDOALTEROMONAS FERMENT EXTRACT | 1.250 |
| D | FRAGRANCE (PARFUM) | 0.10 |

Example 16

Preparation of a Face Cream Containing Ac-SEQ ID NO:11-NH$_2$.

In a suitable vessel pentylene glycol [INCI: PENTYLENE GLYCOL], BENZYL ALCOHOL [INCI: BENZYL ALCOHOL], INYLINE™ [INCI: ACETYL HEXAPEPTIDE-30] and the compound Ac-SEQ ID NO:11 NH$_2$ (phase A) were dissolved in water under constant, light stirring.

Once homogenized, carbomer [INCI: CARBOMER] (phase A1) was added and the mixture was stirred until completely dissolved. Next, potassium cetyl phosphate [INCI: POTASSIUM CETYL PHOSPHATE] (phase A2) was added until it was dispersed and the whole mixture was heated to 70-75° C.

In a separate vessel the components of phase B were mixed together, heated to 70-75° C. and, once homogenized, phase B was added little by little to phase A under constant stirring.

With the mixture at about 50° C., phase C was slowly added maintaining stirring. Phase D was then added until homogenization.

Once the mixture was homogenized, the pH was adjusted to 6.0-6.5 with phase E. Finally, the perfume was added (phase F).

TABLE 9

| Phase | Face cream composition<br>INGREDIENT | % in weight |
|---|---|---|
| A | WATER (AQUA) | q.s.p. 100 |
| A | PENTYLENE GLYCOL | 5.0 |
| A | BENZYL ALCOHOL | 0.40 |
| A | Ac-SEQ ID: 11-NH$_2$ | 0.10 |
| A | ACETYL HEXAPEPTIDE-30 | 0.05 |
| A1 | CARBOMER | 0.50 |
| A2 | POTASSIUM CETYL PHOSPHATE | 0.50 |
| B | SOYBEAN (GLYCINE SOJA) OIL | 5.00 |
| B | PHYTOCREAM 2000 ® (INCI: GLYCERYL STEARATE, CETEARYL ALCOHOL, POTASSIUM PALMITOYL HYDROLYZED WHEAT PROTEIN): | |
| | GLYCERYL STEARATE | 2.050 |
| | CETEARYL ALCOHOL | 2.050 |
| | POTASSIUM PALMITOYL HYDROLYZED WHEAT PROTEIN | 0.900 |
| B | ETHYLHEXYL COCOATE | 2.00 |
| B | PHENOXYETHANOL | 0.90 |
| C | DIMETHICONE | 1.00 |
| D | SEPIGEL ™ 305 (INCI: POLYACRYLAMIDE, WATER (AQUA), C13-14 ISOPARAFFIN, LAURETH-7) | 0.400 |
| | POLYACRYLAMIDE | 0.340 |
| | WATER (AQUA) | 0.200 |
| | C13-14 ISOPARAFFIN | 0.060 |
| | LAURETH-7 | |
| E | 20% SODIUM HYDROXIDE | q.s.p. pH 6.0-6.5 |
| F | FRAGRANCE (PARFUM) | 0.20 |

Example 17

Preparation of an Antiperspirant Serum Containing Ac-SEQ ID NO:62-NH$_2$.

In a suitable vessel Phase B was stirred until it dissolved. In another vessel, the ingredients from phase C were heated until completely dissolved, and phase C was added, under stirring, to phase B.

In a separate vessel the compound Ac-SEQ ID NO:62-NH$_2$ and PHENONIP® [INCI: PHENOXYETHANOL, METHYLPARABEN, ETHYLPARABEN, BUTYLPARABEN, PROPYLPARABEN, ISOBUTYLPARABEN] (phase A) were dissolved in water, under stirring.

Finally, phase A was added to the mixture of phases B+C, under stirring until homogenized.

TABLE 10

| Phase | Antiperspirant serum composition<br>INGREDIENT | % in weight |
|---|---|---|
| A | WATER (AQUA) | 0.50 |
| A | Az-SEQ ID NO: 62-NH$_2$ | 0.50 |
| A | PHENONIP ® (INCI: PHENOXYETHANOL, METHYLPARABEN, ETHYLPARABEN, BUTYLPARABEN, PROPYLPARABEN, ISOBUTYLPARABEN): | |
| | PHENOXYETHANOL | 0.36 |
| | METHYLPARABEN | 0.08 |
| | ETHYLPARABEN | 0.02 |
| | BUTYLPARABEN | 0.02 |
| | PROPYLPARABEN | 0.01 |
| | ISOBUTYLPARABEN | 0.01 |
| B | SILICONE 9040 (INCI: CYCLOPENTASILOXANE, DIMETHICONE CROSSPOLYMER): | |
| | CYCLOPENTASILOXANE | 43.265 |
| | DIMETHICONE CROSSPOLYMER | 7.635 |
| | CYCLOPENTASILOXANE | 31.36 |
| B | FRAGRANCE (PARFUM) | 0.13 |
| C | ETHYLHEXYL COCOATE | 12.43 |
| C | C24-28 ALKYL DIMETHICONE | 2.25 |
| C | LECITHIN | 1.38 |
| C | BHT | 0.05 |

Example 18

Prophetic Preparation of a Face Cream Containing Palm-SEQ ID NO:48-NH$_2$

In a suitable vessel pentylene glycol (PENTYLENE GLYCOL), benzyl alcohol (INCI: BENZYL ALCOHOL), glycerol (INCI: GLYCEROL), urea (INCI: UREA) and the compound Palm-SEQ ID NO:48-NH$_2$ (phase A) are dissolved in water. Next, carbomer (INCI: CARBOMER) (phase A1) is slowly added, under stirring, until it is completely dissolved. The mixture is heated to 70-75° C.

the mixture of phase B is added to the aqueous solution of Phases A+A1 under turbine stirring to form an emulsion.

The perfume (INCI: FRAGRANCE (PARFUM) (phase C) is added to the previous emulsion at 40° C.

Finally, the pH of the mixture is adjusted to 6.0-6.5 with aqueous solution of 20% sodium hydroxide when required.

TABLE 11

| Phase | Face cream composition<br>INGREDIENT | % in weight |
|---|---|---|
| A | WATER (AQUA) | q.s.p. 100 |
| A | PENTYLENE GLYCOL | 5.0 |
| A | BENZYL ALCOHOL | 0.40 |
| A | GLYCERIN | 1.00 |
| A | UREA | 1.00 |
| A | Palm-SEQ ID NO: 48-NH$_2$ | 0.10 |
| A1 | CARBOMER | 0.60 |
| B | LIPOMULSE ® 165 (INCI: GLYCERYL STEARATE, PEG-100 STEARATE): | |
| | GLYCERYL STEARATE | 1.500 |
| | PEG-100 STEARATE | 1.500 |
| B | CETEARETH-25 | 2.00 |
| B | SHEA BUTTER (*BUTYROSPERMUM PARKII*) | 2.00 |
| B | CAPRYLIC/CAPRIC TRIGLYCERIDE | 1.00 |
| B | ETHYLHEXYL COCOATE | 7.00 |
| B | PHENOXYETHANOL | 0.90 |
| B | DIMETHICONE | 1.00 |
| C | FRAGRANCE (PARFUM) | 0.20 |
| D | 20% SODIUM HYDROXIDE | q.s.p. pH 6.0-0.5 |

Example 19

Prophetic Preparation of Liposomes Containing Palm-SEQ ID NO:59-NH$_2$

Dipalmitoylphosphatidylcholine (DPPC) is weighed and dissolved in chloroform. The solvent is evaporated to dryness until a fine layer of phospholipid is obtained, and this layer is hydrated by treatment with an aqueous solution which contains the compound at the desired concentration (containing PHENONIP®) at 55° C., obtaining the MLV liposomes. The ULV liposomes are obtained by submerging the MLV liposomes in an ultrasound bath at 55° C. for 8 cycles of 2 minutes at intervals of 5 minutes.

TABLE 12

| INGREDIENT | % IN WEIGHT |
|---|---|
| WATER (AQUA) | q.s.p. 100 |
| DIPALMITOYLPHOSPHATIDYLCHOLINE | 4.00 |
| Palm-SEQ ID NO: 59-NH$_2$ | 0.20 |
| PHENONIP ® (INCI: PHENOXYETHANOL, METHYLPARABEN, ETHYLPARABEN, BUTYLPARABEN, PROPYLPARABEN, ISOBUTYLPARABEN): | |
| ISOBUTYLPARABEN | 0.01 |
| PHENOXYETHANOL | 0.36 |
| METHYLPARABEN | 0.08 |
| ETHYLPARABEN | 0.02 |
| BUTYLPARABEN | 0.02 |
| PROPYLPARABEN | 0.01 |

Example 20

Preparation of a Water in Oil (w/o) Microemulsion Containing Ac-SEQ ID NO:27-NH$_2$.

In a suitable vessel caprylic/capric triglyceride [INCI: CAPRYLIC/CAPRIC TRIGLYCERIDE], oleic acid [INCI: OLEIC ACID], Edenor LS2M GS [INCI: STEARIC ACID, PALMITIC ACID] and ceramide [INCI: CERAMIDE 3] (phase A1 ingredients) were mixed together, and the mixture was heated to 80-85° C.

Beta sitosterol [INCI: BETA-SITOSTEROL] (phase A2) and Glycosylceramides IRB3 [INCI; LECITHIN, GLYCOLIPIDS] (phase A3) were added under constant stirring and the mixture was allowed to cool to 40° C.

Evening primrose oil [INCI; EVENING PRIMROSE (*OENOTHERA BIENNIS*) OIL], borage seed oil [INCI; *BORAGO OFFICINALIS* SEED OIL], Vitamin F Glyceryl Ester CLR™ [INCI: GLYCERYL LINOLEATE, GLYCERYL LINOLENATE], and tocopheryl Acetate [INCI: TOCOPHERYL ACETATE] (phase B ingredients) were mixed together under stirring and mixed with phase A at 40° C.

In a separate vessel isostearic acid [INCI: ISOSTEARIC ACID] and Pearlagent™ GM4175 [INCI: WATER (AQUA), SODIUM LAURETH SULFATE, GLYCOL STEARATE, COCAMIDE MEA, COCAMIDE DEA, PROPYLENE GLYCOL, PHENOXYETHANOL, BENZOIC ACID, DEHYDROACETIC ACID] (phase C ingredients) were mixed together under stirring and then denatured alcohol was added [INCI: ALCOHOL DENAT], Palm-SEQ ID NO:27-NH$_2$ (phase C1 ingredients). This mixture of phases C and C1 was poured onto the first mixture of phase A1, A2, A3 and phase B under constant stirring, obtaining a cosmetic composition with the proportions shown in Table 13.

TABLE 13

| Phase | Microemulsion INGREDIENT | % in weight |
|---|---|---|
| A1 | CAPRYLIC/CAPRIC TRIGLYCERIDE | q.s.p. 100 |
| A1 | OLEIC ACID | 0.018 |
| A1 | EDENOR L2SM GS [INCI: STEARIC ACID, PALMITIC ACID]: | |
| | STEARIC ACID | 0.00225 |
| | PALMITIC ACID | 0.00225 |
| A1 | CERAMIDE 3 | 0.0045 |
| A2 | BETA SITOSTEROL | 0.0225 |
| A3 | GLYCOSYLCERAMIDES IRB 3 [INCI: LECITHIN, GLYCOLIPIDS]: | |
| | LECITHIN | 0.0131 |
| | GLYCOLIPIDS | 0.0004 |
| B | EVENING PRIMROSE (OENOTHERA BIENNIS) OIL | 9 |
| B | BORAGO OFFICINALIS SEED OIL | 9 |
| B | VITAMIN F GLYCERYL ESTER CLR ™ [INCI: GLYCERYL LINOLEATE, GLYCERYL LINOLENATE]: | |
| | GLYCERYL LINOLEATE | 4.05 |
| | GLYCERYL LINOLENATE | 0.45 |
| B | TOCOPHERYL ACETATE | 0.45 |
| C | ISOSTEARIC ACID | 7.87 |
| C | PEARLAGENT ™ GM4175 [INCI: WATER (AQUA), SODIUM LAURETH SULFATE, GLYCOL STEARATE, COCAMIDE MEA, COCAMIDE DEA, PROPYLENE GLYCOL, PHENOXYETHANOL, BENZOIC ACID, DEHYDROACETIC ACID]: | |
| | WATER (AQUA) | 0.8055 |
| | SODIUM LAURETH SULFATE | 0.2433 |
| | GLYCOL STEARATE | 0.2433 |
| | COCAMIDE ME | 0.0417 |
| | COCAMIDE DEA | 0.0417 |
| | PROPYLENE GLYCOL | 0.0076 |
| | PHENOXYETHANOL | 0.0056 |
| | BENZOIC ACID | 0.0008 |
| | DEHYDROACETIC ACID | 0.0006 |
| C1 | ALCOHOL DENAT. | 0.745 |
| C1 | Ac-SEQ ID NO: 27-NH$_2$ | 0.001 |

Example 21

Preparation of Coacervation Capsules Containing the Compound Palm-SEQ ID NO:51-NH$_2$ a) Preparation of an Emulsion of the Compound Palm-SEQ ID NO:51-NH$_2$ In a suitable vessel the compound was dissolved in water (phase A) heating the mixture to 70° C. In a separate vessel soybean oil [INCI: SOYBEAN (GLYCINE SOJA) OIL], Abil EM 90 [INCI: CETYL PEP/PPG-10/1 DIMETHICONE] and Span 65 [INCI: SORBITAN TRISTEARATE] (phase B) were mixed together, heating the mixture to 80° C. until the Span 65 dissolved. Once melted, phase A was added to phase B slowly under intense stirring with a turbine. Once the components were mixed together, the mixture was stirred until it reached room temperature.

TABLE 14

| Phase | INGREDIENT | % in weight |
|---|---|---|
| A | PURIFIED WATER | 56.00 |
| B | SOYBEAN (*GLYCINE SOJA*) OIL | 33.00 |
| B | CETYL PEG/PPG-10/1 DIMETHICONE | 5.00 |
| B | SORBITAN TRISTEARATE | 4.00 |
| A | Palm-SEQ ID NO: 51-NH$_2$ | 2.00 | b) Preparation of a Microfluidized Emulsion of the Compound Palm-SEQ ID No:51-NH$_2$ The components of phase A were mixed together in water: Zemea Propanediol [INCI: PROPANEDIOL], phenoxyethanol [INCI: PHENOXYETHANOL], Structure XL [INCI: Hydroxypropyl starch phosphate], Amigel [INCI: SCLEROTIUM GUM] and powdered hyaluronic acid [INCI: SODIUM HYALURONATE], the mixture was heated to 70° C. under stirring. In another vessel, the emulsion from section a), and the components of phase B: Massocare HD [INCI: ISOHEXADECANE], Arlacel 83 [INCI: SORBITAN SESQUIOLEATE], LIPOCHROMAN™ [INCI: DIMETHYLMETHOXY CHROMANOL] were mixed together, and the mixture was heated to 80° C. under stirring.

Once this temperature was reached, phase B was added to phase A very slowly under intense stirring with a turbine.

The sample was passed, without cooling, through a microfluidizer for three cycles at an entrance pressure of 80 bar and an exit pressure of 15000 psi, maintaining the operating temperature between 65 and 75° C. Once microfluidized, the emulsion was stirred with a rotor until room temperature was reached.

TABLE 15

| Phase | INGREDIENT | % in weight |
|---|---|---|
| A | WATER (AQUA) | 70.36 |
| B | Emulsion section a) | 10.95 |
| B | ISOHEXADECANE | 5.48 |
| A | PROPANEDIOL | 5.48 |
| B | SORBITAN SESQUIOLEATE | 4.38 |
| A | PHENOXYETHANOL | 2.85 |
| A | HYDROXYPROPYL STARCH PHOSPHATE | 0.33 |
| A | SCLEROTIUM GUM | 0.11 |
| B | DIMETHYLMETHOXY CHROMANOL | 0.05 |
| A | SODIUM HYALURONATE | 0.01 | c) Obtaining Coacervate Capsules Containing the Compound Palm-SEQ ID NO:51-NH$_2$ In a vessel the emulsion from section b) (phase A) was weighed. In another vessel Sensomer CI 50 [INCI: WATER (AQUA); STARCH HYDROXYPROPYLTRIMONIUM CHLORIDE; UREA; SODIUM LACTATE; SODIUM CHLORIDE; SODIUM BENZOATE] was dissolved in water (phase B). Phase B was added to phase A under intense stirring.

Amigel [INCI: SCLEROTIUM GUM] (phase C) was added to the previous mixture very slowly and under intense stirring. The mixture was stirred for 2 hours to obtain good hydration of the gum.

Next, Structure XL [INCI: HYDROXYPROPYL STARCH PHOSPHATE] (phase D) was added, maintaining the stirring for another hour to obtain the complete hydration of the biopolymers added.

Finally, Sepigel™ 305 [INCI: POLYACRYLAMIDE; WATER (AQUA), C13-14 ISOPARAFFIN; LAURETH-7] (phase E) was added, maintaining the stirring until a homogenous suspension was obtained. The average size of the capsules in suspension obtained determined by Dynamic Laser Light Scattering was approximately 300 nm.

TABLE 16

| Phase | INGREDIENT | % in weight |
|---|---|---|
| A | Emulsion section b) | 91.30 |
| B | WATER (AQUA) | 6.00 |
| D | HYDROXYPROPYL STARCH PHOSPHATE | 1.50 |
| C | SCLEROTIUM GUM | 0.75 |
| E | SEPIGEL ™ 305 (INCI: POLYACRYLAMIDE, WATER (AQUA), C13-14 ISOPARAFFIN, LAURETH-7): | |
| | POLYACRYLAMIDE | 0.10 |
| | WATER (AQUA) | 0.085 |
| | C13-14 ISOPARAFFIN | 0.05 |
| | LAURETH-7 | 0.015 |
| B | SENSOMER CI 50 [INCI: WATER (AQUA); STARCH HYDROXYPROPYLTRIMONIUM CHLORIDE; UREA; SODIUM LACTATE; SODIUM CHLORIDE; SODIUM BENZOATE]: | |
| | WATER (AQUA) | 0.137 |
| | STARCH HYDROXYPROPYLTRIMONIUM CHLORIDE | 0.048 |
| | UREA | 0.006 |
| | SODIUM LACTATE | 0.004 |
| | SODIUM CHLORIDE | 0.004 |
| | SODIUM BENZOATE | 0.001 |

The Sequence listing entitled 788767_1.txt filed herewith is incorporated by reference herein in its entirety.

It will be appreciated that variants of the above-disclosed and other features and functions, or alternatives thereof, may be combined into many other different systems or applications. Various presently unforeseen or unanticipated alternatives, modifications, variations or improvement therein may be subsequently made by those skilled in the art which are also intended to be encompassed by the following claims.

The invention claimed is:

1. A compound of general formula (I):

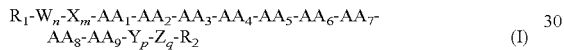
(I)

its stereoisomers, mixtures thereof and/or its cosmetically or pharmaceutically acceptable salts, wherein:

$AA_1$ is selected from the group consisting of -Arg-, -His-, -Lys-, -Gln-, -Asn-, -Glu- and -Asp-;

$AA_2$ is selected from the group consisting of -Arg-, -His-, -Lys-, -Gln-, -Asn-, -Glu- and -Asp-;

$AA_3$ is selected from the group consisting of -Glu- and;

$AA_4$ is -His-;

$AA_5$ is selected from the group consisting of -Arg-, -His-, -Lys-, -Gln-, and -Asn-;

$AA_6$ is -Lys-;

$AA_7$ is selected from the group consisting of -Met-, -MetO- and -MetO$_2$-;

$AA_8$ is -Asp-;

$AA_9$ is a bond;

W, X, Y, Z are amino acids and are independently selected from amongst themselves;

n, m, p and q are independently selected from amongst themselves and have a value of 0 or 1;

n+m+p+q is smaller than or equal to 2;

$R_1$ is selected from the group consisting of H, a polymer derived from polyethylene glycol, a non-cyclic substituted or unsubstituted aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group consisting of H, a non-cyclic substituted or unsubstituted aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;

$R_2$ is selected from the group consisting of —NR$_3$R$_4$, —OR$_3$ and —SR$_3$ wherein $R_3$ and $R_4$ are independently selected from the group consisting of H, a polymer derived from polyethylene glycol, a non-cyclic substituted or unsubstituted aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl;

wherein at least one of:

$R_1$ is not H, and $R_2$ is not OH, and $R_1$ and $R_2$ are not α-amino acids.

2. A compound of general formula (I):

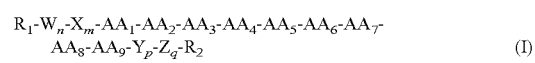
(I)

its stereoisomers, mixtures thereof and/or its cosmetically or pharmaceutically acceptable salts, wherein:

$AA_1$ is selected from the group consisting of -L-Asn-, -L-Gln-, -L-His- and -L-Asp-, $AA_2$ is selected from the group consisting of -L-His-, -L-Gln- and -L-Asn-, $AA_3$ is selected from the group consisting of -L-Glu-, -L-Leu- and -L-Phe-, $AA_4$ is selected from the group consisting of -L-His- and -L-Glu-, $AA_5$ is selected from the group consisting of -L-Arg-, -L-Gln-, -L-Asn- and -L-His-, $AA_6$ is selected from the group consisting of -L-Ile- and -L-Lys-, $AA_7$ is selected from the group consisting of -L-Met-, -L-MetO- and -L-MetO$_2$-, $AA_8$ is -L-Asp-, $AA_9$ is selected from the group consisting of -L-Gln-, -L-Asn-, and a bond, W, X, Y, Z are amino acids and are independently selected from amongst themselves;

n, m, p and q are independently selected from amongst themselves and have a value of 0 or 1;

n+m+p+q is smaller than or equal to 2;

$R_1$ is selected from the group consisting of H, acetyl, lauroyl, myristoyl and palmitoyl; and R$_2$ is selected from the group consisting of —NR$_3$R$_4$ and —OR$_3$ wherein R$_3$ and R$_4$ are independently selected from H, methyl, ethyl, hexyl, dodecyl and hexadecyl;
  wherein at least one of:
    R$_1$ is not H, and
    R$_2$ is not OH, and
    R$_1$ and R$_2$ are not α-amino acids.

3. The compound according to claim 2, wherein R$_1$ is selected from the group consisting of H, acetyl, lauroyl, myristoyl and palmitoyl, AA$_1$ is -L-His-, AA$_2$ is -L-Gln-, AA$_3$ is -L-Glu-, AA$_4$ is -L-His-, AA$_5$ is -L-Arg-, AA$_6$ is -L-Lys-, AA$_7$ is -L-Met-, -L-MetO- or -L-MetO$_2$-, AA$_8$ is -L-Asp-, AA$_9$ is a bond and R$_2$ is —NR$_3$R$_4$ or —OR$_3$ wherein R$_3$ and R$_4$ are independently selected from H, methyl, ethyl, hexyl, dodecyl and hexadecyl.

4. The compound according to claim 2, wherein R$_1$ is selected from the group consisting of H, acetyl, lauroyl, myristoyl and palmitoyl, AA$_1$ is -L-Asp-, AA$_2$ is -L-Gln-, AA$_3$ is -L-Glu-, AA$_4$ is -L-His-, AA$_5$ is -L-Gln-, AA$_6$ is -L-Lys-, AA$_7$ is -L-Met-, -L-MetO- or -L-MetO$_2$-, AA$_8$ is -L-Asp-, AA$_9$ is a bond and R$_2$ is —NR$_3$R$_4$ or —OR$_3$ wherein R$_3$ and R$_4$ are independently selected from H, methyl, ethyl, hexyl, dodecyl and hexadecyl.

5. The compound according to claim 2, wherein R$_1$ is selected from the group consisting of H, acetyl, lauroyl, myristoyl and palmitoyl, AA$_1$ is -L-Gln-, AA$_2$ is -L-His-, AA$_3$ is -L-Phe-, AA$_4$ is -L-His-, AA$_5$ is -L-Gln-, AA$_6$ is -L-Lys-, AA$_7$ is -L-Met-, -L-MetO- or -L-MetO$_2$-, AA$_8$ is -L-Asp-, AA$_9$ is a bond and R$_2$ is —NR$_3$R$_4$ or —OR$_3$ wherein R$_3$ and R$_4$ are independently selected from H, methyl, ethyl, hexyl, dodecyl and hexadecyl.

6. The compound according to claim 2, wherein R$_1$ is selected from the group consisting of H, acetyl, lauroyl, myristoyl and palmitoyl, AA$_1$ is -L-Asn-, AA$_2$ is -L-Asn-, AA$_3$ is -L-Leu-, AA$_4$ is -L-Glu-, AA$_5$ is -L-Asn-, AA$_6$ is -L-Ile-, AA$_7$ is -L-Met-, -L-MetO- or -L-MetO$_2$-, AA$_8$ is -L-Asp-, AA$_9$ is -L-Gln- or -L-Asn- and R$_2$ is —NR$_3$R$_4$ or OR$_3$ wherein R$_3$ and R$_4$ are independently selected from H, methyl, ethyl, hexyl, dodecyl and hexadecyl.

7. The compound according to claim 2, wherein R$_1$ is selected from the group consisting of H, acetyl, lauroyl, myristoyl and palmitoyl, AA$_1$ is -L-Gln-, AA$_2$ is -L-Gln-, AA$_3$ is -L-Leu-, AA$_4$ is -L-Glu-, AA$_5$ is -L-Asn-, AA$_6$ is -L-Ile-, AA$_7$ is -L-Met-, -L-MetO- or -L-MetO$_2$-, AA$_8$ is -L-Asp-, AA$_9$ is -L-Asn- and R$_2$ is —NR$_3$R$_4$ or OR$_3$ wherein R$_3$ and R$_4$ are independently selected from H, methyl, ethyl, hexyl, dodecyl and hexadecyl.

8. The compound according to claim 2, wherein R$_1$ is selected from the group consisting of H, acetyl, lauroyl, myristoyl and palmitoyl, AA$_1$ is -L-Gln-, AA$_2$ is -L-Asn-, AA$_3$ is -L-Leu-, AA$_4$ is -L-Glu-, AA$_5$ is -L-His-, AA$_6$ is -L-Ile-, AA$_7$ is -L-Met-, -L-MetO- or -L-MetO$_2$-, AA$_8$ is -L-Asp-, AA$_9$ is -L-Gln- and R$_2$ is —NR$_3$R$_4$ or OR$_3$ wherein R$_3$ and R$_4$ are independently selected from H, methyl, ethyl, hexyl, dodecyl and hexadecyl.

9. A cosmetic or pharmaceutical composition which comprises at least one compound of general formula (I), its stereoisomers, mixtures thereof and/or its cosmetically or pharmaceutically acceptable salts, according to claim 1, together with at least one cosmetically or pharmaceutically acceptable excipient or adjuvant.

10. The composition according to claim 9, wherein the compound of general formula (I), its stereoisomers, mixtures thereof and/or its cosmetically or pharmaceutically acceptable salts, is incorporated into a cosmetically or pharmaceutically acceptable delivery system or sustained release system selected from the group consisting of liposomes, mixed liposomes, oleosomes, niosomes, ethosomes, milliparticles, microparticles, nanoparticles, solid lipid nanoparticles, nanostructured lipid carriers, sponges, cyclodextrins, vesicles, micelles, mixed micelles of surfactants, surfactant-phospholipid mixed micelles, millispheres, microspheres, nanospheres, liposheres, millicapsules, microcapsules, nanocapsules, microemulsions and nanoemulsions or is adsorbed on a solid organic polymer or solid mineral support selected from the group consisting of talc, bentonite, silica, starch and maltodextrin.

11. The composition according to claim 9, wherein the composition is presented in a formulation selected from the group consisting of creams, multiple emulsions, anhydrous compositions, aqueous dispersions, oils, milks, balsams, foams, lotions, gels, cream gels, hydroalcoholic solutions, hydroglycolic solutions, hydrogels, liniments, sera, soaps, shampoos, conditioners, serums, polysaccharide films, ointments, mousses, pomades, powders, bars, pencils, sprays, aerosols, capsules, gelatin capsules, soft capsules, hard capsules, tablets, sugar coated tablets, pills, powders, granules, chewing gum, solutions, suspensions, emulsions, syrups, elixirs, jellies and gelatins.

12. The composition according to claim 9, wherein the composition also comprises at least one cosmetically or pharmaceutically acceptable adjuvant selected from the group consisting of agents which inhibit neuronal exocytosis, anticholinergic agents, agents which inhibit muscular contraction, anti-aging agents, anti-wrinkle agents, antiperspirant agents, anti-inflammatory agents and/or analgesics, anti-itching agents, calming agents, anesthetic agents, inhibitors of acetylcholine-receptor aggregation, agents that inhibit acetylcholinesterase, skin relaxant agents, melanin synthesis stimulating or inhibiting agents, whitening or depigmenting agents, propigmenting agents, self-tanning agents, NO-synthase inhibiting agents, 5α-reductase inhibiting agents, lysyl- and/or prolyl hydroxylase inhibiting agents, antioxidants, free radical scavengers and/or agents against atmospheric pollution, reactive carbonyl species scavengers, anti-glycation agents, antihistamine agents, antiviral agents, antiparasitic agents, emulsifiers, emollients, organic solvents, liquid propellants, skin conditioners, humectants, substances that retain moisture, alpha hydroxy acids, beta hydroxy acids, moisturizers, epidermal hydrolytic enzymes, vitamins, amino acids, proteins, pigments, colorants, dyes, biopolymers, gelling polymers, thickeners, surfactants, softening agents, emulsifiers, binding agents, preservatives, agents able to reduce or treat bags under the eyes, exfoliating agents, keratolytic agents, flaking agents, antimicrobial agents, antifungal agents, fungistatic agents, bactericidal agents, bacteriostatic agents, agents stimulating the synthesis of dermal or epidermal macromolecules and/or capable of inhibiting their degradation, collagen synthesis-stimulating agents, elastin synthesis-stimulation agents, decorin synthesis-stimulation agents, laminin synthesis-stimulation agents, defensin synthesis-stimulating agents, chaperone synthesis-stimulating agents, cAMP synthesis-stimulating agents, AQP-3 modulating agents, aquaporin synthesis modulating agents, proteins from the aquaporin family, hyaluronic acid synthesis-stimulating agents, glycosaminoglycan synthesis-stimulating agents, fibronectin synthesis-stimulating agents, sirtuin synthesis-stimulating agents, sirtuin activating agents, heat shock proteins, heat shock protein synthesis-stimulating agents, agents stimulating the synthesis of lipids and components of the stratum corneum, ceramides, fatty acids, agents that inhibit collagen degradation, matrix metalloproteinase inhibitory agents, agents that inhibit elastin degradation, agents that inhibit serine proteases, agents stimulating fibroblast proliferation, agents stimulating keratinocyte proliferation, agents stimulating adipocyte proliferation, agents stimulating melanocyte proliferation, agents stimulating keratinocyte differentiation, agents stimulating or delaying adipocyte differentiation, antihyperkeratosis agents, comedolytic agents, anti-psoriasis agents, DNA repair agents, DNA protecting agents, stabilizers, agents for the treatment and/or care of sensitive skin, firming agents, anti-stretch mark agents, binding agents, agents regulating sebum production, lipolytic agents or agents stimulating lipolysis, adipogenic agents, agents modulating PGC-1α expression, agents modulating PPARγ, agents which increase or reduce the triglyceride content of adipocytes, anti-cellulite agents, agents which inhibit the activity of PAR-2, agents stimulating healing, coadjuvant healing agents, agents stimulating reepithelialization, coadjuvant reepithelialization agents, cytokine growth factors, agents acting on capillary circulation and/or microcirculation, agents stimulating angiogenesis, agents that inhibit vascular permeability, venotonic agents, agents acting on cell metabolism, agents to improve dermal-epidermal junction, agents inducing hair growth, hair growth inhibiting or retardant agents, hair loss retardant agents, preservatives, perfumes, cosmetic and/or absorbent and/or body odor masking deodorants, chelating agents, plant extracts, essential oils, marine extracts, agents obtained from a biotechnological process, mineral salts, cell extracts, sunscreens and organic or mineral photoprotective agents active against ultraviolet A and/or B rays and/or infrared A rays, and mixtures thereof.

13. A compound of general formula (I):

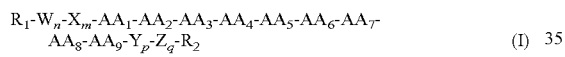

$R_1-W_n-X_m-AA_1-AA_2-AA_3-AA_4-AA_5-AA_6-AA_7-AA_8-AA_9-Y_p-Z_q-R_2$  (I)

its stereoisomers, mixtures thereof and/or its cosmetically or pharmaceutically acceptable salts, wherein:

$AA_1$ is selected from the group consisting of -Arg-, -His-, -Lys-, -Gln-, -Asn-, -Glu- and -Asp-;

$AA_2$ is selected from the group consisting of -Arg-, -His-, -Lys-, -Gln-, -Asn-, and -Asp-;

$AA_3$ is selected from the group consisting of -Leu-, -Met-, -MetO-, -MetO_2-, -Glu-, and -Phe-, $AA_4$ is selected from the group consisting of -His- and -Glu-;

$AA_5$ is selected from the group consisting of -Arg-, -His-, -Lys-, -Gln-, -Asn- and -Asp-;

$AA_6$ is selected from the group consisting of -Ile-, -Lys- and -Arg-;

$AA_7$ is selected from the group consisting of -Met-, -MetO- and -MetO_2-;

$AA_8$ is selected from the group consisting of -Asp- and -Ala-;

$AA_9$ is selected from the group consisting of -Gln-, -Asn- and a bond;

W, X, Y, Z are amino acids and are independently selected from amongst themselves;

n, m, p and q are independently selected from amongst themselves and have a value of 0 or 1;

n+m+p+q is smaller than or equal to 2;

$R_1$ is selected from the group consisting of H, a polymer derived from polyethylene glycol, a non-cyclic substituted or unsubstituted aliphatic group, substituted or unsubstituted alicyclyl, substituted or unsubstituted heterocyclyl, substituted or unsubstituted heteroarylalkyl, substituted or unsubstituted aryl, substituted or unsubstituted aralkyl and $R_5$—CO—, wherein $R_5$ is selected from the group consisting of H, a non-cyclic substituted or unsubstituted aliphatic group, substituted or unsubstituted alicyclyl, substituted or unsubstituted aryl, substituted or unsubstituted aralkyl, substituted or unsubstituted heterocyclyl and substituted or unsubstituted heteroarylalkyl;

$R_2$ is selected from the group consisting of —$NR_3R_4$, —$OR_3$ and —$SR_3$, wherein $R_3$ and $R_4$ are independently selected from the group consisting of H, a polymer derived from polyethylene glycol, a non-cyclic substituted or unsubstituted aliphatic group, substituted or unsubstituted alicyclyl, substituted or unsubstituted heterocyclyl, substituted or unsubstituted heteroarylalkyl, substituted or unsubstituted aryl, and substituted or unsubstituted aralkyl;

wherein at least one of:

$R_3$ is not H, and $R_2$ is not OH, and $R_1$ and $R_2$ are not α-amino acids.

* * * * *